United States Patent
Hatakeyama

(10) Patent No.: US 11,994,799 B2
(45) Date of Patent: May 28, 2024

(54) NEGATIVE RESIST COMPOSITION AND PATTERN FORMING PROCESS

(71) Applicant: Shin-Etsu Chemical Co., Ltd., Tokyo (JP)

(72) Inventor: Jun Hatakeyama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 17/864,748

(22) Filed: Jul. 14, 2022

(65) Prior Publication Data
US 2023/0116747 A1 Apr. 13, 2023

(30) Foreign Application Priority Data
Jul. 28, 2021 (JP) ................ 2021-123215

(51) Int. Cl.
| | | |
|---|---|---|
| G03F 7/004 | (2006.01) | |
| C07C 303/32 | (2006.01) | |
| C07C 309/06 | (2006.01) | |
| C07C 309/10 | (2006.01) | |
| C07C 309/12 | (2006.01) | |
| C07C 309/13 | (2006.01) | |
| C07C 381/12 | (2006.01) | |
| G03F 7/027 | (2006.01) | |
| G03F 7/029 | (2006.01) | |
| G03F 7/033 | (2006.01) | |
| G03F 7/038 | (2006.01) | |
| G03F 7/20 | (2006.01) | |
| G03F 7/30 | (2006.01) | |

(52) U.S. Cl.
CPC .......... *G03F 7/0045* (2013.01); *C07C 303/32* (2013.01); *C07C 309/06* (2013.01); *C07C 309/10* (2013.01); *C07C 309/12* (2013.01); *C07C 309/13* (2013.01); *C07C 381/12* (2013.01); *G03F 7/0048* (2013.01); *G03F 7/027* (2013.01); *G03F 7/029* (2013.01); *G03F 7/033* (2013.01); *G03F 7/0382* (2013.01); *G03F 7/2006* (2013.01); *G03F 7/30* (2013.01)

(58) Field of Classification Search
CPC .. G03F 7/0045; G03F 7/0382; G03F 77/0397; G03F 7/027; G03F 7/033; C07C 303/32; C07C 309/06; C07C 309/10; C07C 309/12; C07C 309/13; C07C 381/12
See application file for complete search history.

(56) References Cited

U.S. PATENT DOCUMENTS

| | | | | |
|---|---|---|---|---|
| 5,101,053 A | * | 3/1992 | Boettcher | C07C 381/12 549/6 |
| 2011/0171569 A1 | * | 7/2011 | Nishimae | C07D 339/08 544/5 |
| 2015/0093703 A1 | * | 4/2015 | Miyata | G03F 7/11 430/281.1 |

FOREIGN PATENT DOCUMENTS

JP 2008-281974 A 11/2008

OTHER PUBLICATIONS

Kishikawa, Y. et al., "Assessment of trade-off between resist resolution and sensitivity for optimization of hyper-NA immersion lithography", SPIE, 2007, vol. 6520, pp. 65203L-1 to 65203L-9, cited in Specification (9 pages).

Nakao, S. et al, "0.12µm Hole Pattern Formation by KrF Lithography for Giga Bit DRAM", IEEE IEDM Tech. Digest, 1996, pp. 61 to 64, cited in Specification (4 pages).

To, H. et al, "New UV Resists With Negative or Positive Tone", VLSI. Technol. Symp., 1982, pp. 86 to 87, cited in Specification (2 pages).

* cited by examiner

*Primary Examiner* — John S Chu
(74) *Attorney, Agent, or Firm* — WHDA, LLP

(57) ABSTRACT

A negative resist composition is provided comprising a base polymer and an acid generator in the form of a sulfonium salt consisting of a sulfonate anion having a maleimide group and a cation having a polymerizable double bond. The resist composition adapted for organic solvent development exhibits a high resolution and improved LWR or CDU.

9 Claims, No Drawings

NEGATIVE RESIST COMPOSITION AND PATTERN FORMING PROCESS

CROSS-REFERENCE TO RELATED APPLICATION

This non-provisional application claims priority under 35 U.S.C. § 119(a) on Patent Application No. 2021-123215 filed in Japan on Jul. 28, 2021, the entire contents of which are hereby incorporated by reference.

TECHNICAL FIELD

This invention relates to a negative resist composition and a pattern forming process.

BACKGROUND ART

To meet the demand for higher integration density and operating speed of LSIs, the effort to reduce the pattern rule is in rapid progress. As the use of 5G high-speed communications and artificial intelligence (AI) is widely spreading, high-performance devices are needed for their processing. As the advanced miniaturization technology, manufacturing of microelectronic devices at the 5-nm node by the lithography using EUV of wavelength 13.5 nm has been implemented in a mass scale. Studies are made on the application of EUV lithography to 3-nm node devices of the next generation and 2-nm node devices of the next-but-one generation.

As the feature size reduces, image blurs due to acid diffusion become a problem. To insure resolution for fine patterns with a sub-45-nm size, not only an improvement in dissolution contrast is important as previously reported, but the control of acid diffusion is also important as reported in Non-Patent Document 1. Since chemically amplified resist compositions are designed such that sensitivity and contrast are enhanced by acid diffusion, an attempt to minimize acid diffusion by reducing the temperature and/or time of post-exposure bake (PEB) fails, resulting in drastic reductions of sensitivity and contrast.

In forming a pattern having a narrower pitch than the wavelength of exposure light, it is effective to utilize the interference lithography. In particular, the interference of high contrast light between X-direction lines and Y-direction lines generates black spots with high contrast. Non-Patent Document 2 describes that a hole pattern with better CDU can be formed by combining the interference lithography with a negative resist material. Non-Patent Document 2 uses a negative resist material comprising a crosslinker capable of inducing reaction between polymer molecules with the aid of an acid. This chemically amplified negative resist material suffers from several problems including image blur due to the acid diffusion (as mentioned above), swell due to the penetration of a developer between partially crosslinked polymer segments, and concomitant pattern collapse and degradation of CDU or edge roughness (LWR).

The fabrication of negative tone patterns by organic solvent development is a prior art technique employed from the past. Non-Patent Document 3 describes that negative tone patterns are obtained by using xylene as the developer for a resist material based on cyclized rubber, and anisole as the developer for an initial chemically amplified resist material based on poly-tert-butoxycarbonyloxystyrene.

Patent Document 1 discloses that a negative pattern is formed by using a polymethacrylate having a carboxy group substituted with an acid labile group as the base polymer to formulate a chemically amplified resist material, exposing it to ArF excimer laser light, and developing in an organic solvent. This organic solvent development process, combined with immersion lithography through an optical system with a NA in excess of 1 or double patterning lithography, is used in the fabrication of microelectronic devices of sub-20-nm node.

It has never been attempted for the EUV lithography to form patterns having a pitch shorter than the exposure wavelength. This is because the EUV lithography uses a NA of 0.33 which is significantly smaller than the NA of 1.35 for the ArF immersion lithography, and the effect of interference exposure is low. While the EUV lithography of the next generation utilizes a NA of 0.55, it never happens even in this generation that a negative resist material is more advantageous in hole pattern formation.

In the EUV lithography, negative tone patterns become necessary only when isolated patterns and pillar patterns are formed. Since the mask used herein has a greater proportion of light-shielded regions, there is the merit that patterns are unsusceptible to the influence of defects in the mask blank.

When isolated patterns or pillar patterns are formed on photomasks, negative resist materials are preferably used. This is because the negative resist material needs a smaller image writing area and hence, a shorter image writing time. An improvement in the throughput is thus expectable. The resist material adapted for the EB lithography for forming mask patterns also needs a higher resolution.

The organic solvent development causes less swell than the alkaline aqueous solution development, sometimes leading to better values of CDU or LWR. The organic solvent development, however, has the problem of low resolution because the dissolution contrast is lower than that of the alkaline development. When a crosslinker capable of reaction with the aid of acid is added to a resist material for the purpose of increasing the dissolution contrast during organic solvent development, the above-mentioned problem of swell arises in the organic solvent development as well. It is necessary to improve the dissolution contrast without causing swell.

CITATION LIST

Patent Document 1: JP-A 2008-281974
Non-Patent Document 1: SPIE Vol. 6520 65203L-1 (2007)
Non-Patent Document 2: IEEE IEDM Tech. Digest 61 (1996)
Non-Patent Document 3: VLSI. Technol. Symp. p 86-87 (1982)

SUMMARY OF INVENTION

It is desired to have a negative resist material adapted for the organic solvent development process, which can reduce the LWR of line patterns or improve the CDU of hole patterns and exhibits a high resolution. To this end, the resist material should display such properties as low swell and high contrast during organic solvent development.

An object of the invention is to provide a negative resist composition adapted for the organic solvent development, capable of forming patterns with a high resolution and improved LWR or CDU, and a pattern forming process using the same.

The inventor has found that a resist composition comprising a base polymer and an acid generator in the form of a sulfonium salt consisting of a sulfonate anion having a maleimide group and a cation having a polymerizable double bond is such that the sulfonium salt crosslinks upon light exposure whereby a higher acid diffusion-controlling effect is exerted, the solubility of exposed resist in an organic solvent is reduced, and the dissolution contrast is improved. The resist composition is capable of forming a pattern with reduced values of LWR and CDU, improved resolution, and a wide process margin.

In one aspect, the invention provides a negative resist composition comprising a base polymer and an acid generator in the form of a sulfonium salt consisting of a sulfonate anion having a maleimide group and a cation having a polymerizable double bond.

Preferably, the sulfonium salt has the formula (A).

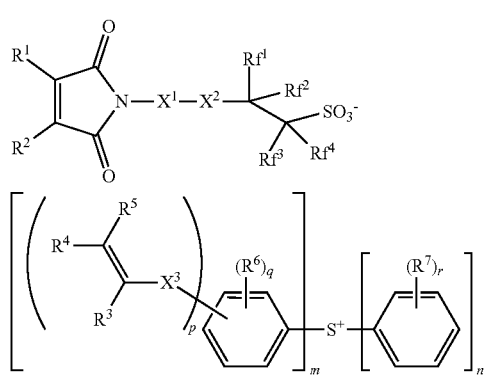

Herein m is an integer of 1 to 3, n is an integer of 0 to 2, meeting m+n=3, p is 1 or 2, q is an integer of 0 to 4, meeting $1 \leq p+q \leq 5$, r is an integer of 0 to 5. $X^1$ is a single bond or a $C_1$-$C_{20}$ hydrocarbylene group which may contain oxygen, sulfur, nitrogen or halogen. $X^2$ is an ester bond or $C_1$-$C_8$ alkanediyl group. $X^3$ is a single bond, ester bond, ether bond, amide bond, urethane bond, or a $C_1$-$C_{10}$ alkanediyl group in which some constituent —$CH_2$— may be replaced by an ester bond, ether bond, amide bond or urethane bond. $R^1$ and $R^2$ are each independently hydrogen or a $C_1$-$C_{10}$ saturated hydrocarbyl group, $R^1$ and $R^2$ may bond together to form a ring with the carbon atoms to which they are attached. $R^3$ to $R^5$ are each independently hydrogen, halogen, or a $C_1$-$C_{40}$ saturated hydrocarbyl group in which some or all of the hydrogen atoms may be substituted by fluorine or hydroxy, some constituent —$CH_2$— may be replaced by an ether bond or ester bond, and some carbon-carbon bond may be a double bond. $R^6$ and $R^7$ are each independently halogen, cyano, nitro, mercapto, sulfo, a $C_1$-$C_{10}$ saturated hydrocarbyl group, or a $C_7$-$C_{20}$ aralkyl group, the saturated hydrocarbyl group and aralkyl group may contain oxygen, sulfur, nitrogen or halogen, two $R^6$ or two $R^7$ may bond together to form a ring with the benzene ring to which they are attached, and $R^6$ and $R^7$ may bond together to form a ring with the benzene rings to which they are attached and the intervening sulfur. $Rf^1$ to $Rf^4$ are each independently hydrogen, fluorine or trifluoromethyl, at least one of $Rf^1$ to $Rf^4$ being fluorine or trifluoromethyl, $Rf^1$ and $Rf^2$, taken together, may form a carbonyl group.

In a preferred embodiment, the base polymer comprises repeat units having the formula (a1):

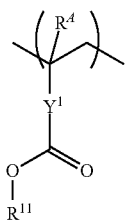

wherein $R^A$ is hydrogen or methyl, $Y^1$ is a single bond, phenylene, naphthylene or a $C_1$-$C_{12}$ linking group which contains at least one moiety selected from an ester bond, ether bond and lactone ring, and $R^{11}$ is an acid labile group.

The resist composition may further comprise an organic solvent, quencher, crosslinker, and/or surfactant.

In another aspect, the invention provides a pattern forming process comprising the steps of applying the negative resist composition defined herein onto a substrate to form a resist film thereon, exposing the resist film to high-energy radiation, and developing the exposed resist film in an organic solvent developer.

Preferably, the developer comprises at least one organic solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, isopentyl acetate, 2-methylbutyl acetate, hexyl acetate, butenyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

Typically, the high-energy radiation is KrF excimer laser, ArF excimer laser, EB, or EUV of wavelength 3 to 15 nm.

Advantageous Effects of Invention

In the resist composition comprising a base polymer and a sulfonium salt consisting of a sulfonate anion having a maleimide group and a cation having a polymerizable double bond, crosslinking reaction takes place upon light exposure. The progress of crosslinking reaction suppresses acid diffusion and promotes insolubilization of exposed resist in the developer. A resist composition having a high resolution and improved LWR or CDU can be designed.

DESCRIPTION OF PREFERRED EMBODIMENTS

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. In chemical formulae, the broken line designates a valence bond; Me stands for methyl, and Ac for acetyl. As used herein, the term "halogenated" (e.g., fluorinated) group refers to a halogen-substituted group (e.g., fluorine-substituted group). The terms "group" and "moiety" are interchangeable.

The abbreviations and acronyms have the following meaning.
EB: electron beam
EUV: extreme ultraviolet
Mw: weight average molecular weight
Mn: number average molecular weight
Mw/Mn: molecular weight distribution or dispersity
GPC: gel permeation chromatography
PEB: post-exposure bake
PAG: photoacid generator
LWR: line width roughness
CDU: critical dimension uniformity Negative Resist Composition The invention provides a negative resist composition comprising a base polymer and an acid generator in the form of a sulfonium salt consisting of a sulfonate anion having a maleimide group and a cation having a polymerizable double bond.

Sulfonium Salt

The sulfonium salt consisting of a sulfonate anion having a maleimide group and a cation having a polymerizable double bond functions as an acid generator. The preferred sulfonium salt has the formula (A).

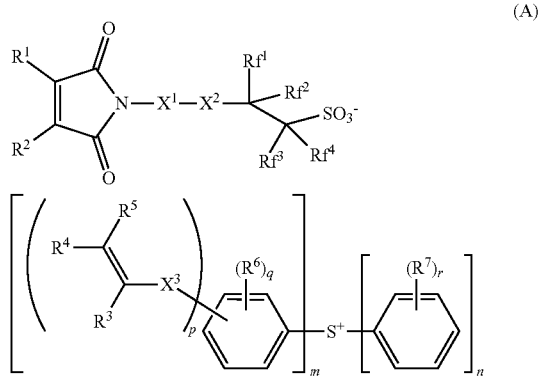

In formula (A), m is an integer of 1 to 3, n is an integer of 0 to 2, meeting m+n=3, p is 1 or 2, q is an integer of 0 to 4, meeting 1≤p+q≤5, and r is an integer of 0 to 5.

In formula (A), $X^1$ is a single bond or a $C_1$-$C_{20}$ hydrocarbylene group which may contain oxygen, sulfur, nitrogen or halogen.

The $C_1$-$C_{20}$ hydrocarbylene group $X^1$ may be saturated or unsaturated and straight, branched or cyclic. Examples thereof include $C_1$-$C_{20}$ alkanediyl groups such as methanediyl, ethane-1,1-diyl, ethane-1,2-diyl, propane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, and dodecane-1,12-diyl; $C_3$-$C_{20}$ cyclic saturated hydrocarbylene groups such as cyclopentanediyl, cyclohexanediyl, norbornanediyl, and adamantanediyl; $C_2$-$C_{20}$ unsaturated aliphatic hydrocarbylene groups such as vinylene and propene-1,3-diyl; $C_6$-$C_{20}$ arylene groups such as phenylene and naphthylene; and combinations thereof. In the hydrocarbylene group, some or all of the hydrogen atoms may be substituted by a moiety containing oxygen, sulfur, nitrogen or halogen, and some constituent —$CH_2$— may be replaced by a moiety containing oxygen, sulfur or nitrogen, so that the group may contain a hydroxy moiety, fluorine, chlorine, bromine, iodine, cyano moiety, carbonyl moiety, ether bond, ester bond, sulfonic ester bond, carbonate bond, lactone ring, sultone ring, carboxylic anhydride (—C(=O)—O—C(=O)—), or haloalkyl moiety.

In formula (A), $X^2$ is an ester bond or $C_1$-$C_8$ alkanediyl group. Examples of the alkanediyl group are as exemplified above for the $C_1$-$C_{20}$ alkanediyl group $X^1$, but of 1 to 8 carbon atoms.

In formula (A), $X^3$ is a single bond, ester bond, ether bond, amide bond, urethane bond, or a $C_1$-$C_{10}$ alkanediyl group in which some constituent —$CH_2$— may be replaced by an ester bond, ether bond, amide bond or urethane bond. Suitable alkanediyl groups include methanediyl, ethane-1,1-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, and decane-1,10-diyl.

In formula (A), $R^1$ and $R^2$ are each independently hydrogen or a $C_1$-$C_{10}$ saturated hydrocarbyl group. The saturated hydrocarbyl group may be straight, branched or cyclic. Examples thereof include $C_1$-$C_{10}$ alkyl groups such as methyl, ethyl, propyl, isopropyl, butyl, isobutyl, sec-butyl, tert-butyl, pentyl, neopentyl, hexyl, heptyl, 2-ethylhexyl, nonyl, and decyl; and $C_3$-$C_{10}$ cyclic saturated hydrocarbyl groups such as cyclopentyl and cyclohexyl. $R^1$ and $R^2$ may bond together to form a ring with the carbon atoms to which they are attached. The preferred ring is a 5 or 6-membered ring.

In formula (A), $R^3$ to $R^5$ are each independently hydrogen, halogen, or a $C_1$-$C_{40}$ saturated hydrocarbyl group. In the saturated hydrocarbyl group, some or all of the hydrogen atoms may be substituted by fluorine or hydroxy, some constituent —$CH_2$— may be replaced by an ether bond or ester bond, and some carbon-carbon bond may be a double bond.

The $C_1$-$C_{40}$ saturated hydrocarbyl group represented by $R^3$ to $R^5$ may be straight, branched or cyclic. Examples thereof include $C_1$-$C_{40}$ alkyl groups such as methyl, ethyl, propyl, isopropyl, butyl, isobutyl, sec-butyl, tert-butyl, pentyl, neopentyl, hexyl, heptyl, 2-ethylhexyl, nonyl, decyl, undecyl, tridecyl, pentadecyl, heptadecyl, and icosanyl; and $C_3$-$C_{40}$ cyclic saturated hydrocarbyl groups such as cyclopentyl, cyclohexyl, 1-adamantyl, 2-adamantyl, 1-adamantylmethyl, norbornyl, norbornylmethyl, tricyclodecanyl, tetracyclododecanyl, tetracyclododecanylmethyl, and dicyclohexylmethyl.

In formula (A), $R^6$ and $R^7$ are each independently halogen, cyano, nitro, mercapto, sulfo, a $C_1$-$C_{10}$ saturated hydrocarbyl group, or a $C_7$-$C_{20}$ aralkyl group. The saturated hydrocarbyl group and aralkyl group may contain oxygen, sulfur, nitrogen or halogen. Two $R^6$ or two $R^7$ may bond together to form a ring with the benzene ring to which they are attached, and $R^1$ and $R^7$ may bond together to form a ring with the benzene rings to which they are attached and the intervening sulfur. The preferred rings are of the following structure. It is noted that the substituent on the aromatic ring, if any, is omitted from the depicted structure.

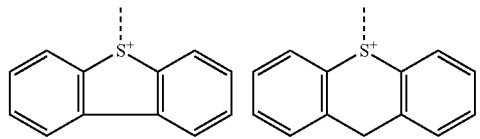

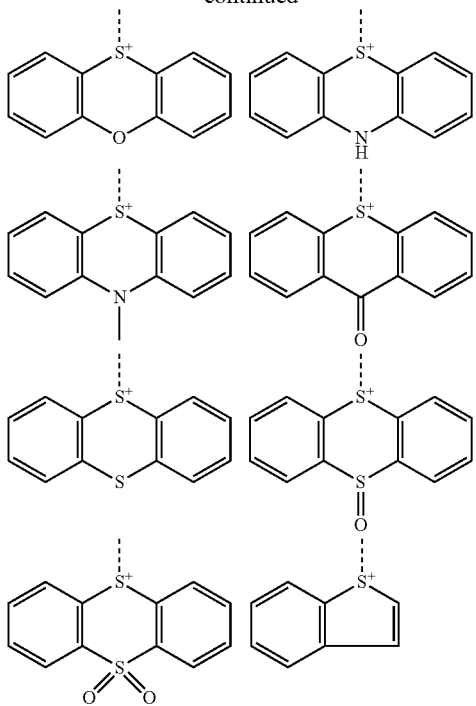
In formula (A), $Rf^1$ to $Rf^4$ are each independently hydrogen, fluorine or trifluoromethyl, at least one of $Rf^1$ to $Rf^4$ being fluorine or trifluoromethyl. $Rf^1$ and $R^2$, taken together, may form a carbonyl group.
Examples of the sulfonate anion having a maleimide group are shown below, but not limited thereto.
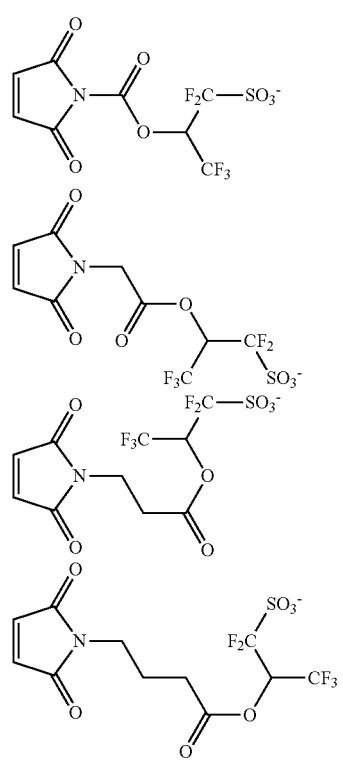
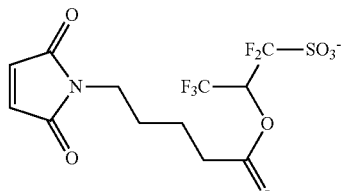
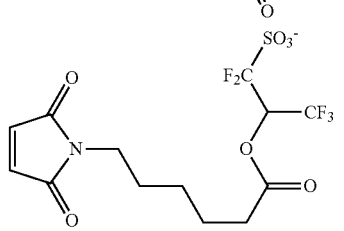
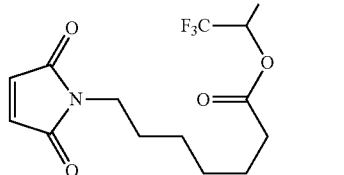
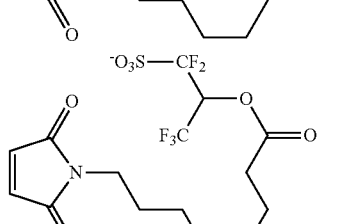
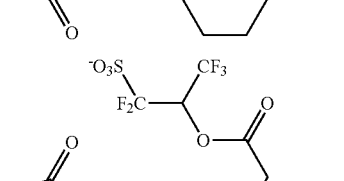
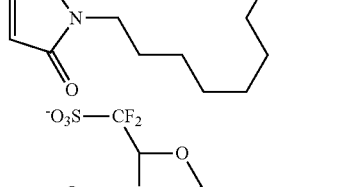
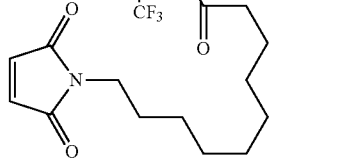
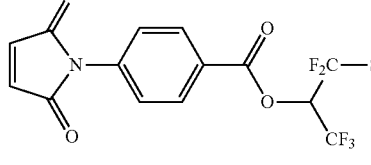
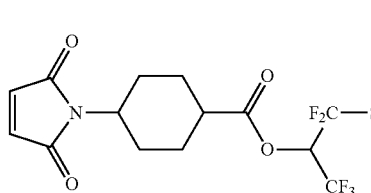

-continued
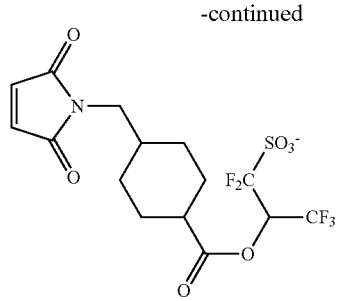
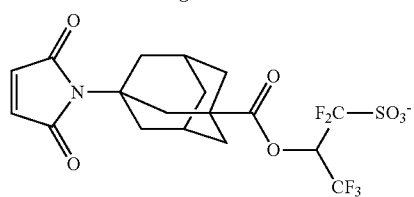
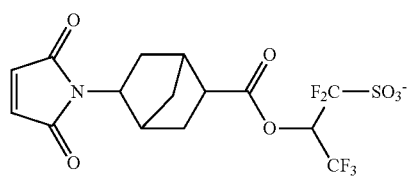
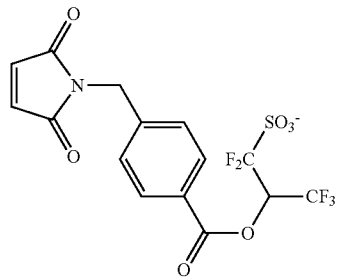
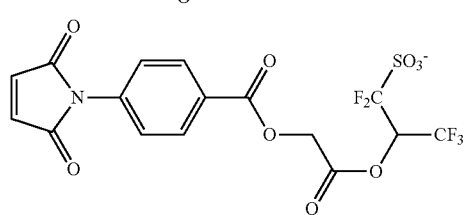
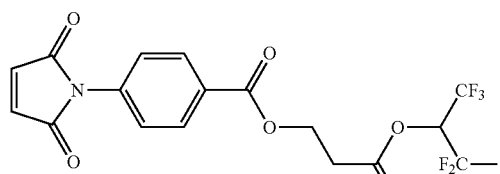
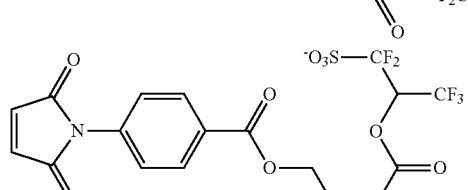
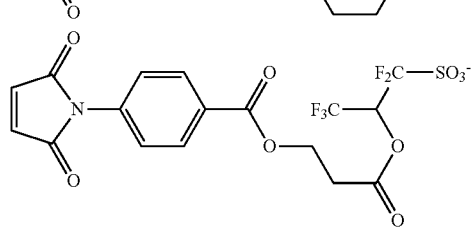
-continued
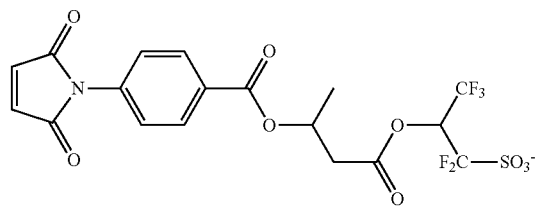
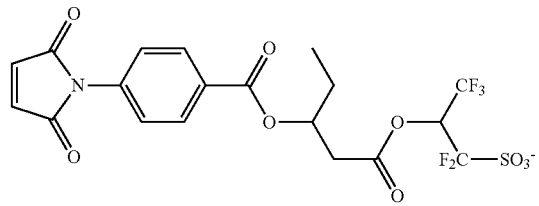
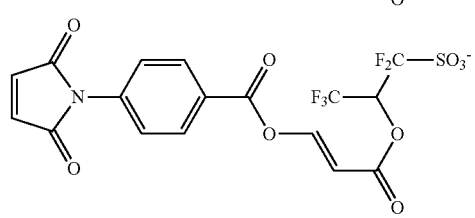
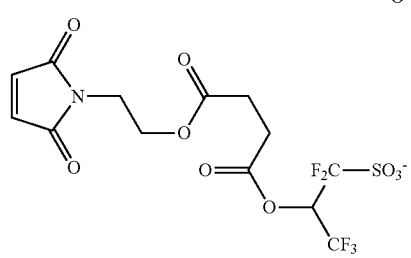
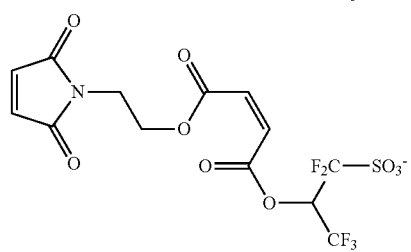
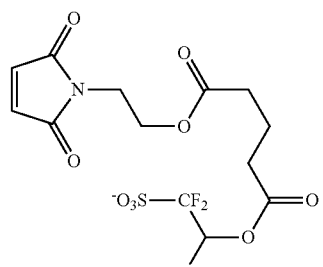
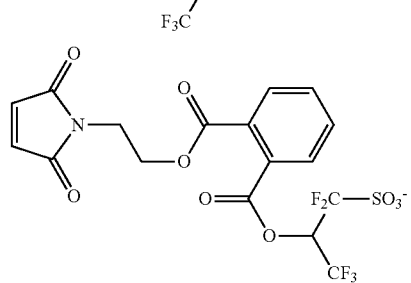

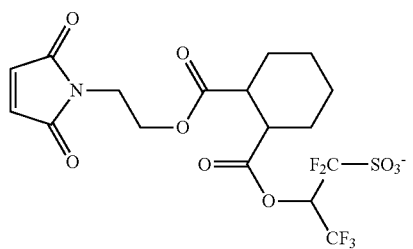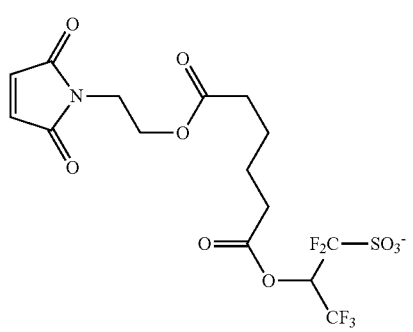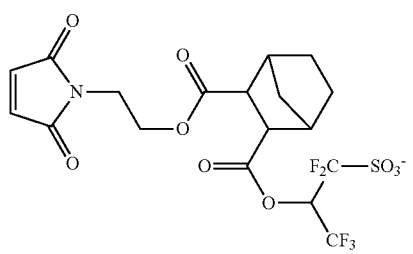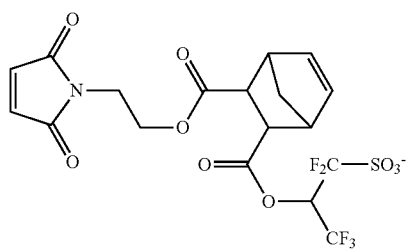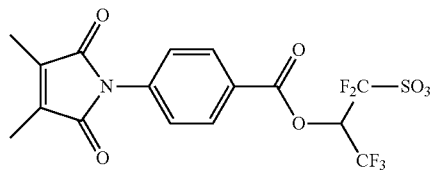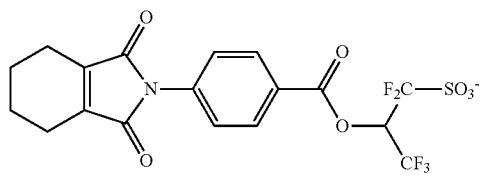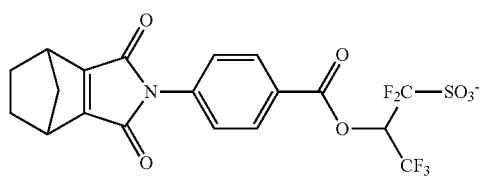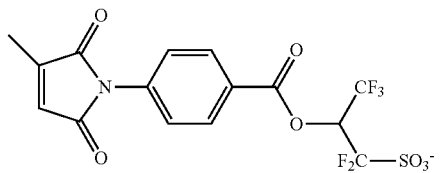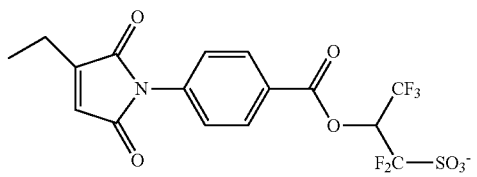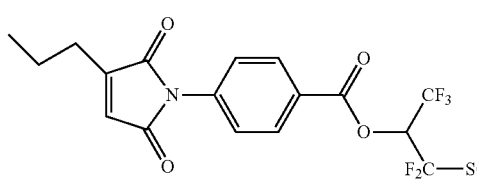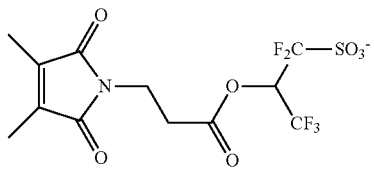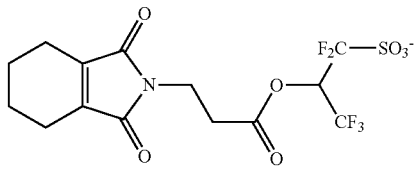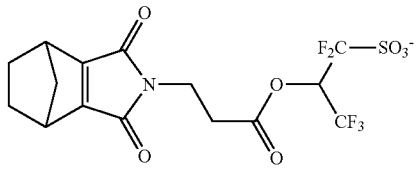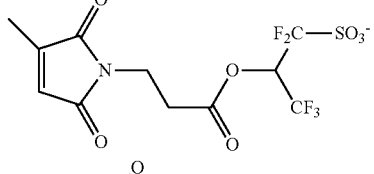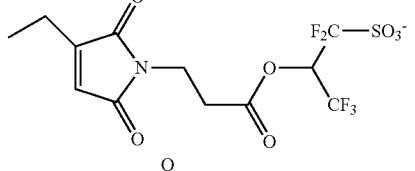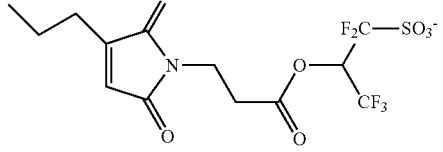

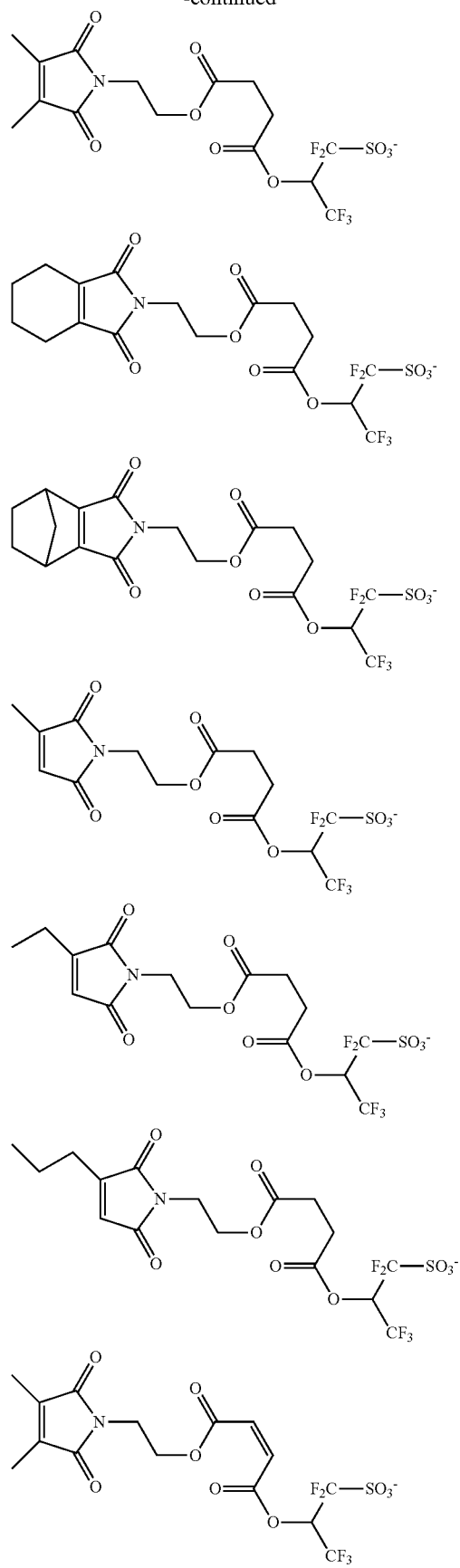
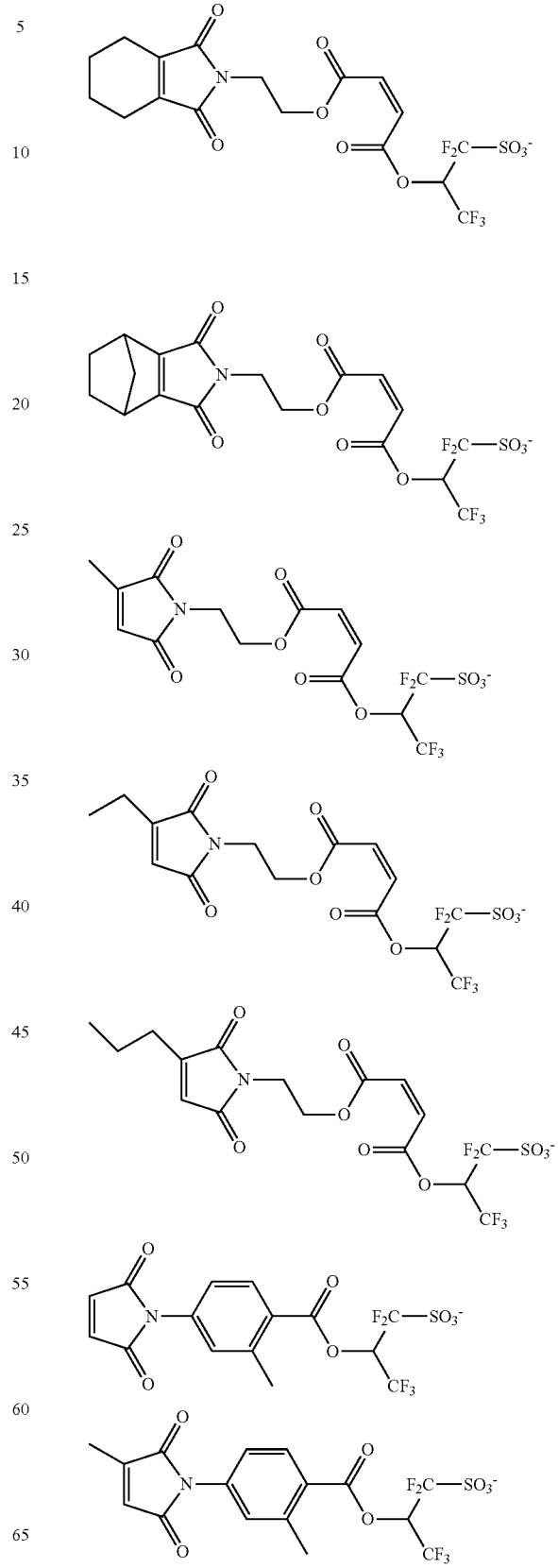

-continued
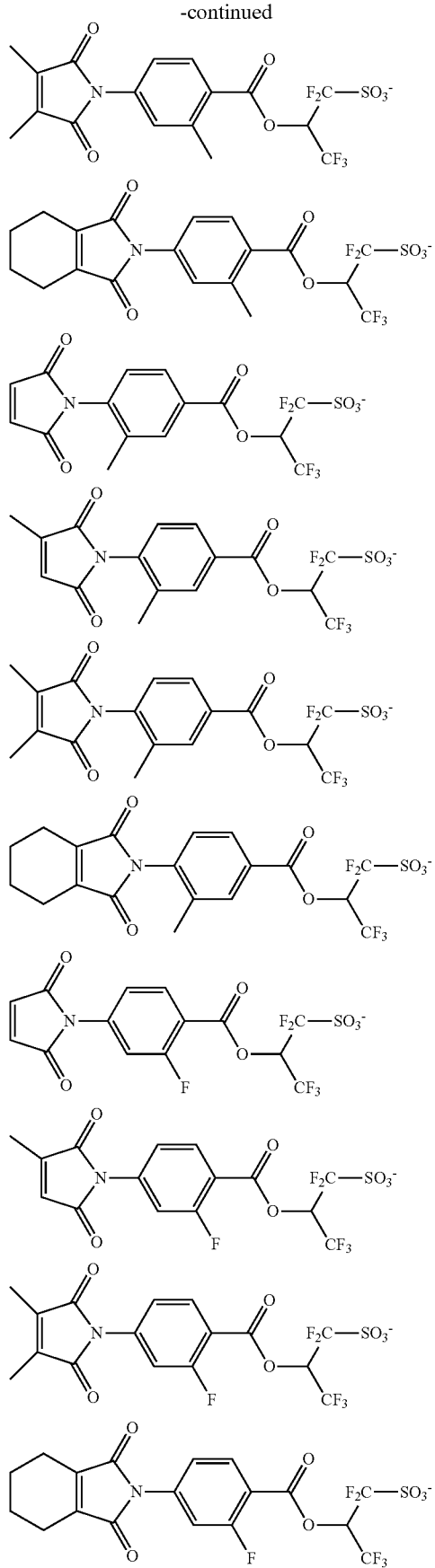
-continued
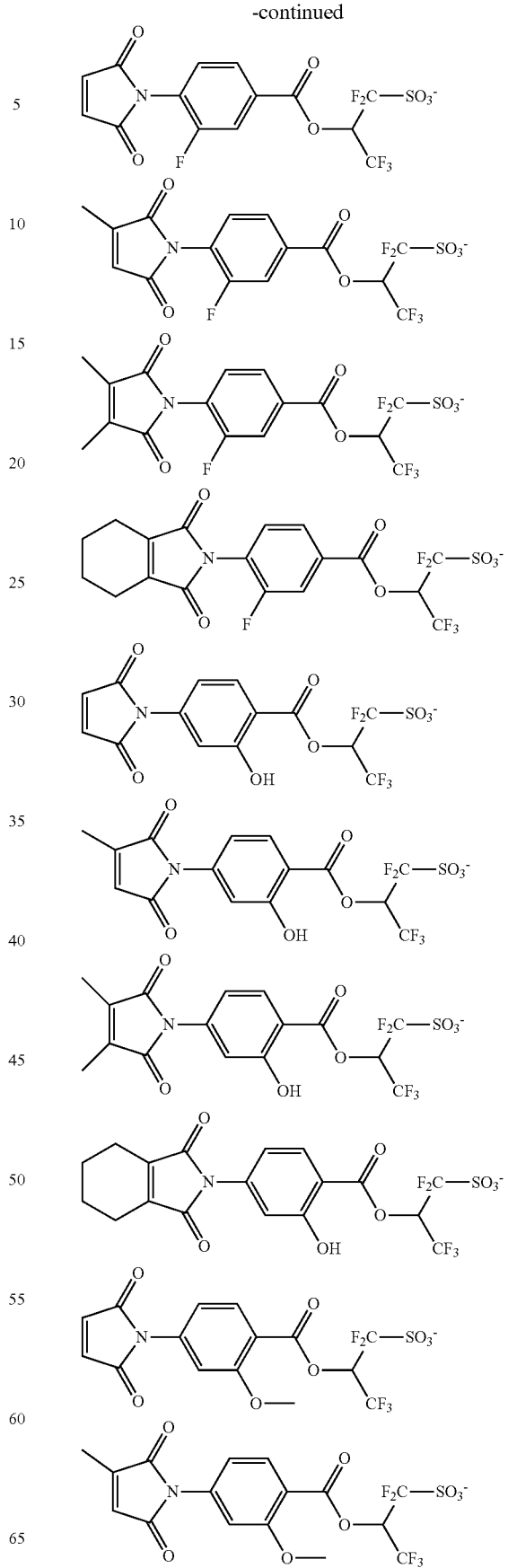

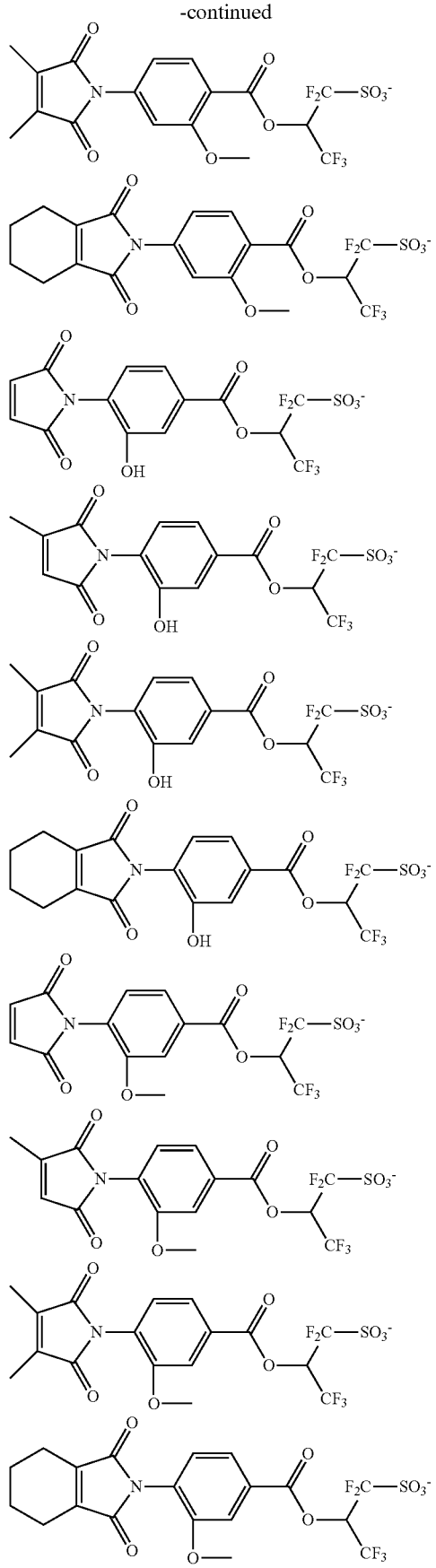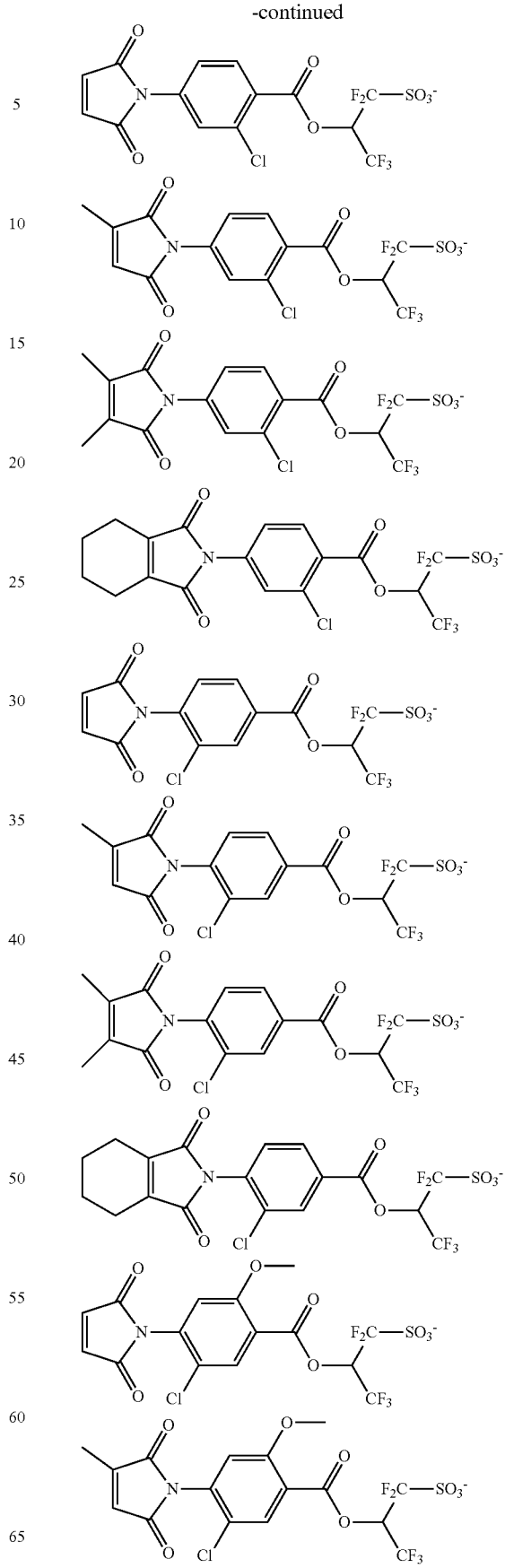

-continued
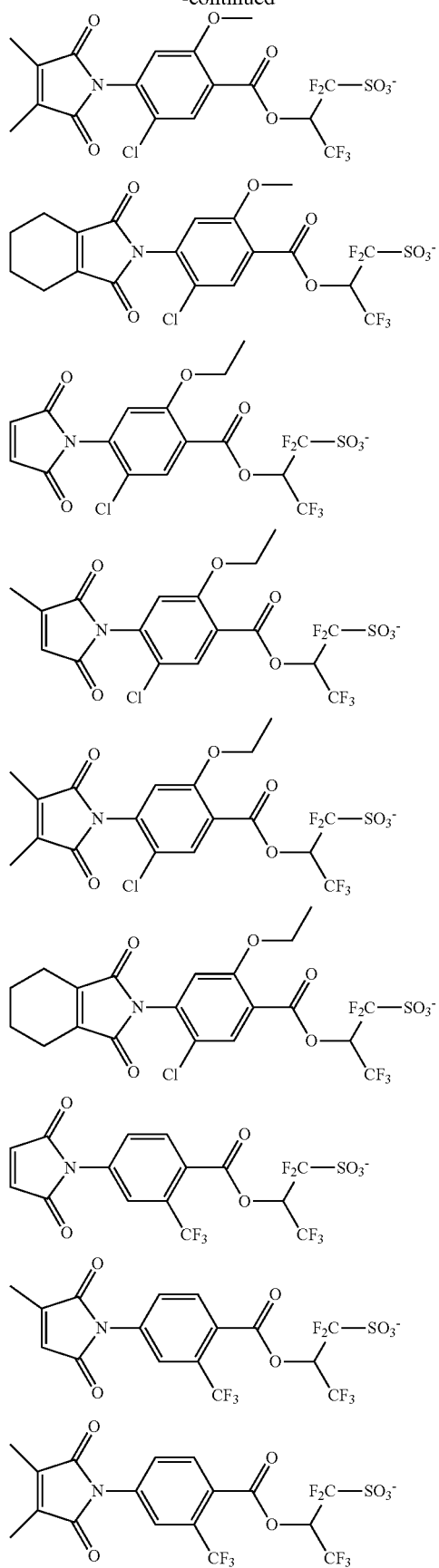
-continued
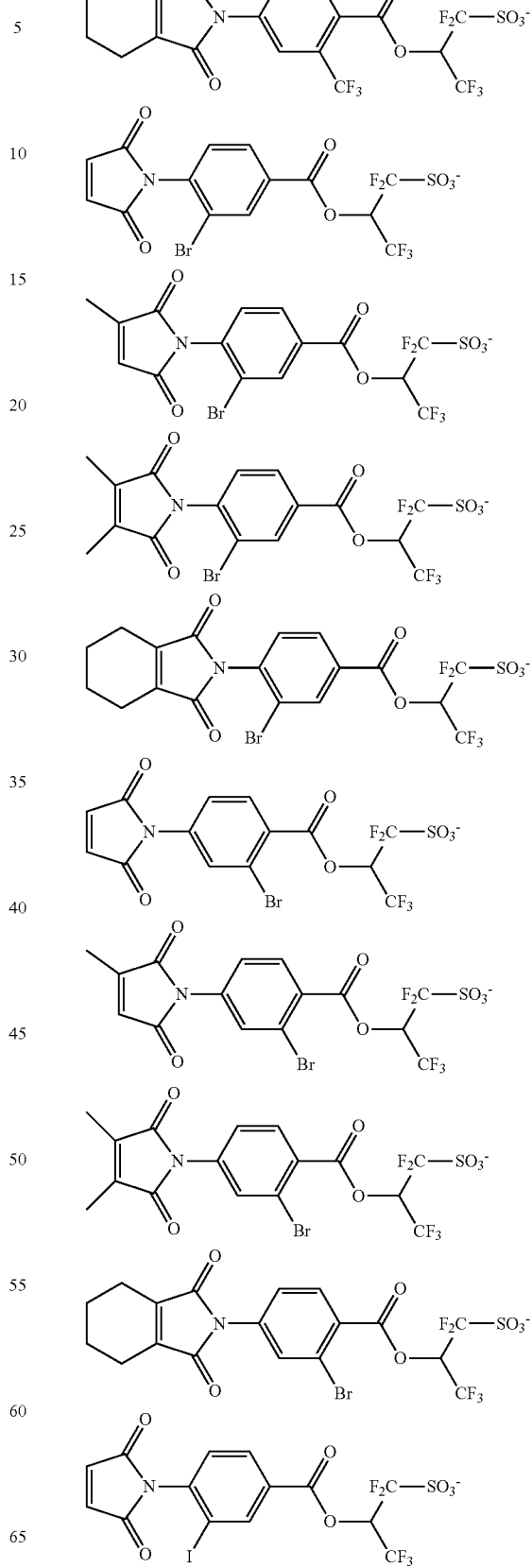

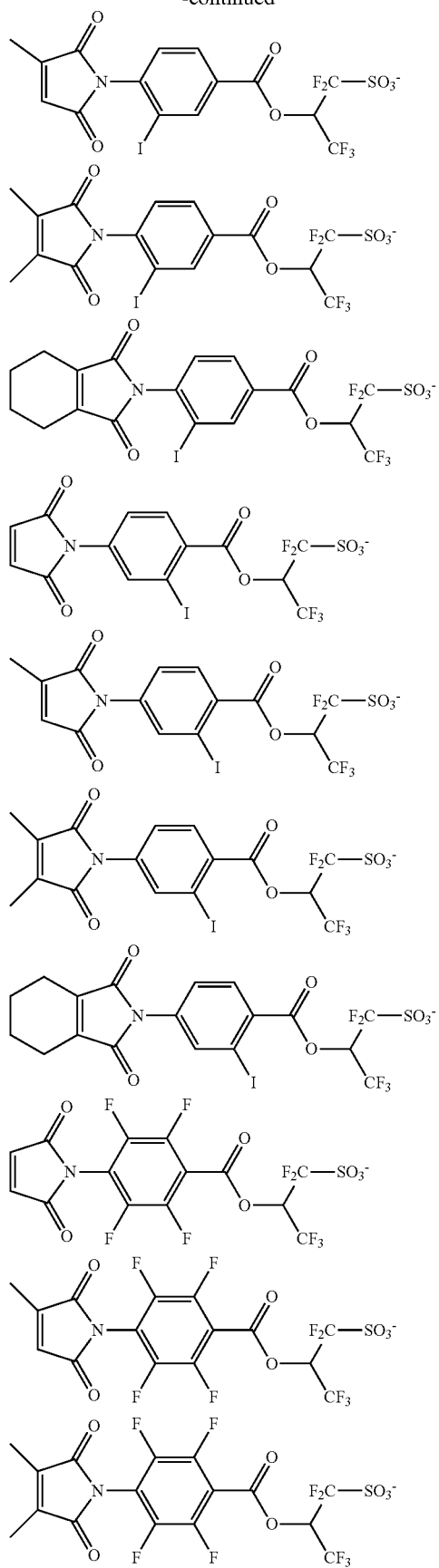
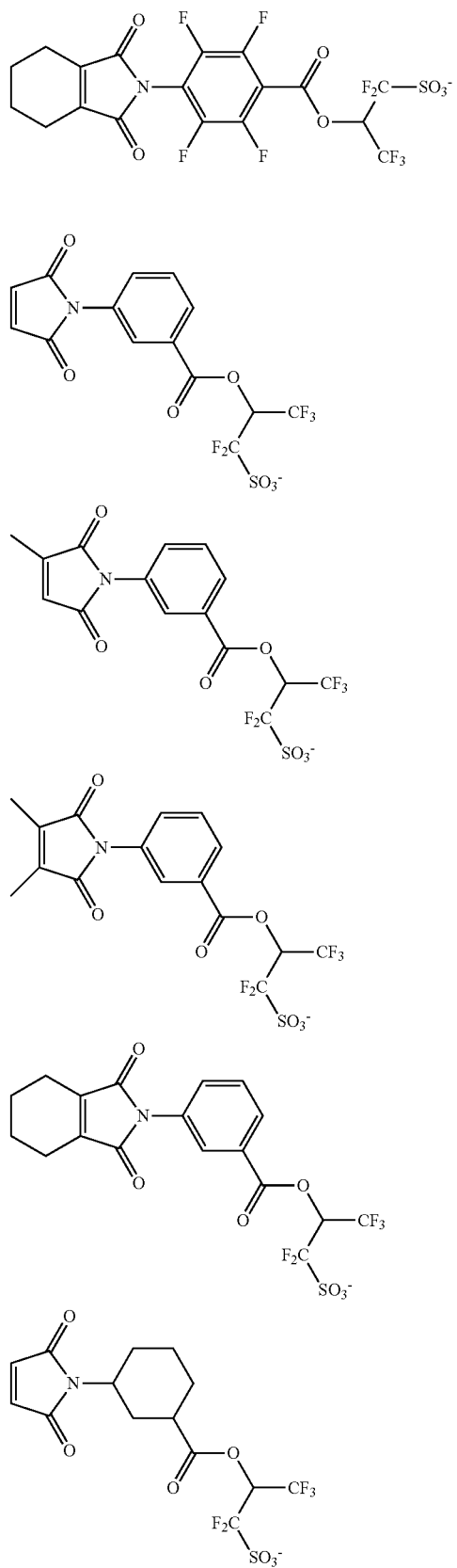

23
-continued
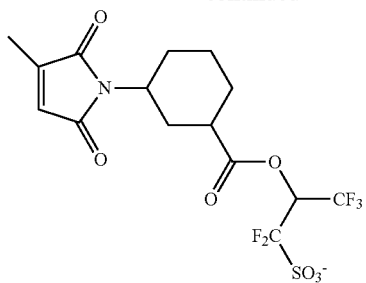
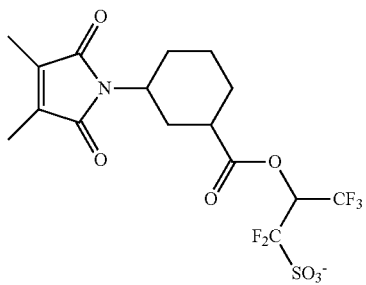
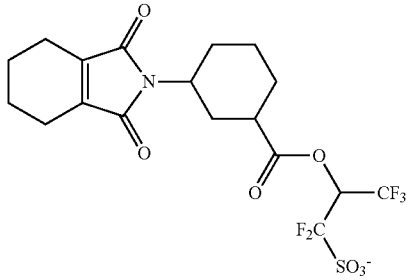
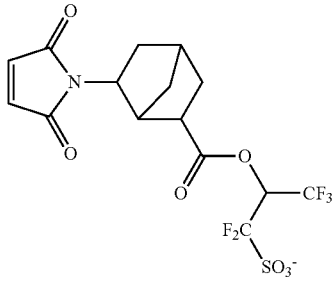
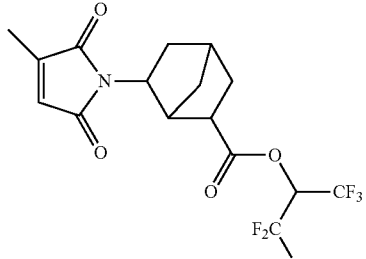
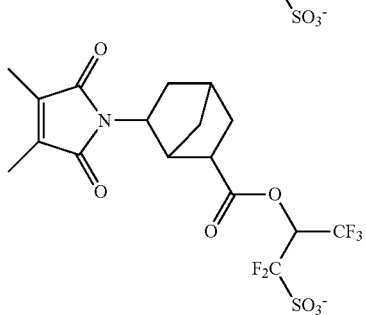
24
-continued
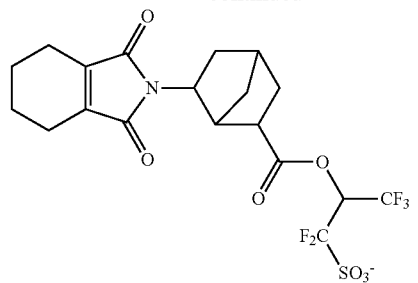
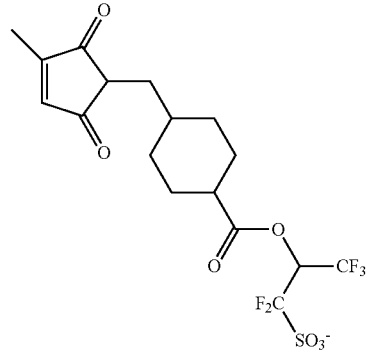
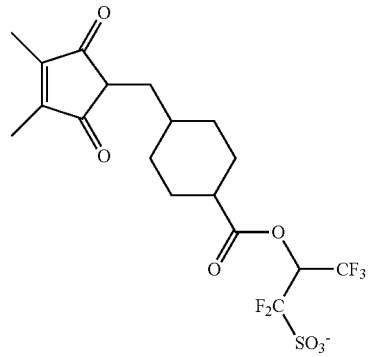
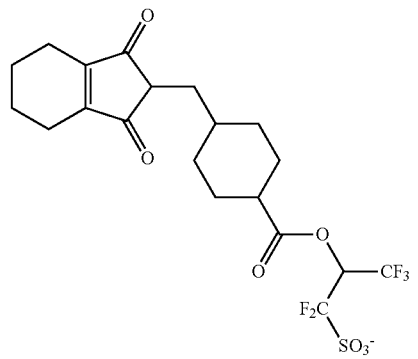
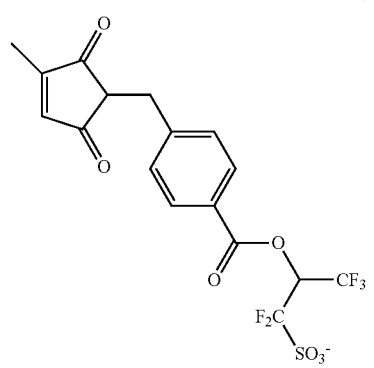

25
-continued
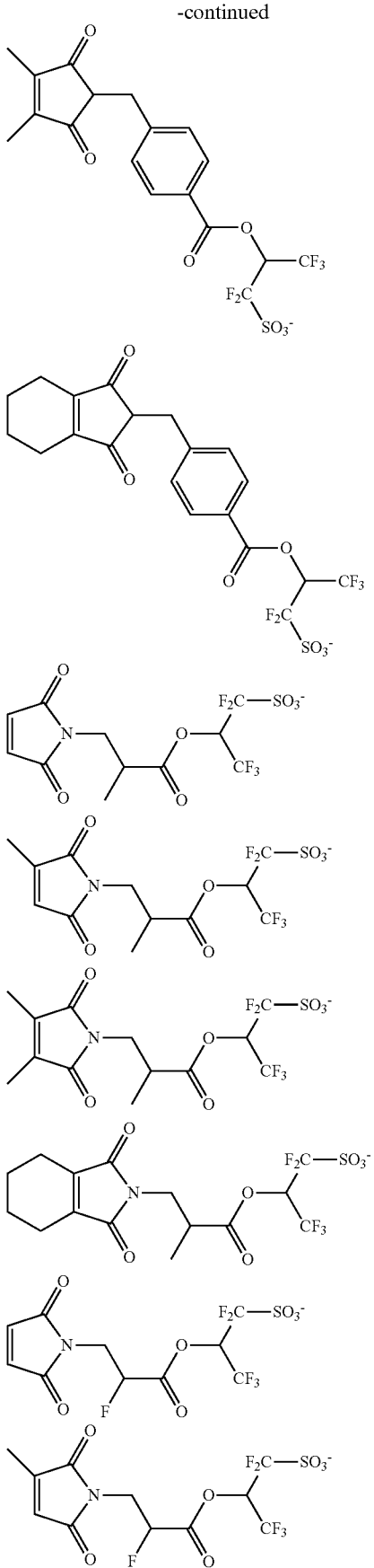
26
-continued
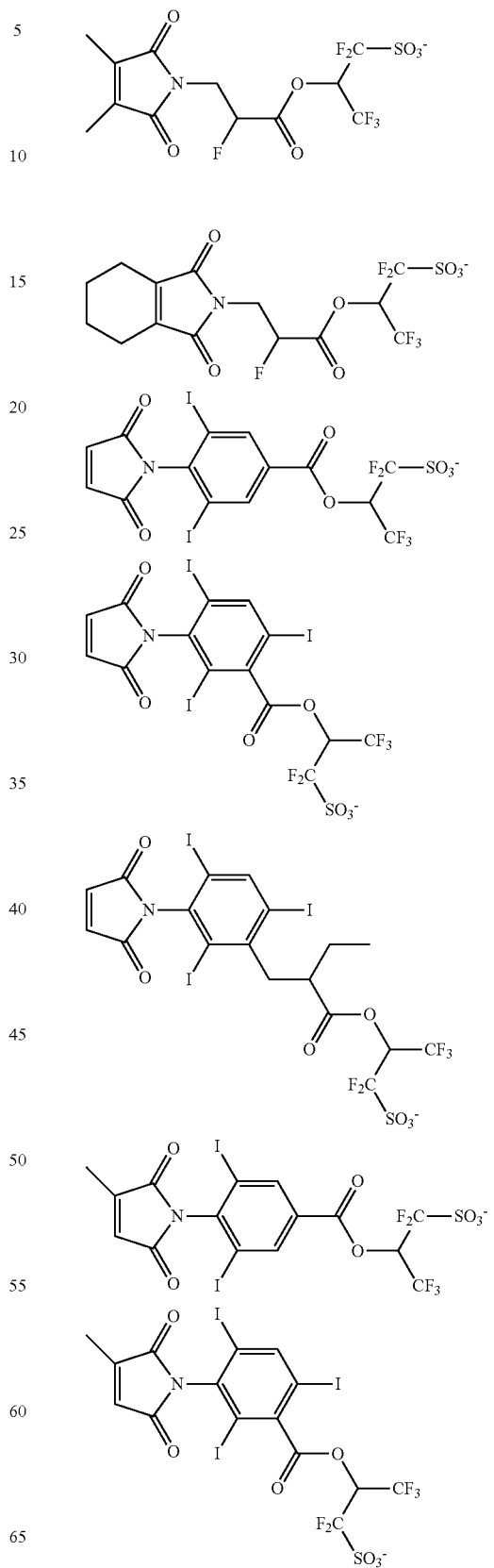

27
-continued
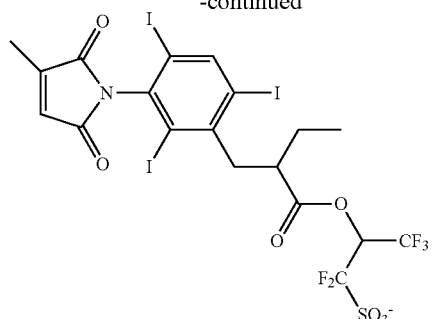
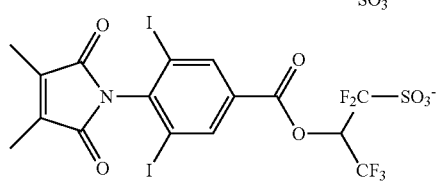
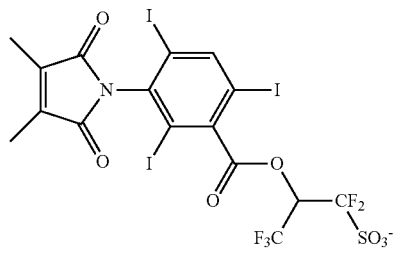
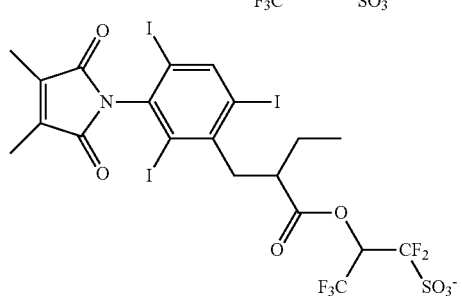
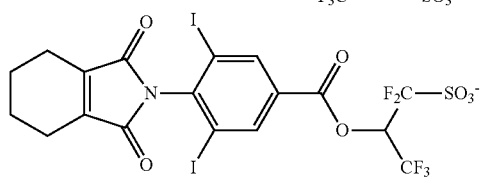
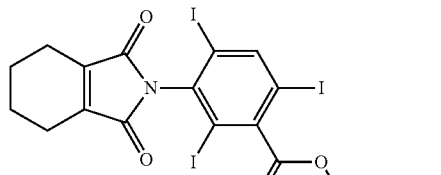
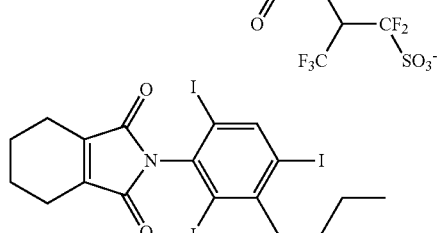
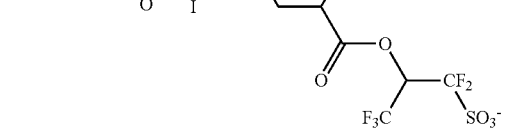
28
-continued
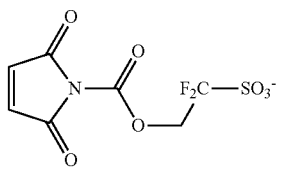
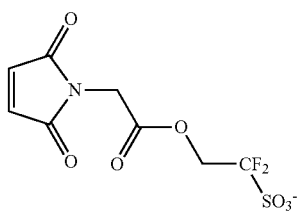
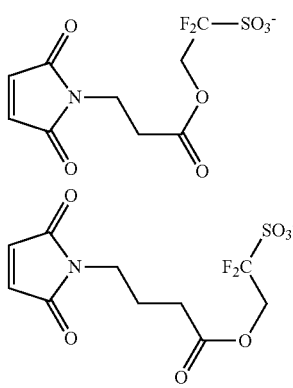
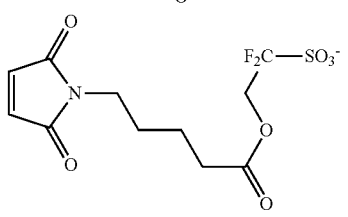
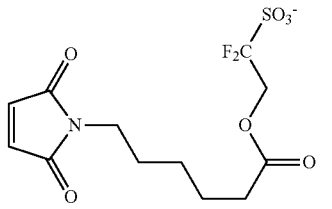
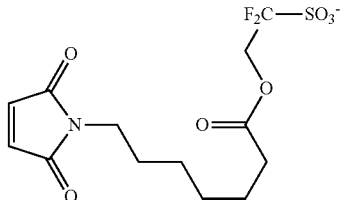
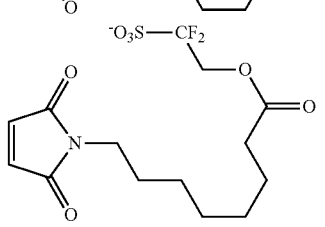

29
-continued
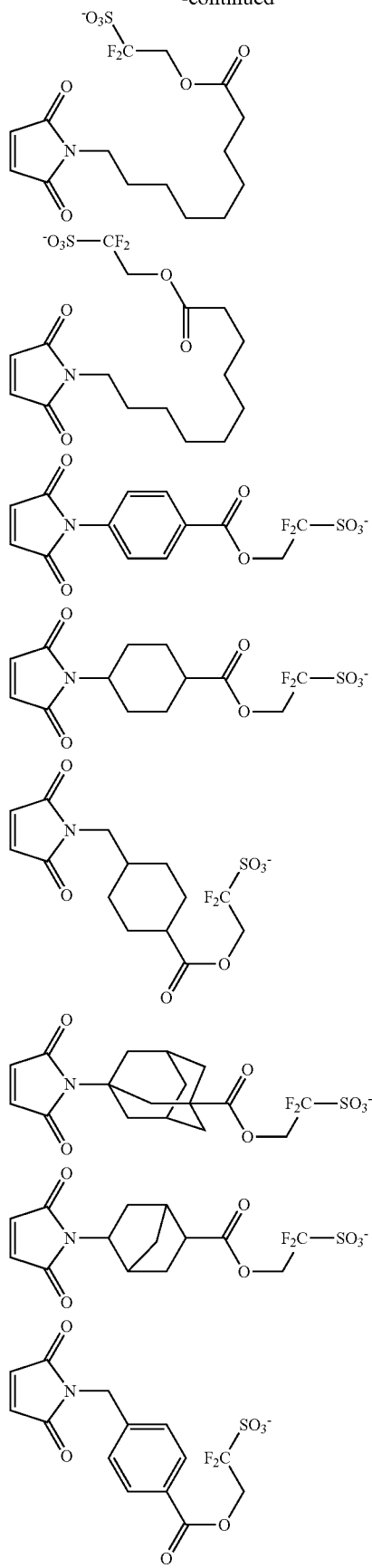
30
-continued
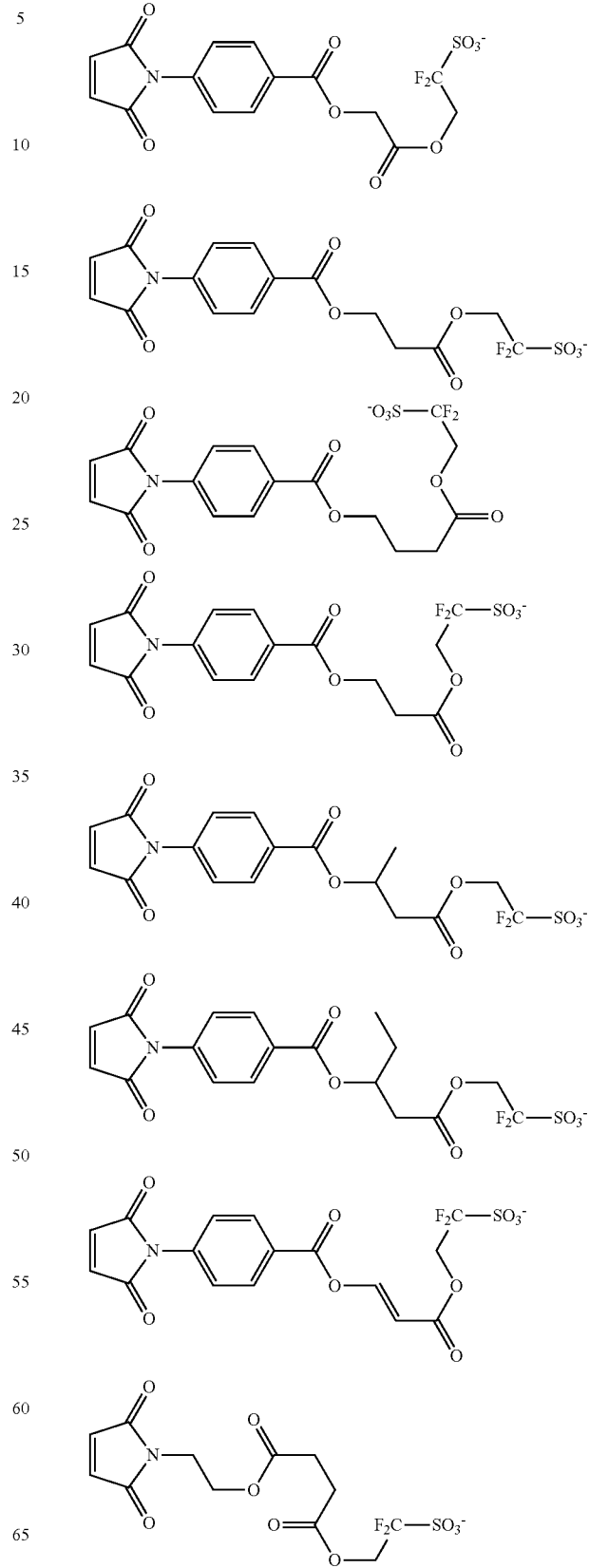

31
-continued
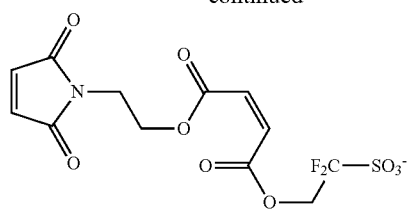
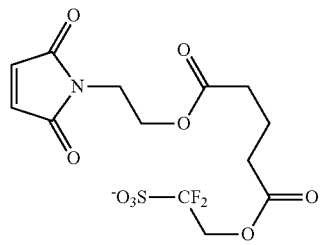
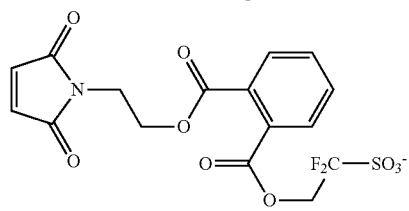
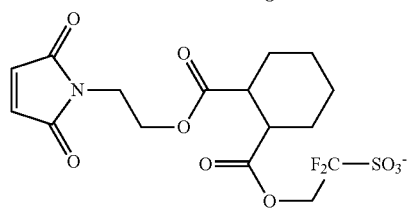
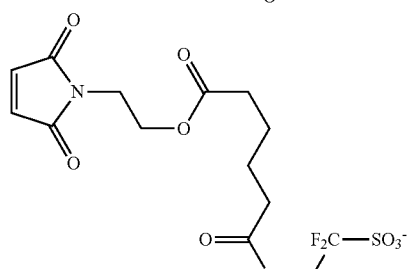
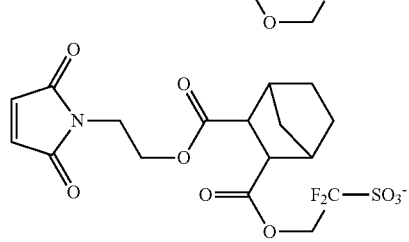
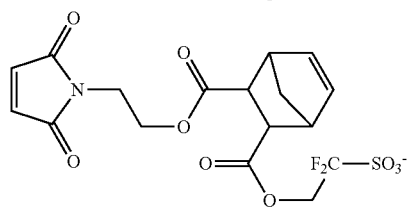
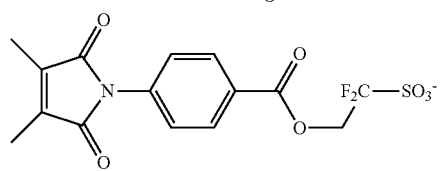
32
-continued
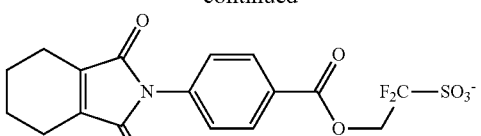
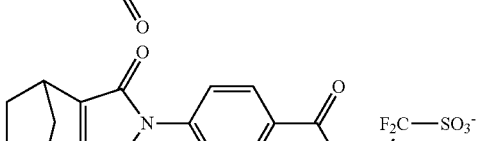
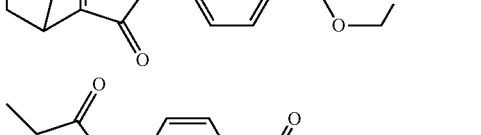
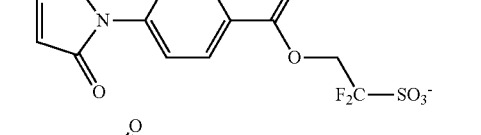
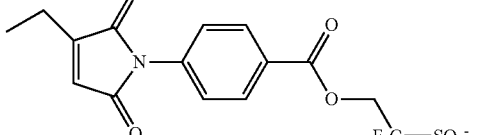
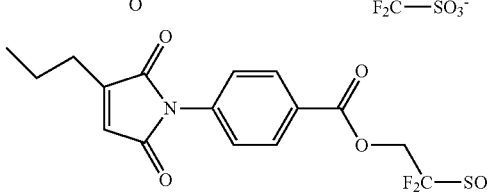
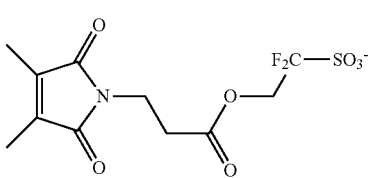
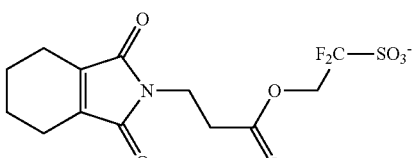
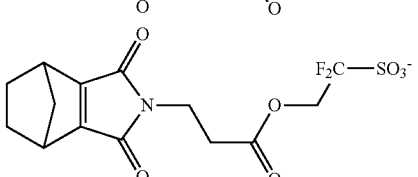
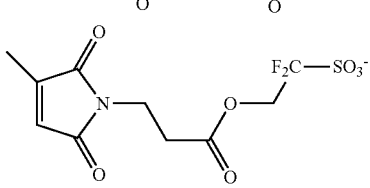
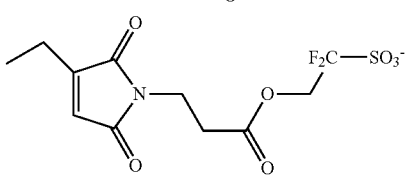

33
-continued
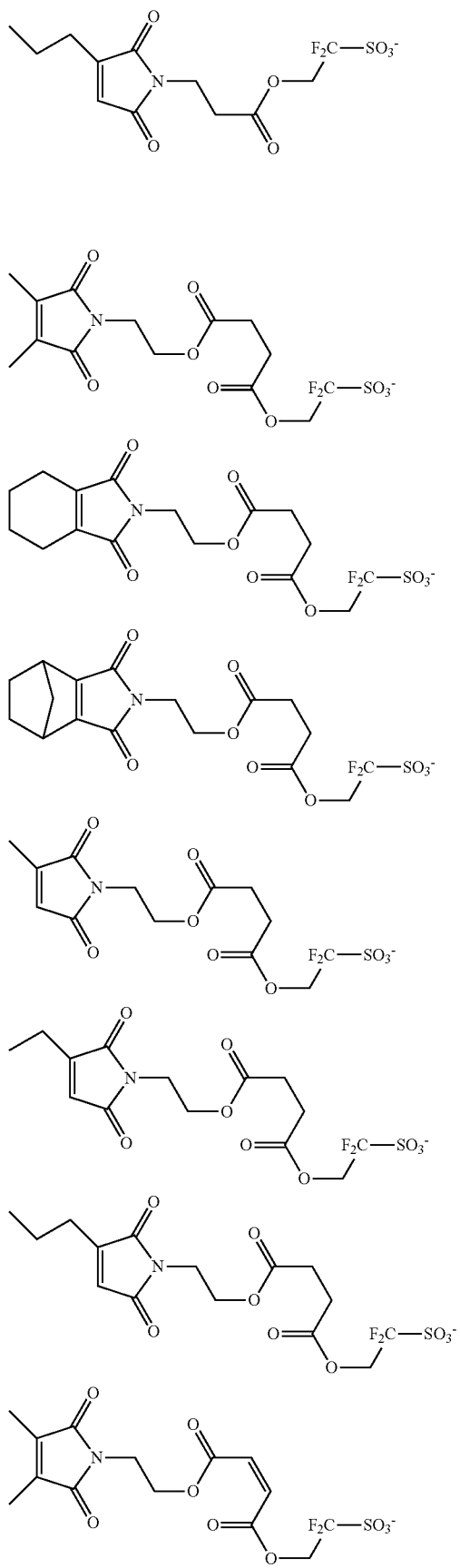
34
-continued
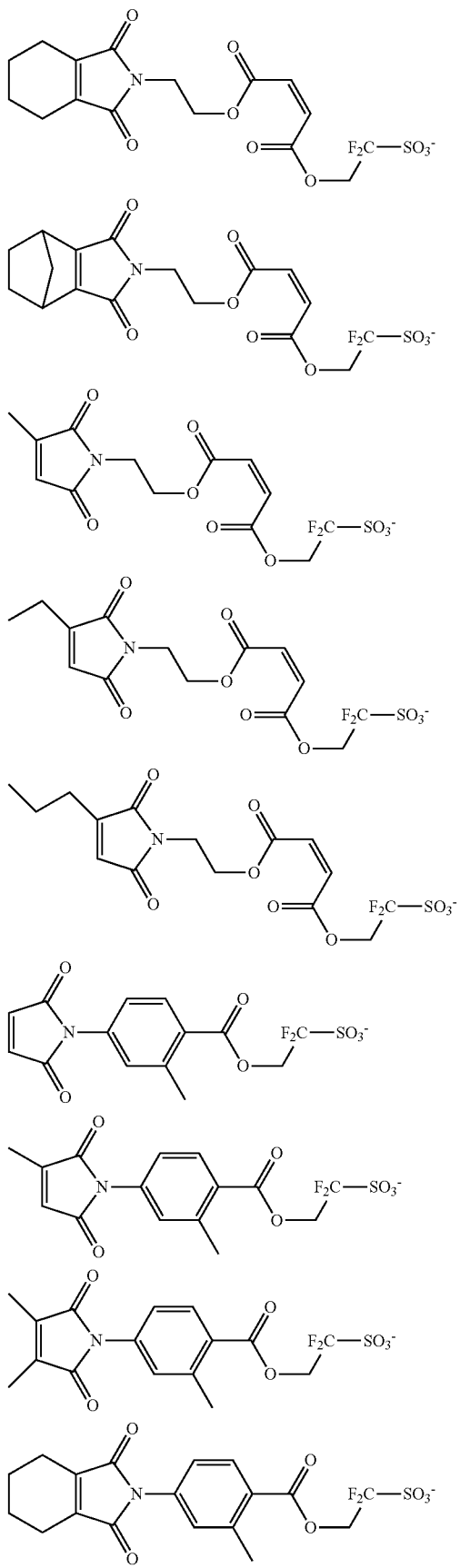

35
-continued
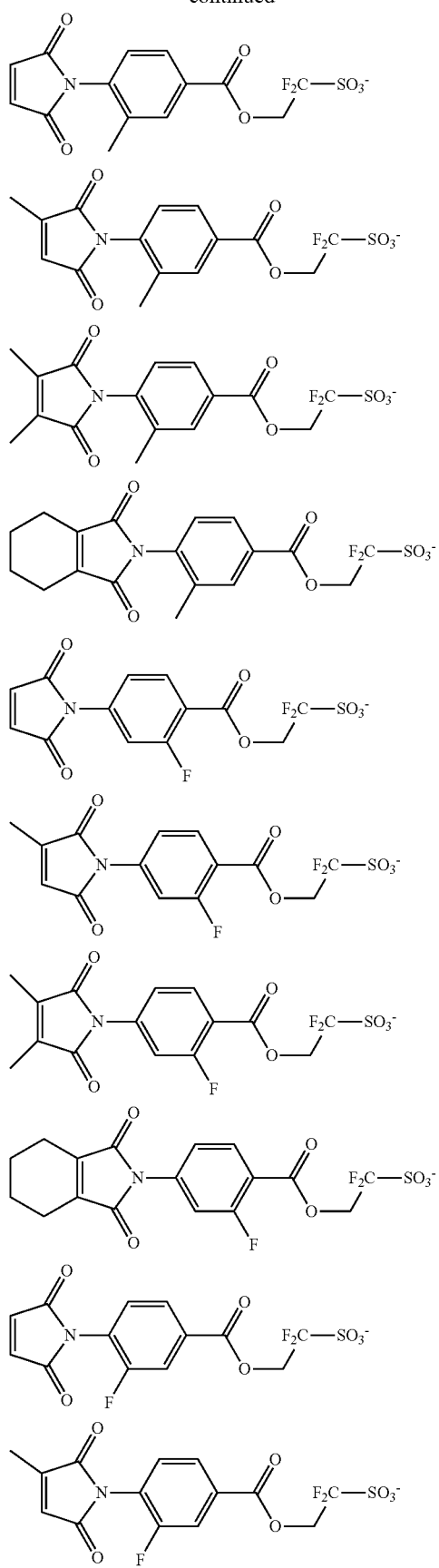
36
-continued
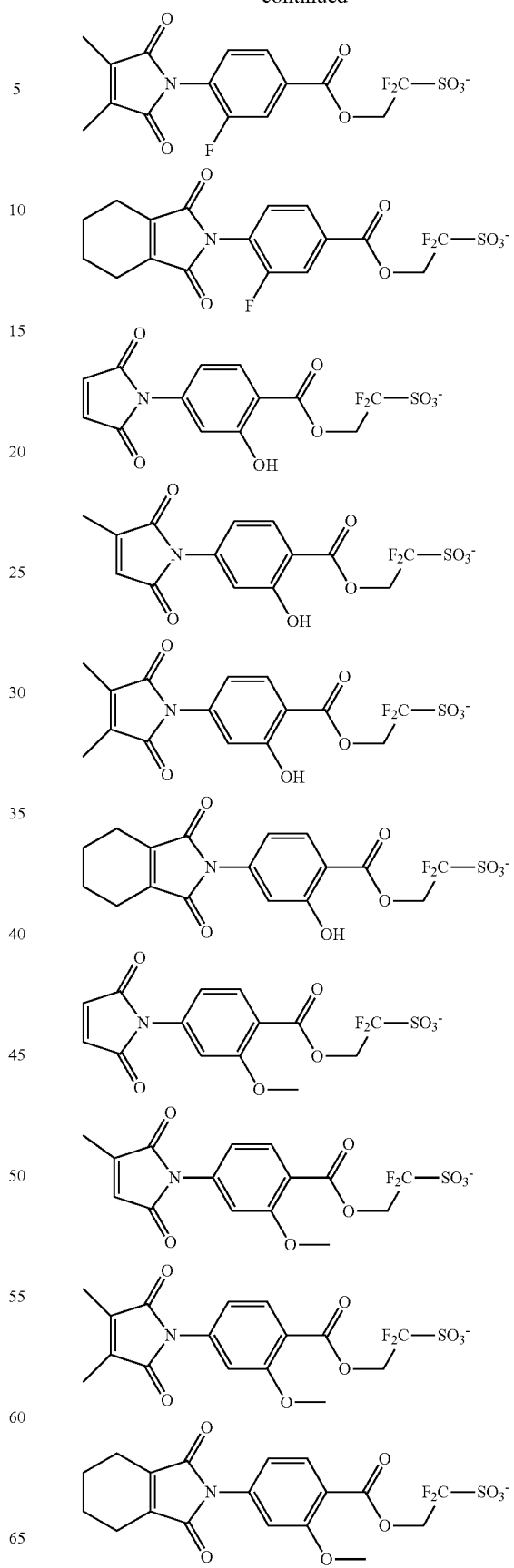

37
-continued
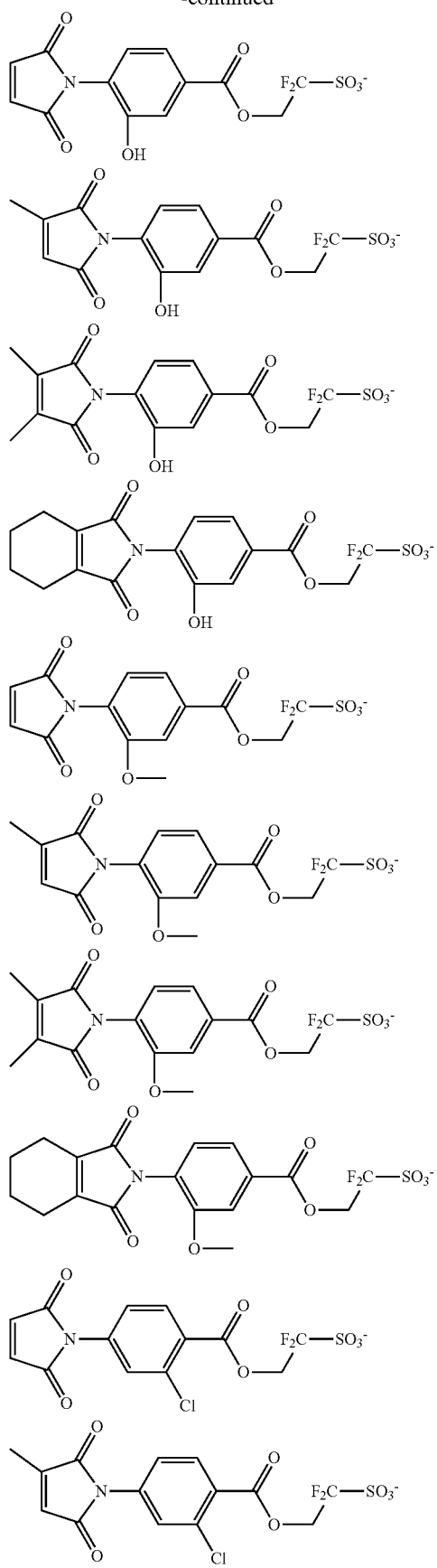
38
-continued
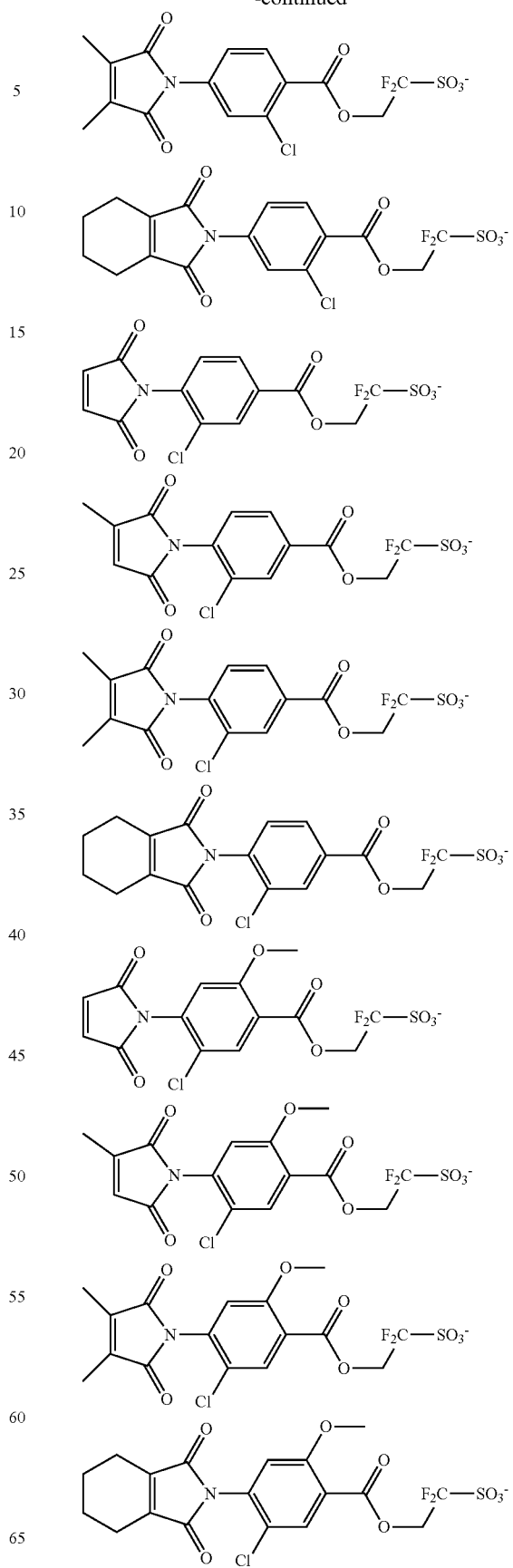

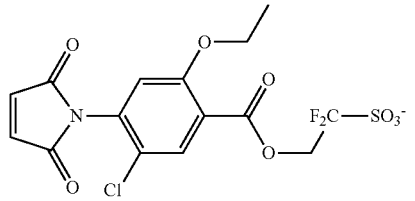
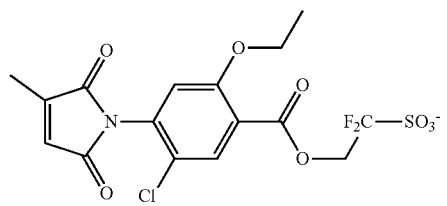
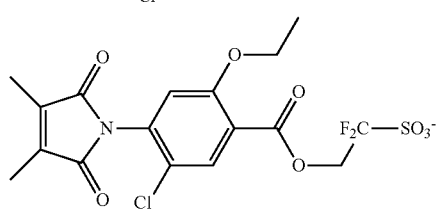
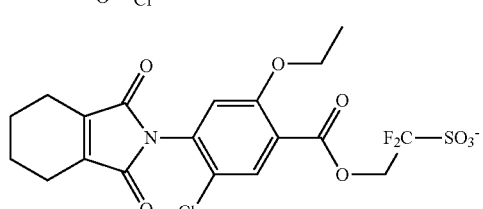
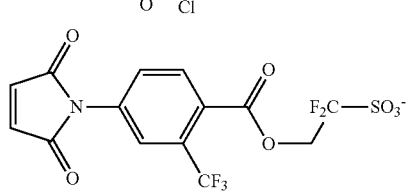
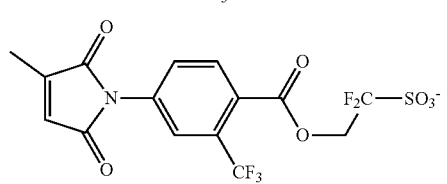
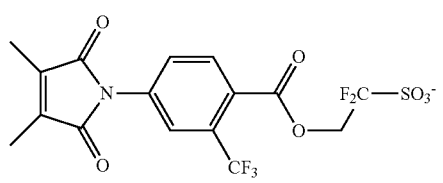
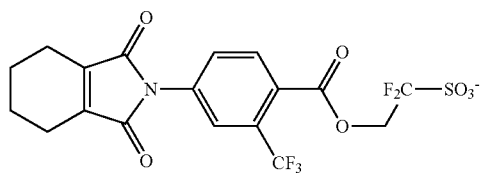
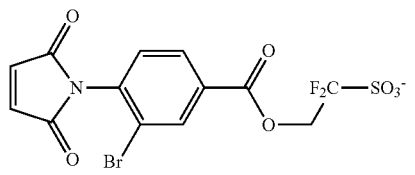
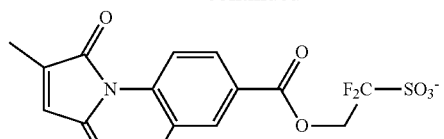
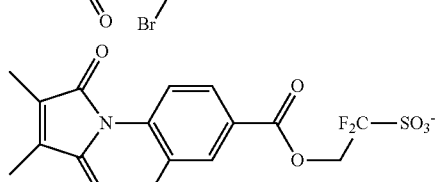
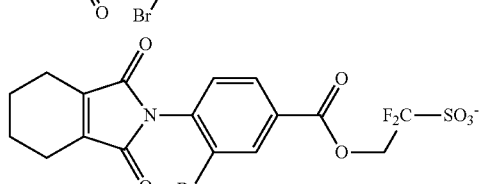
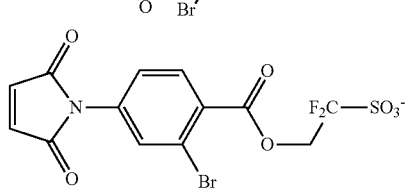
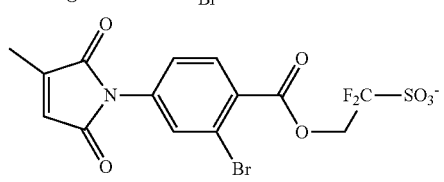
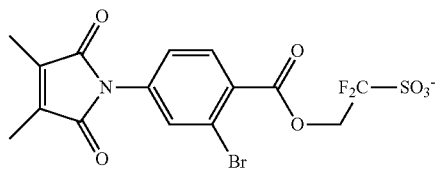
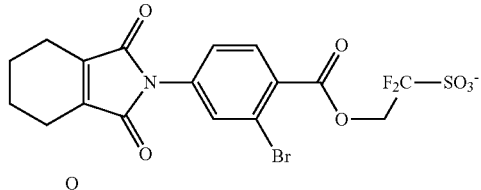
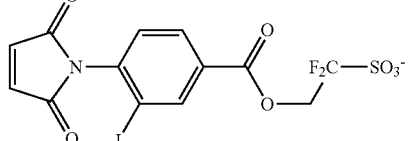
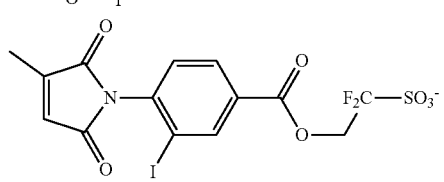
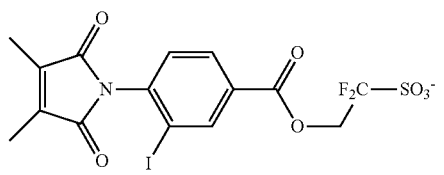

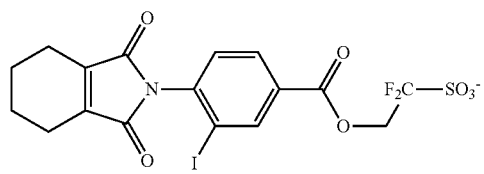
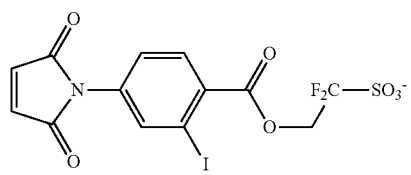
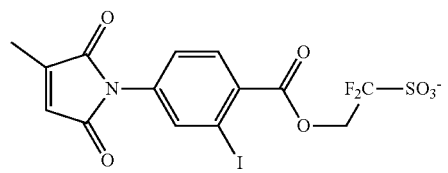
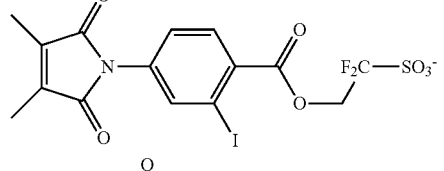
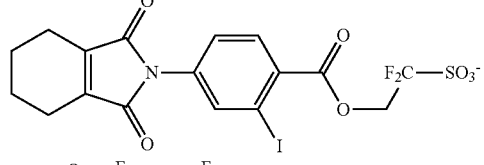
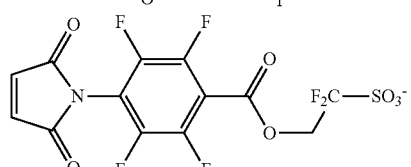
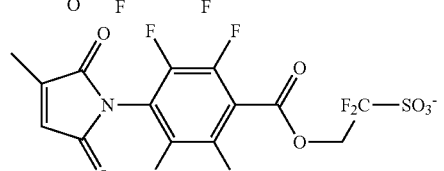
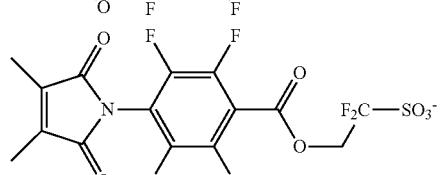
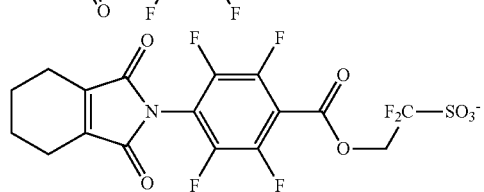
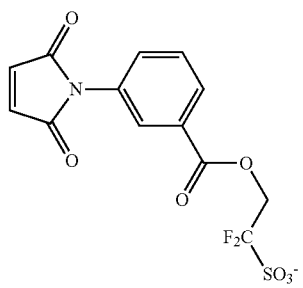
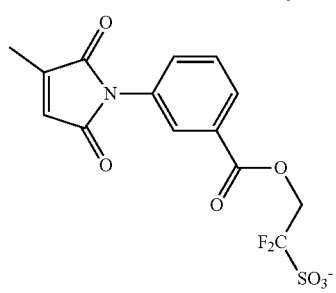
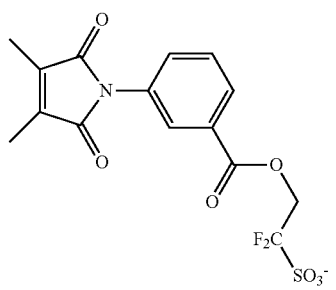
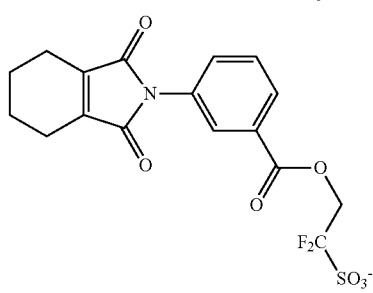
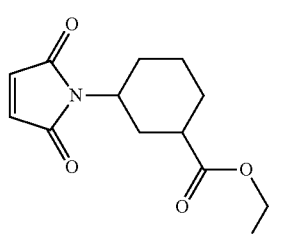
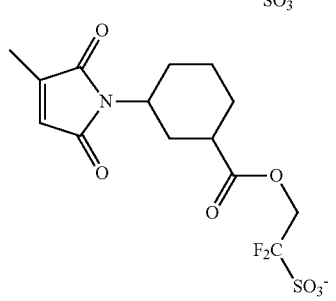

43
-continued
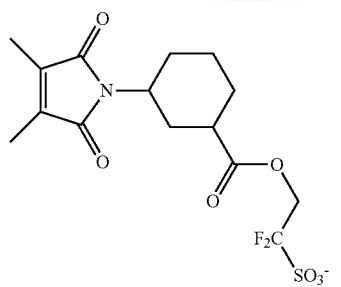
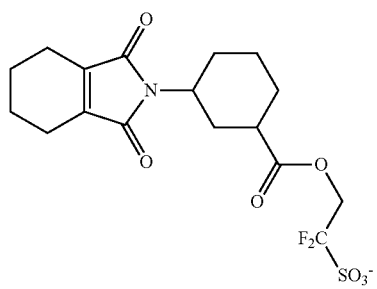
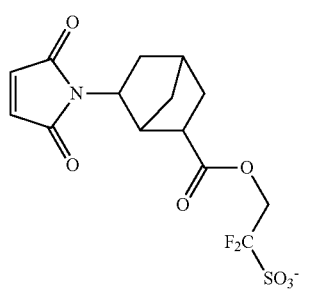
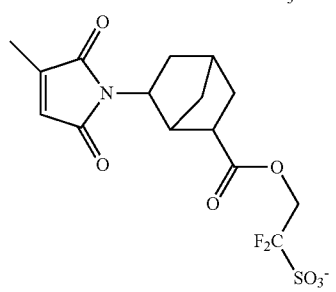
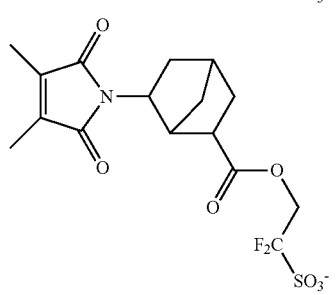
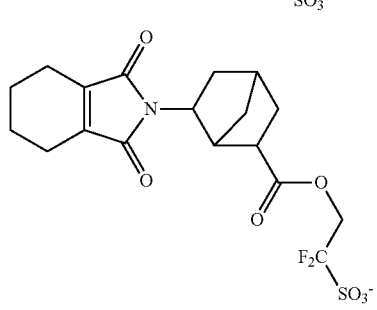
44
-continued
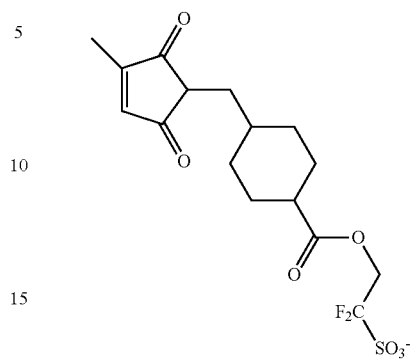
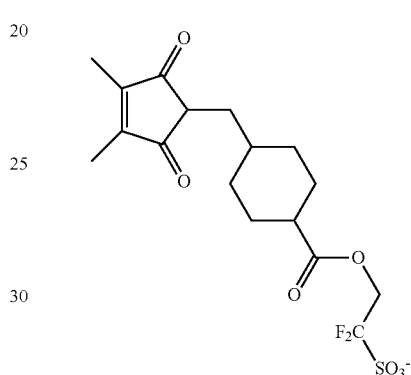
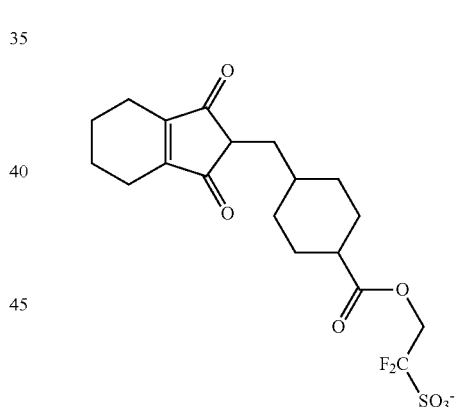
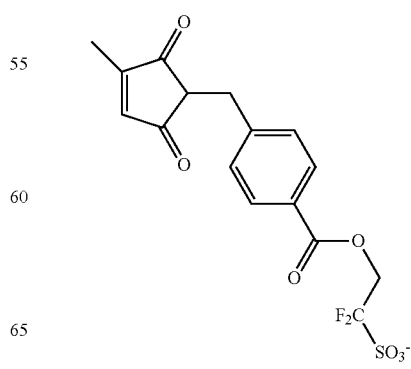

45
-continued
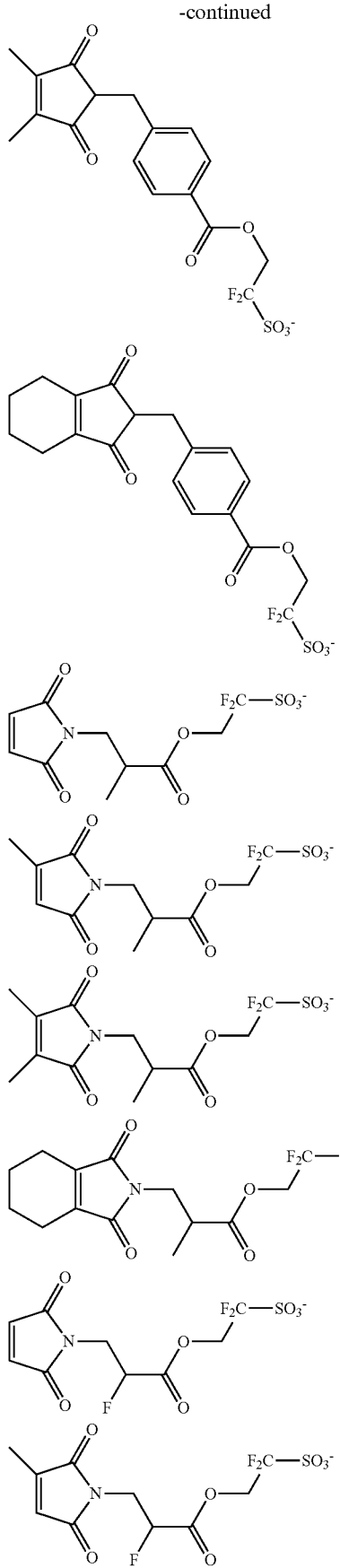
46
-continued
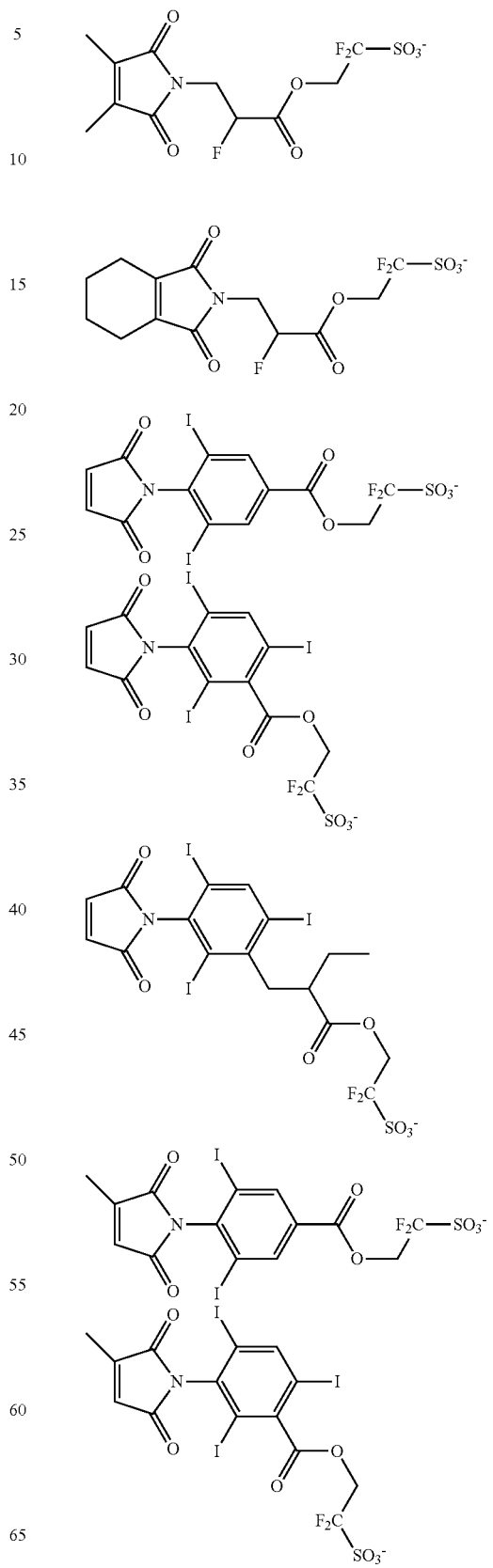

47
-continued
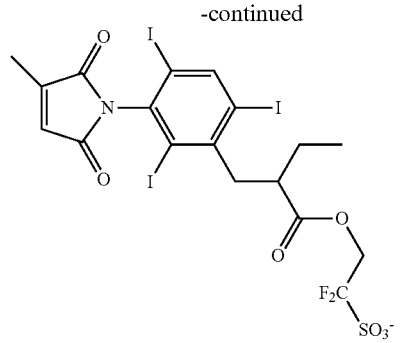
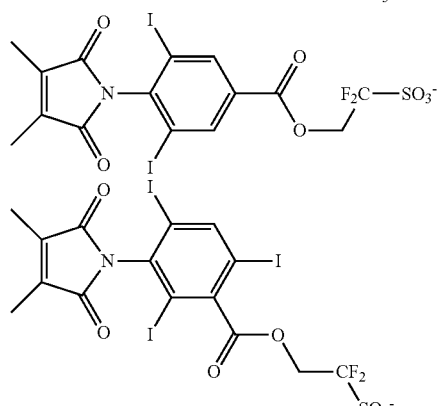
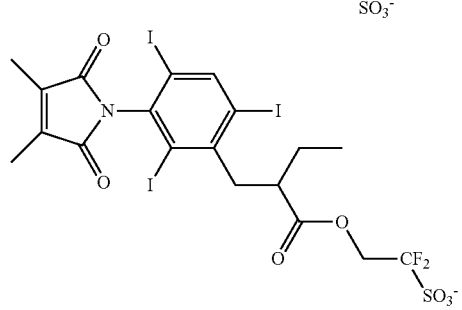
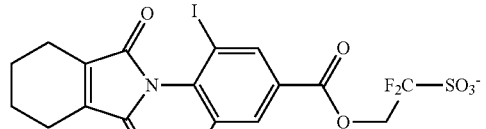
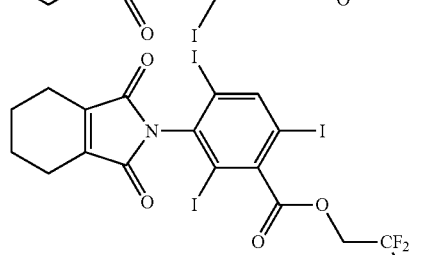
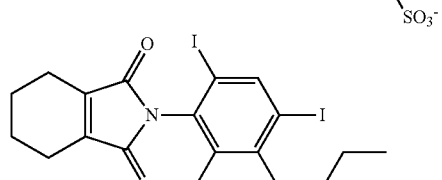
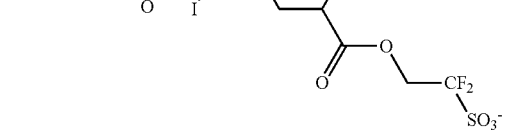
48
-continued
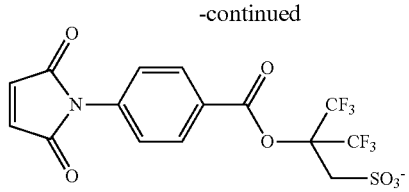
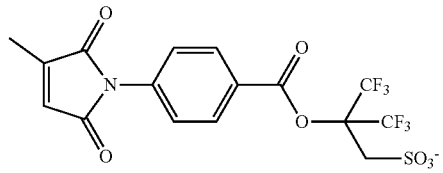
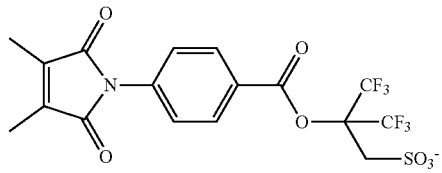
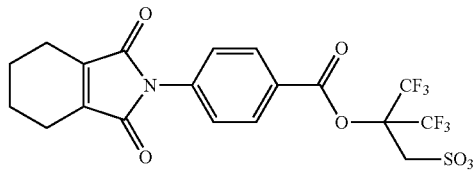
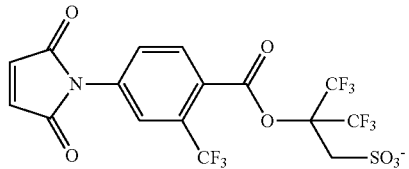
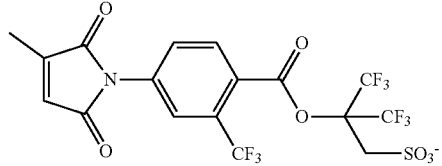
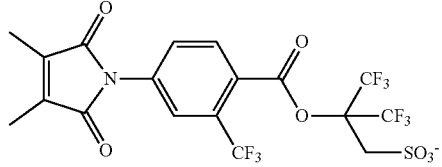
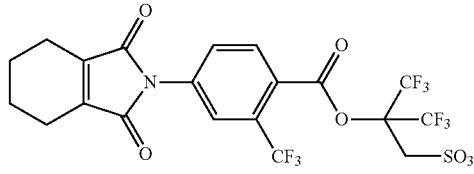
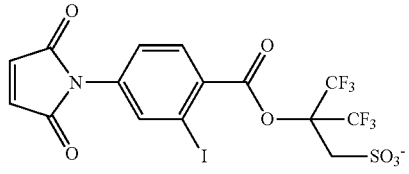
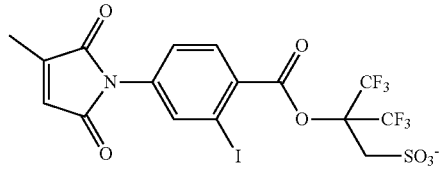

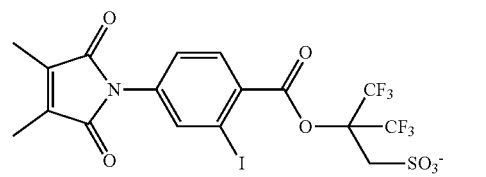
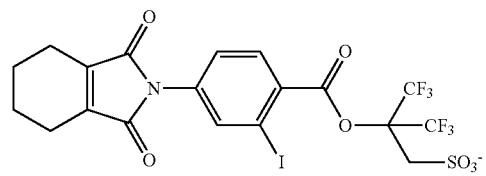
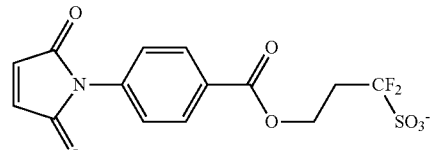
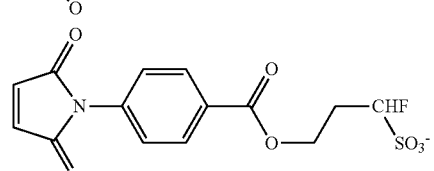
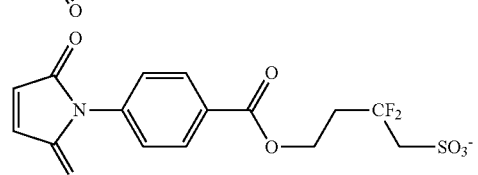
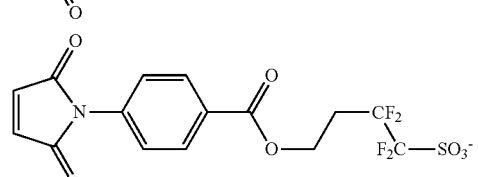
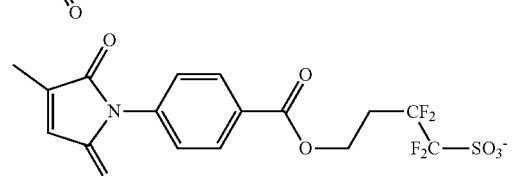
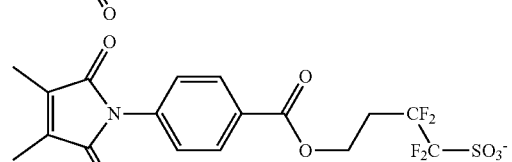
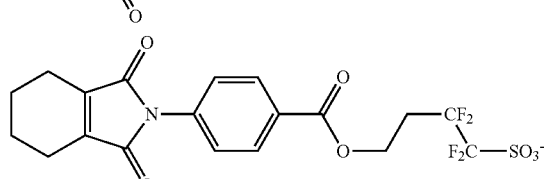
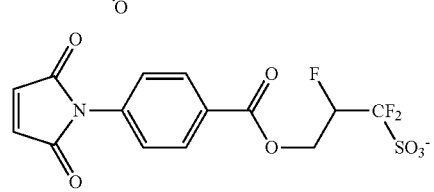
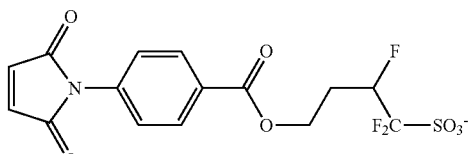
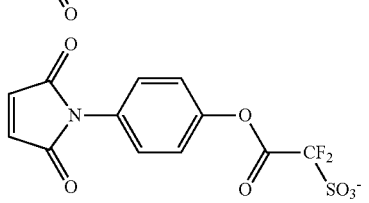
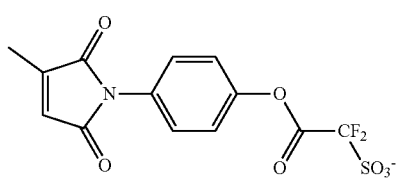
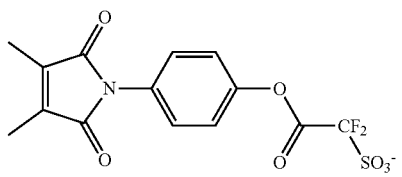
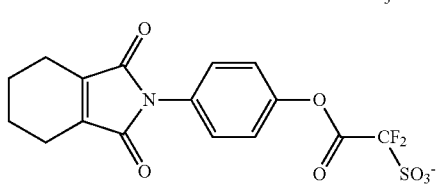
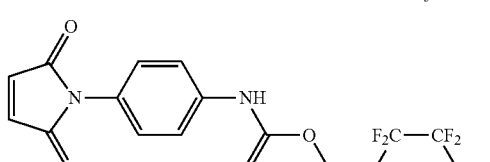
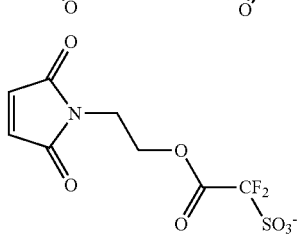
Examples of the sulfonium cation having a polymerizable double bond are shown below, but not limited thereto.
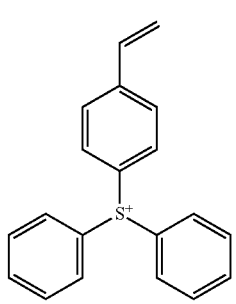

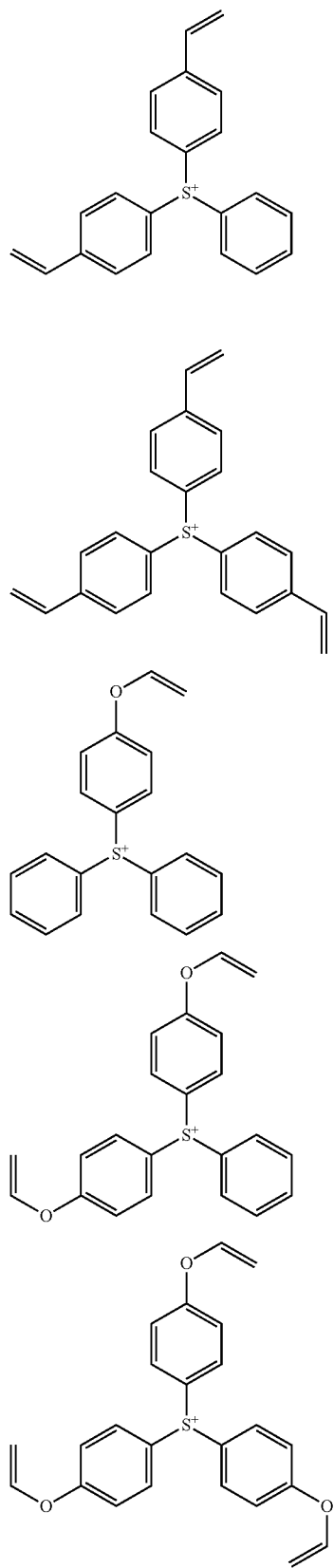
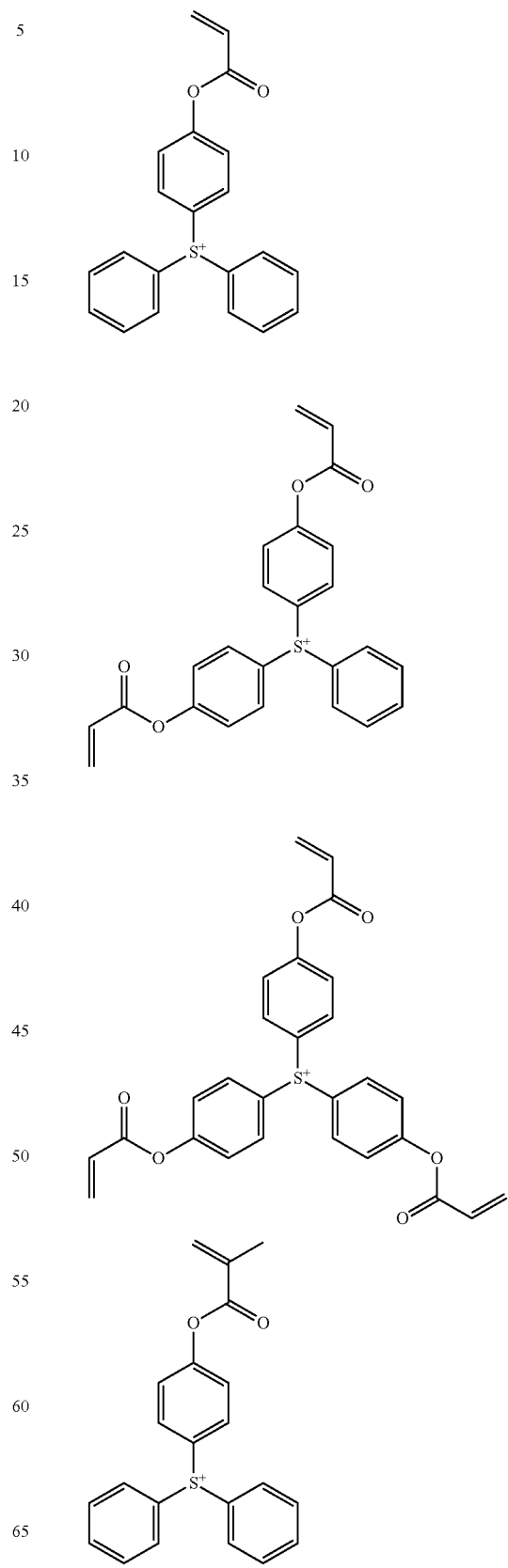

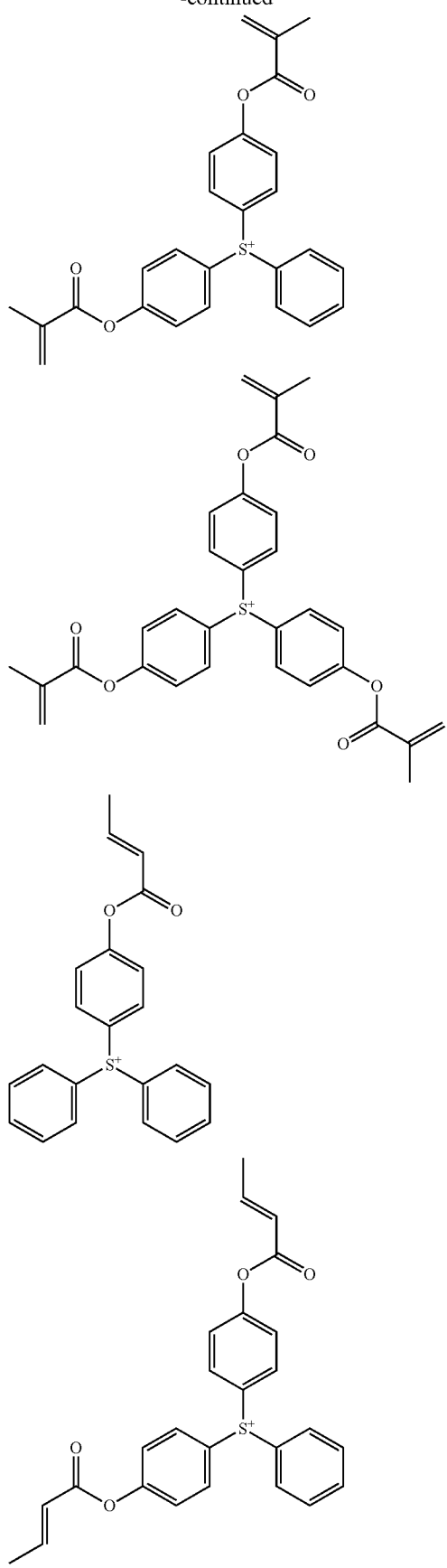
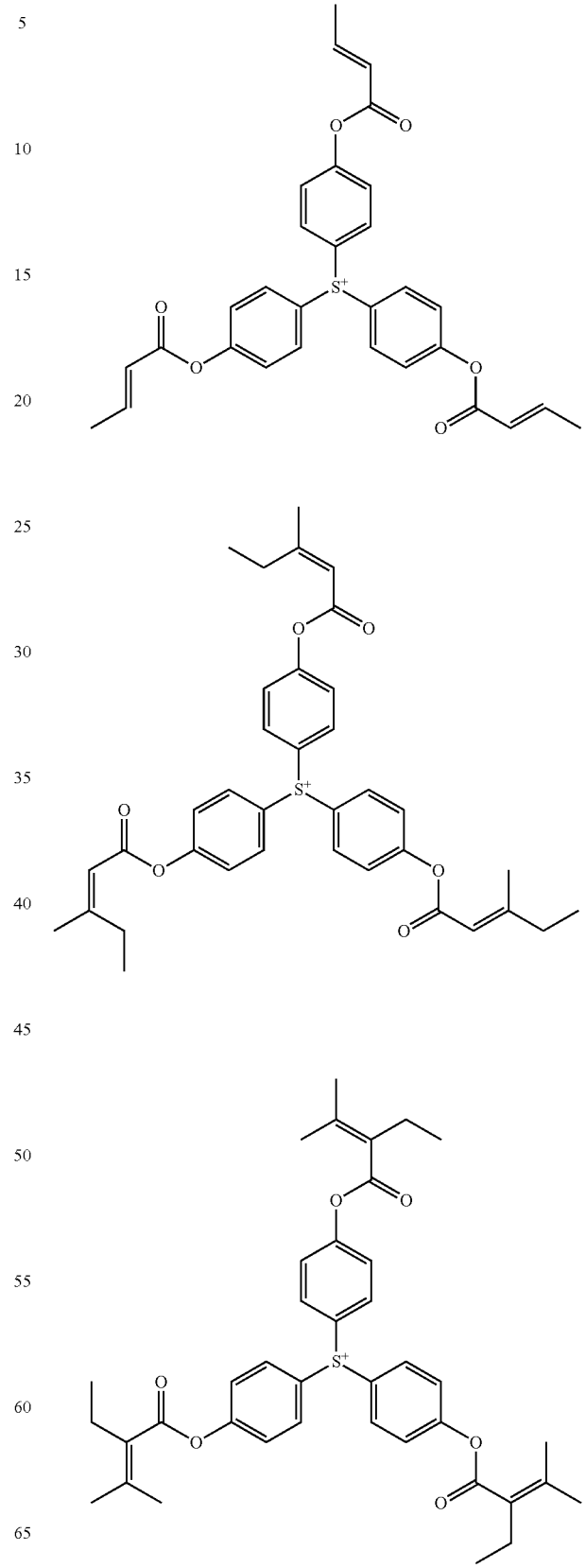

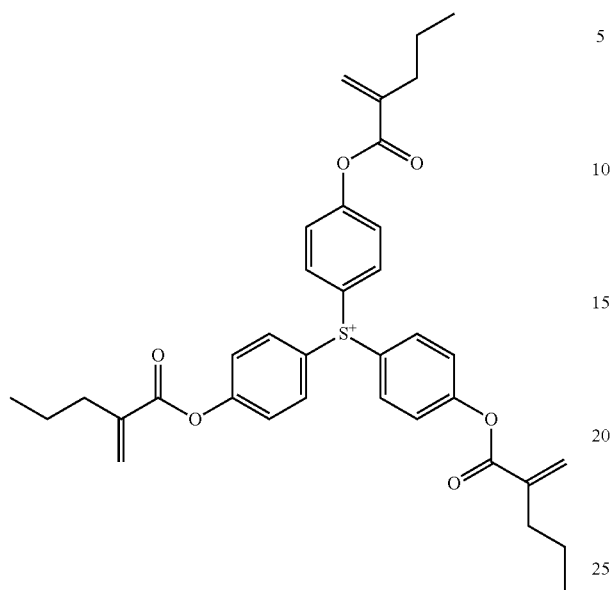
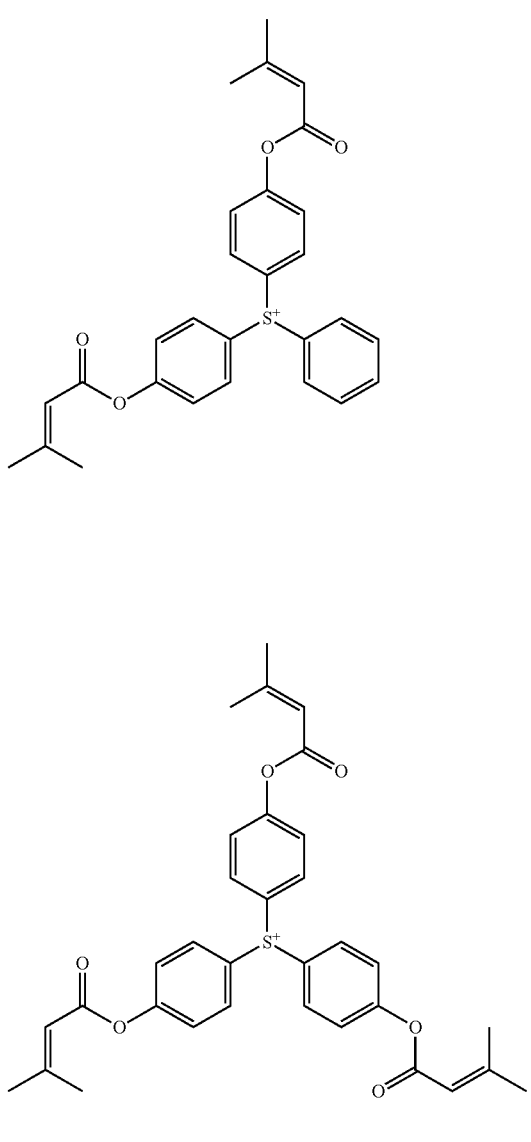
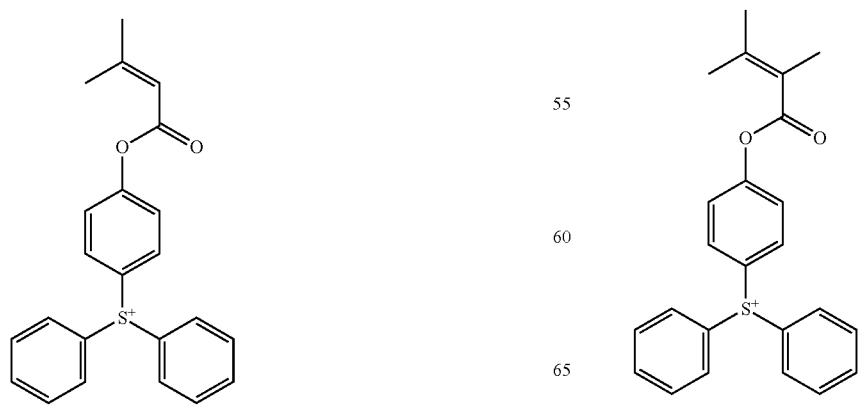

57
-continued
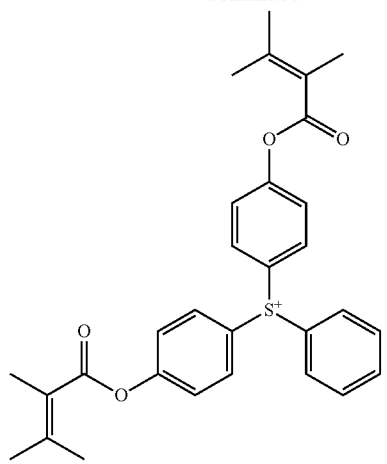
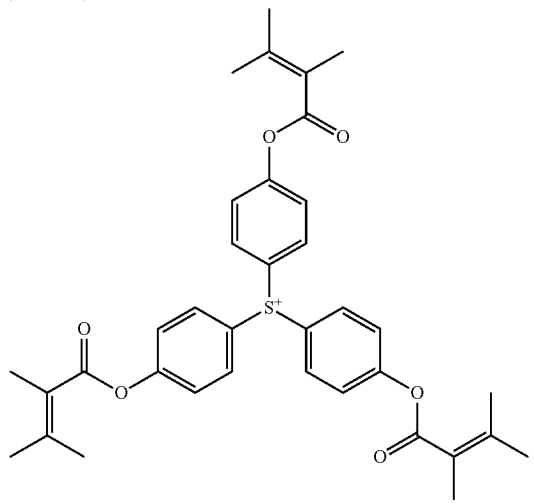
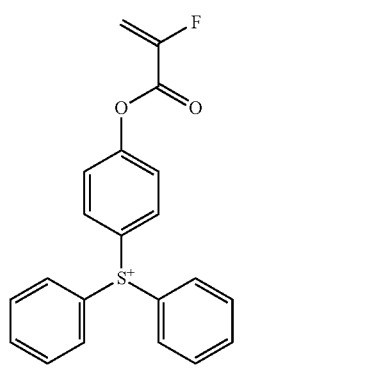
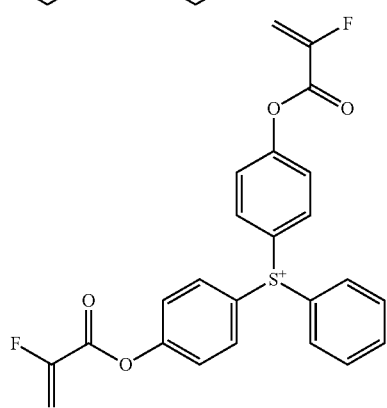
58
-continued
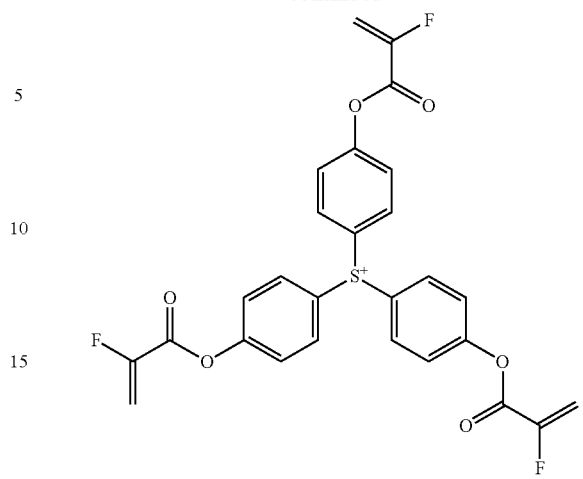
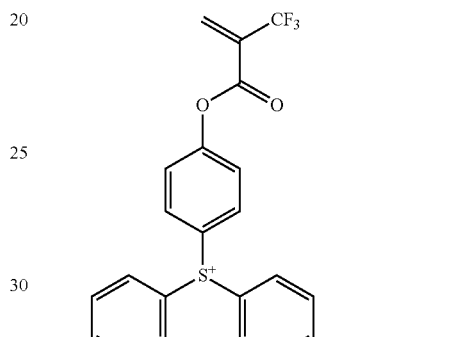
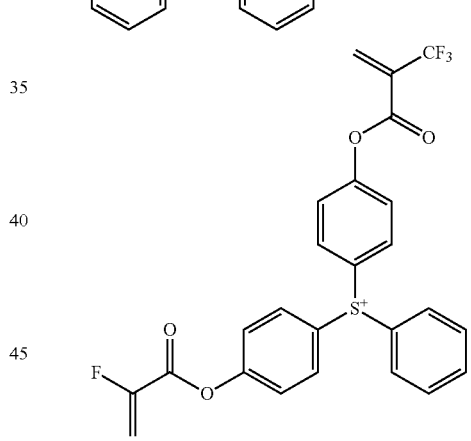
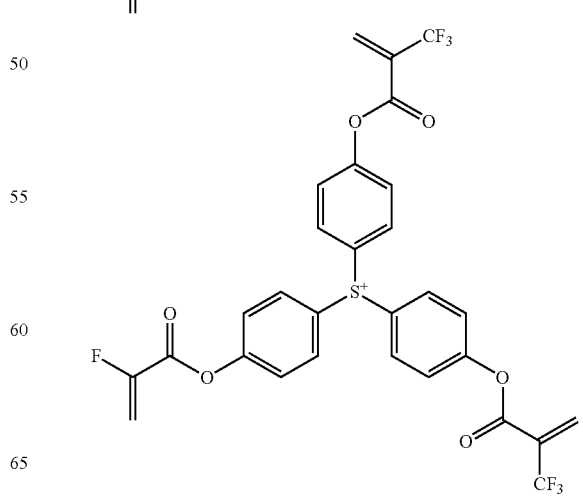

59
-continued
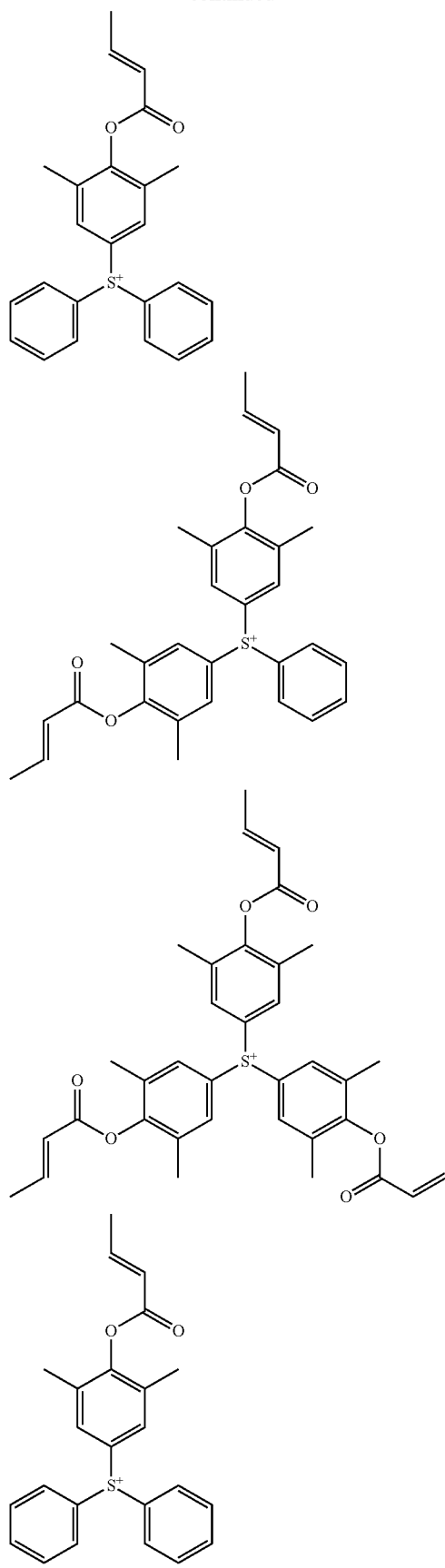
60
-continued
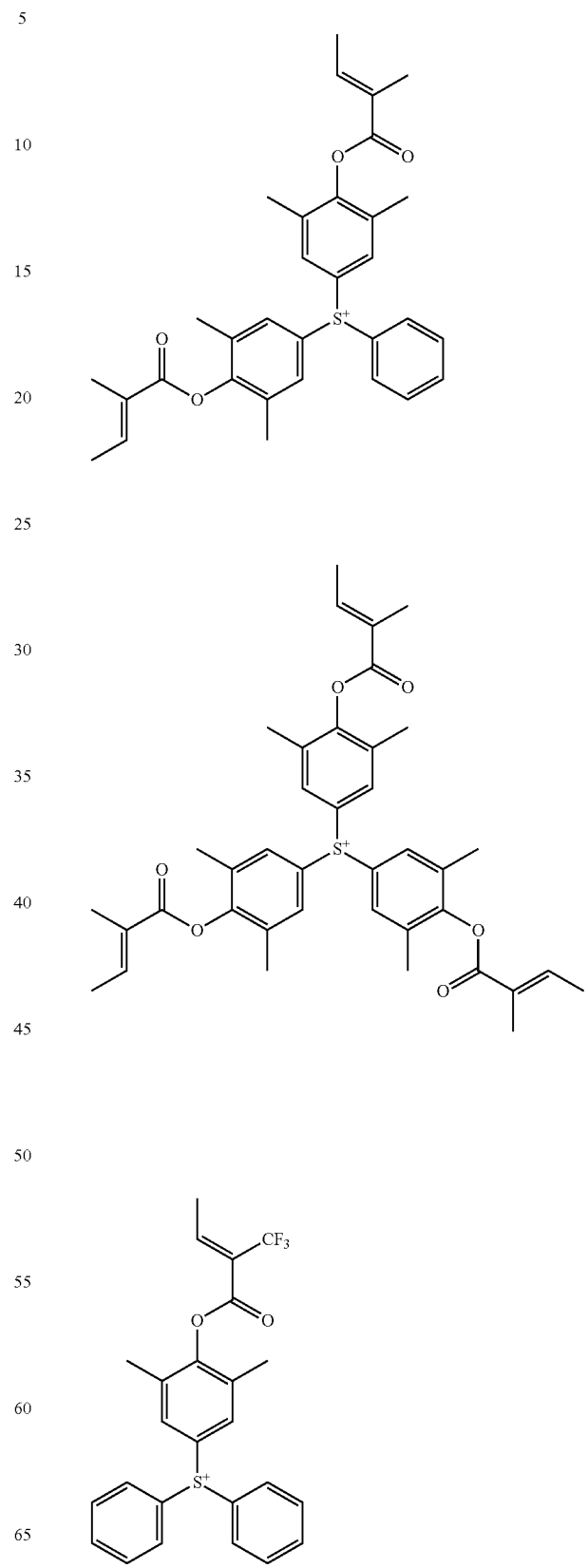

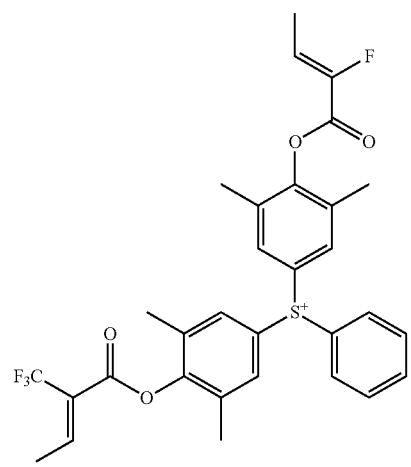
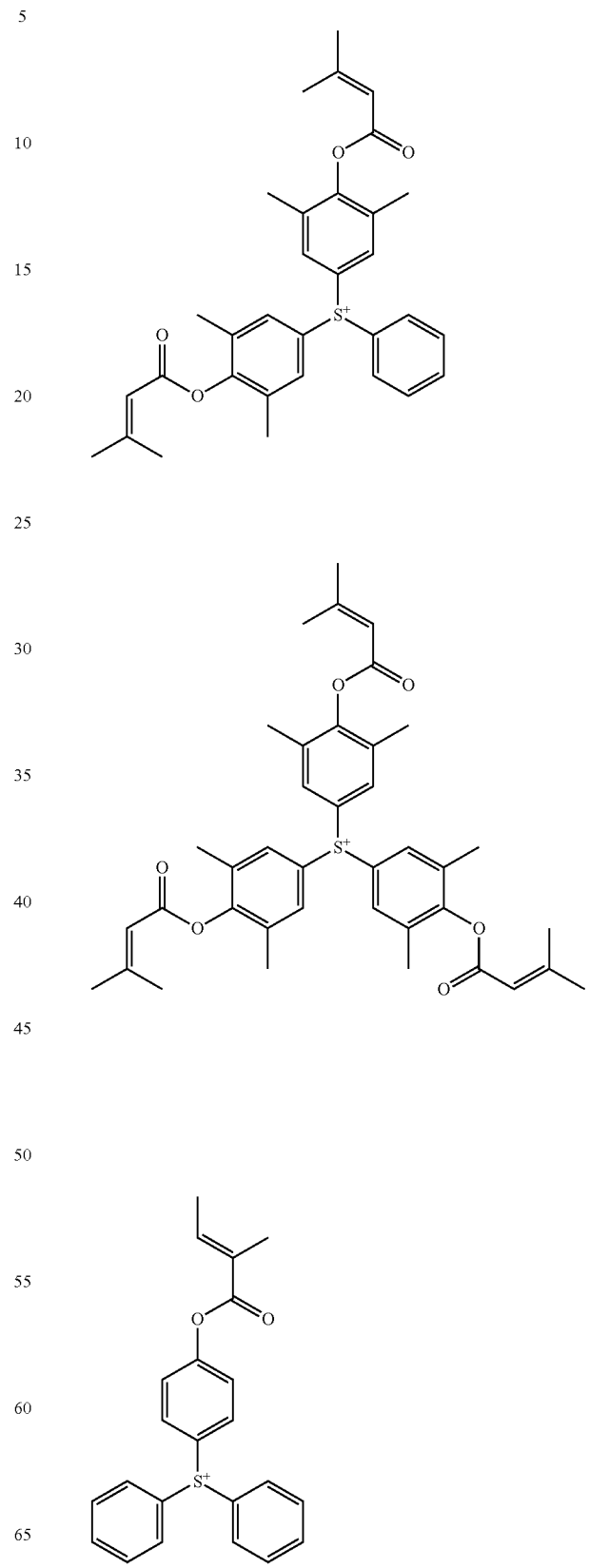

-continued
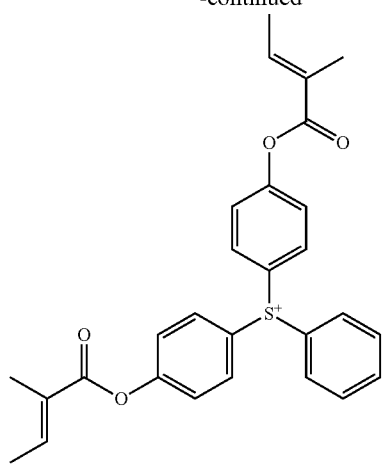
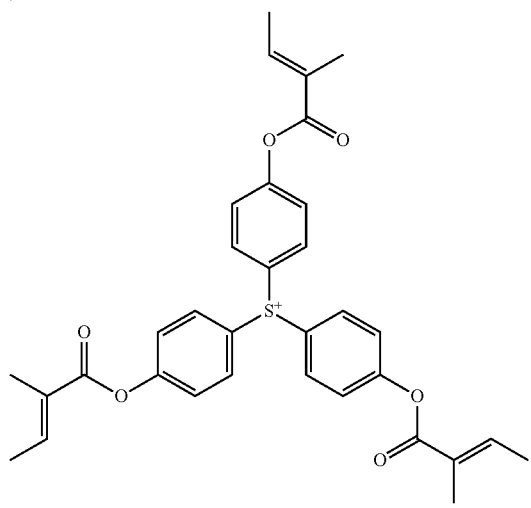
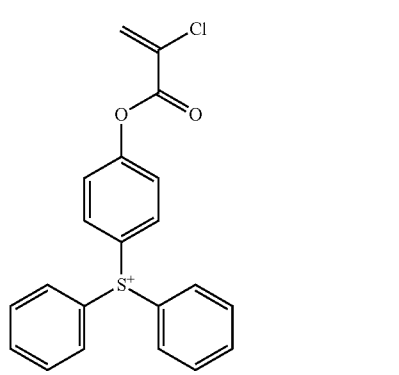
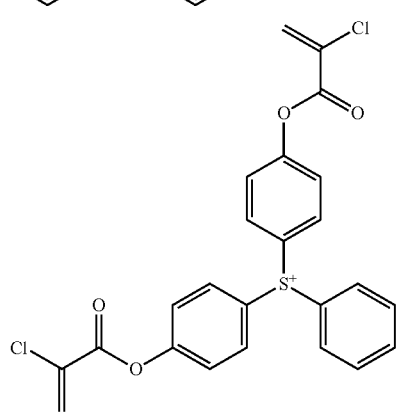
-continued
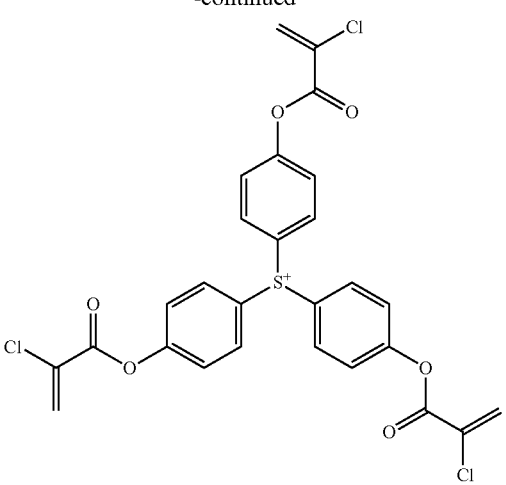
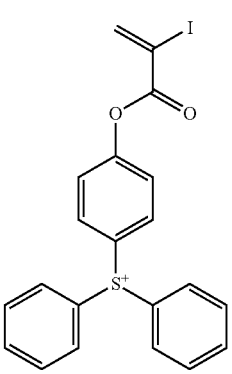
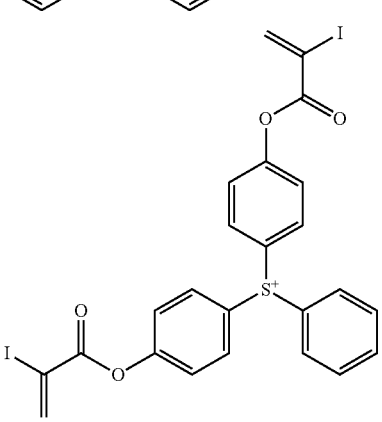
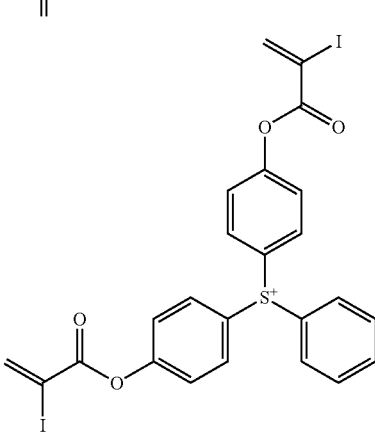

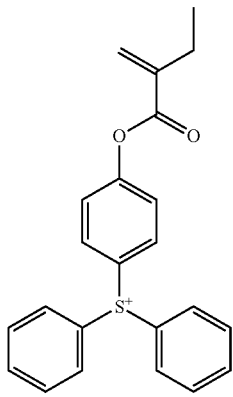
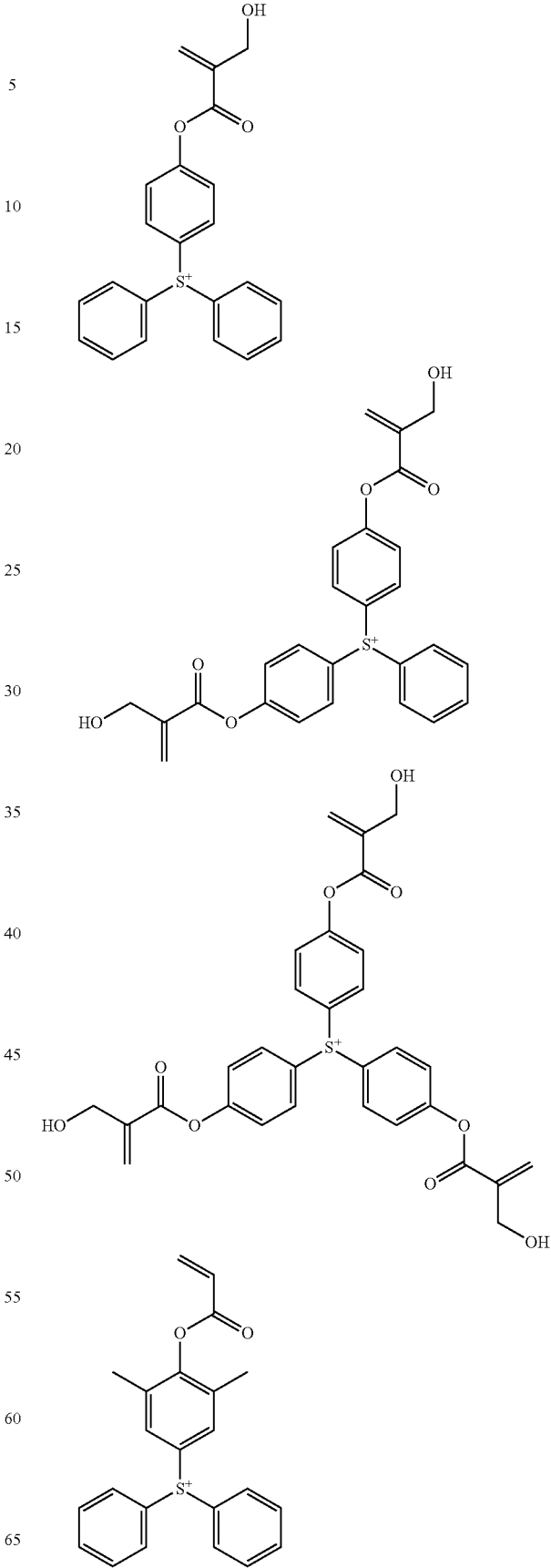

67
-continued
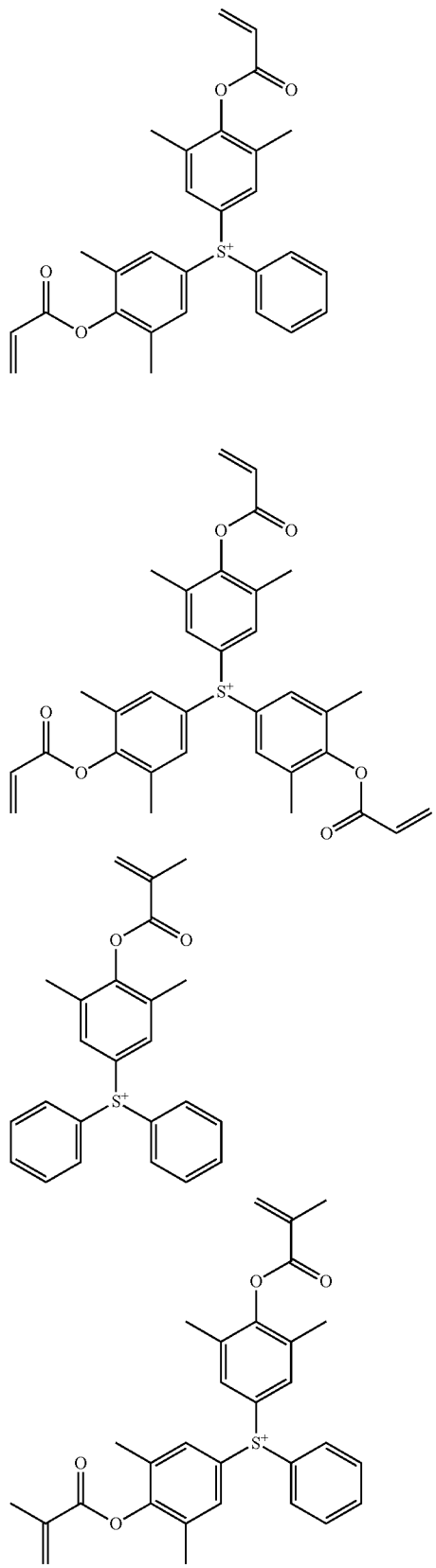
68
-continued
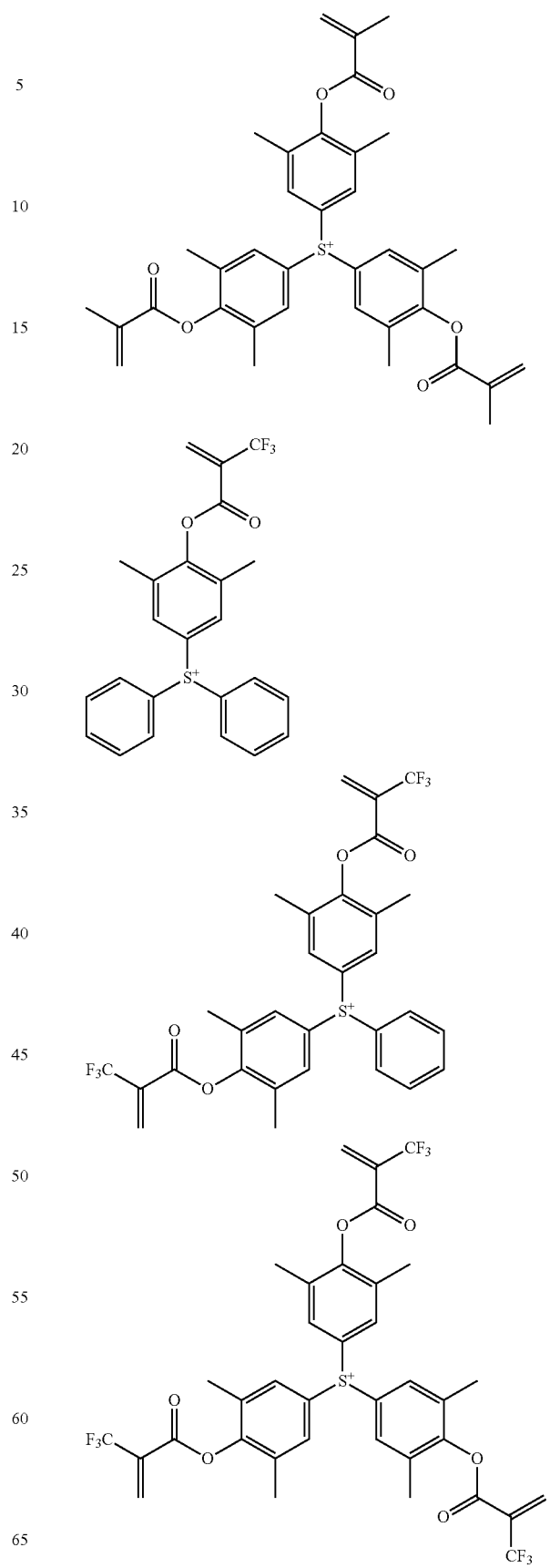

69
-continued
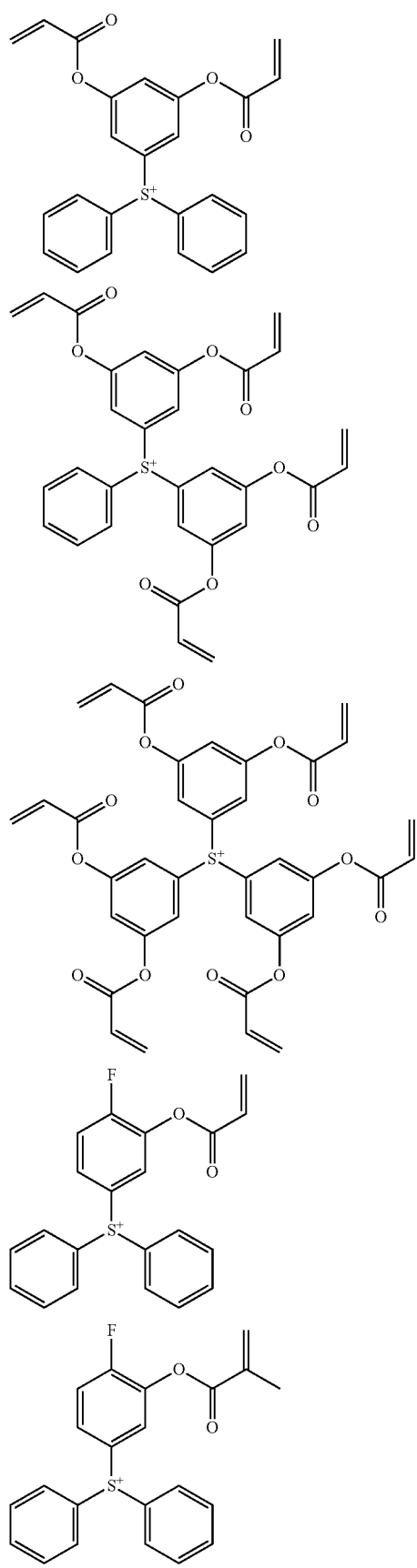
70
-continued
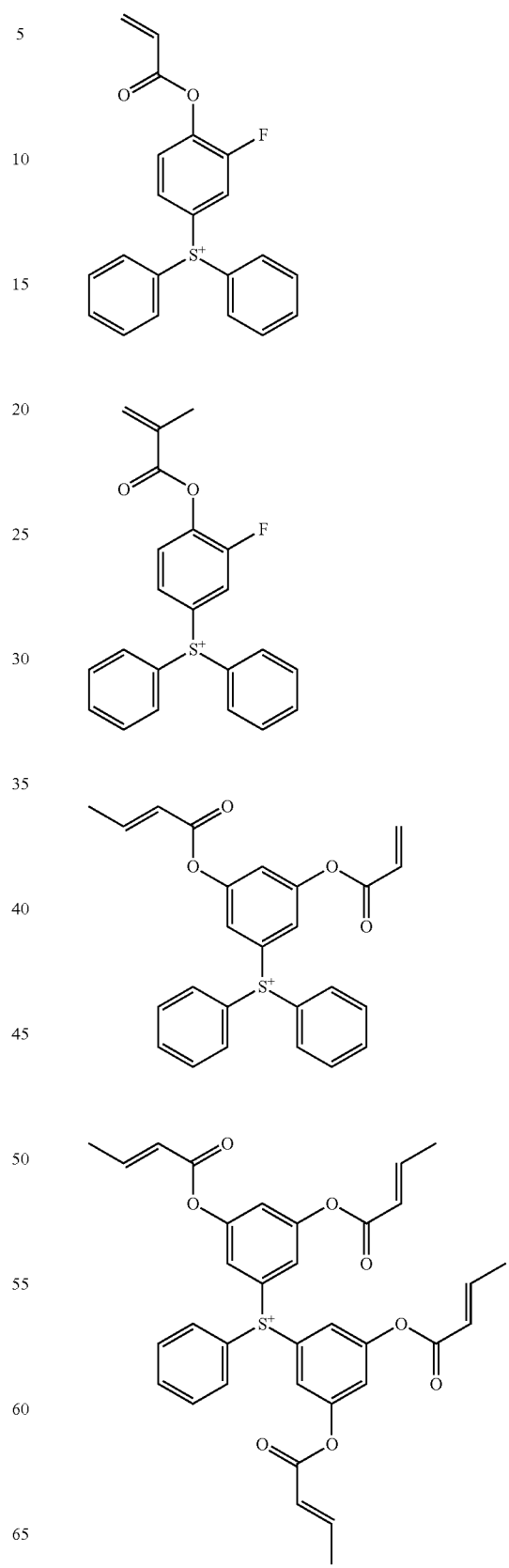

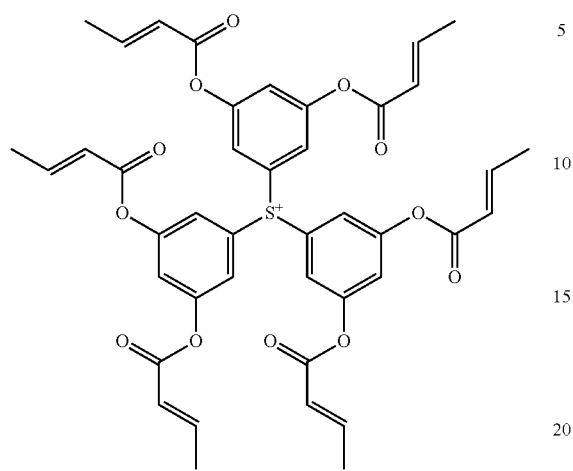
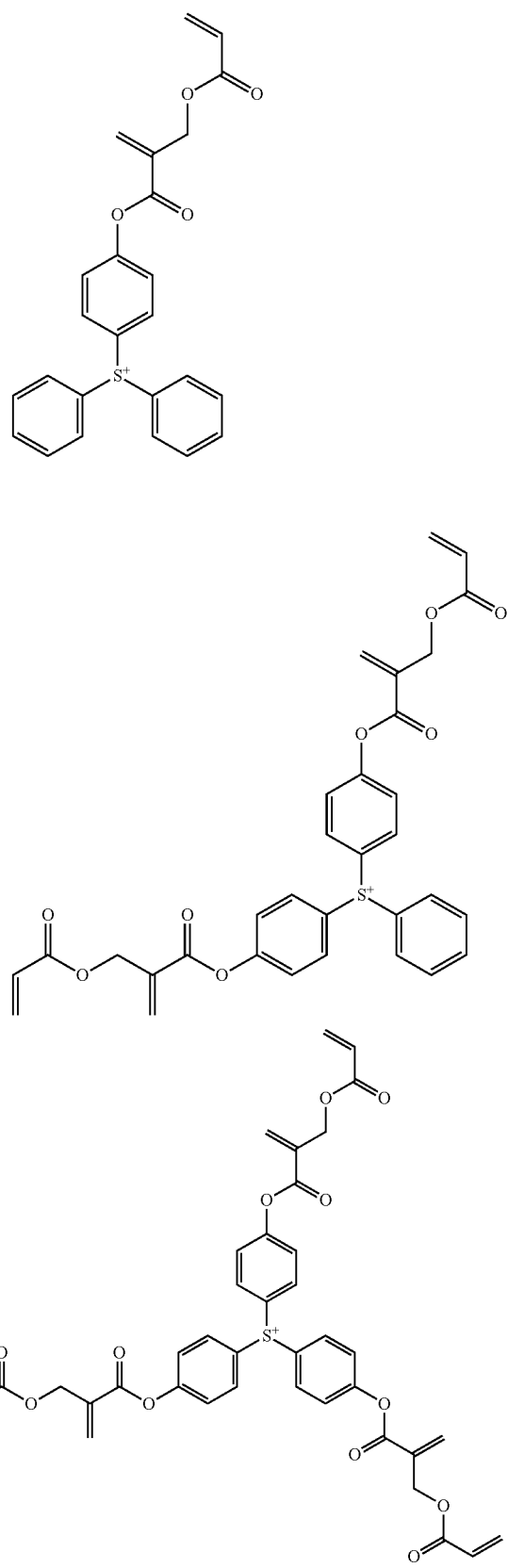

73
-continued
74
-continued
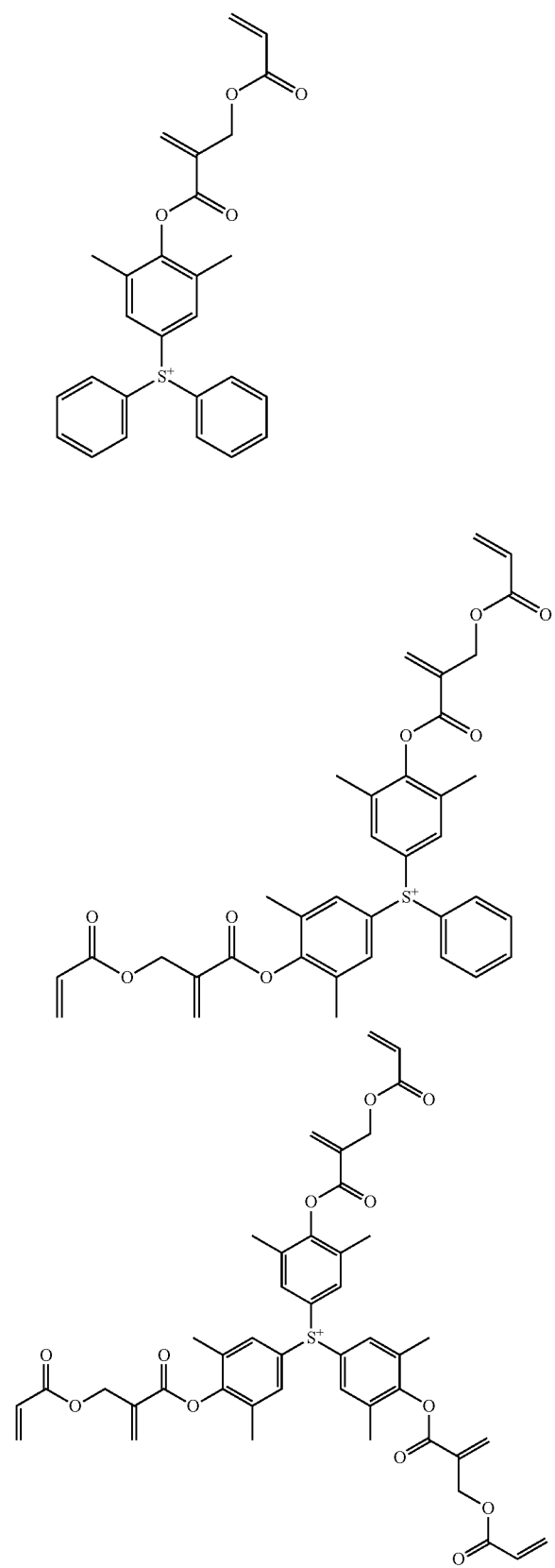 [SMILES: C=CC(=O)OCC(=C)C(=O)Oc1c(C)cc([S+](c2ccccc2)c2ccccc2)cc1C ; C=CC(=O)OCC(=C)C(=O)Oc1c(C)cc([S+](c2ccccc2)c2cc(C)c(OC(=O)C(=C)COC(=O)C=C)c(C)c2)cc1C ; C=CC(=O)OCC(=C)C(=O)Oc1c(C)cc([S+](c2cc(C)c(OC(=O)C(=C)COC(=O)C=C)c(C)c2)c2cc(C)c(OC(=O)C(=C)COC(=O)C=C)c(C)c2)cc1C]
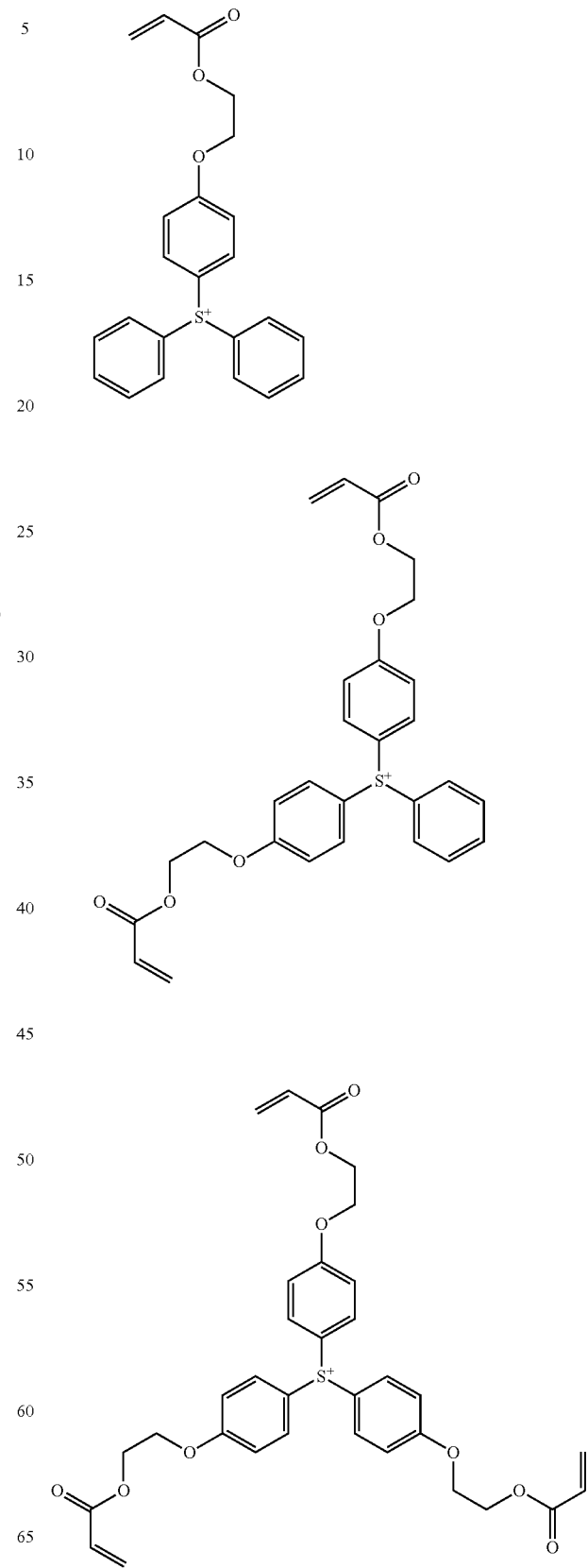

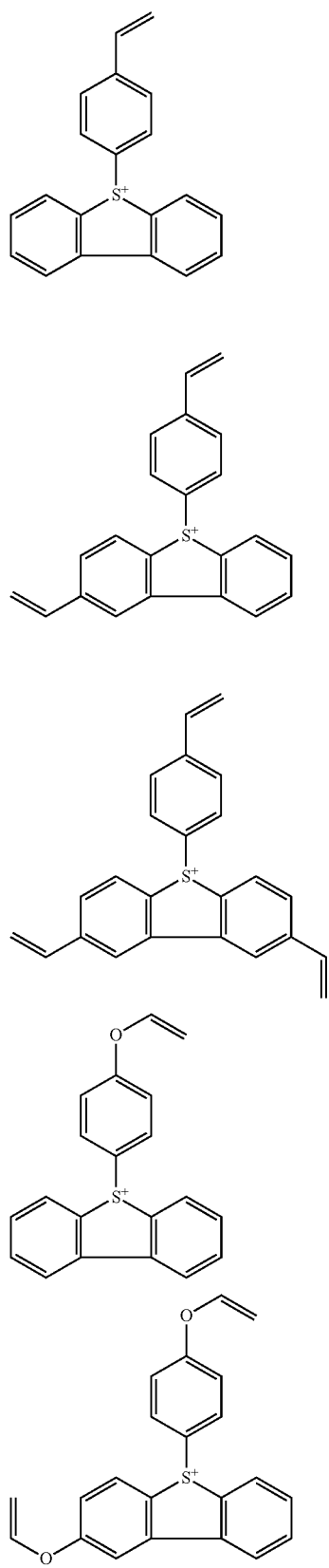
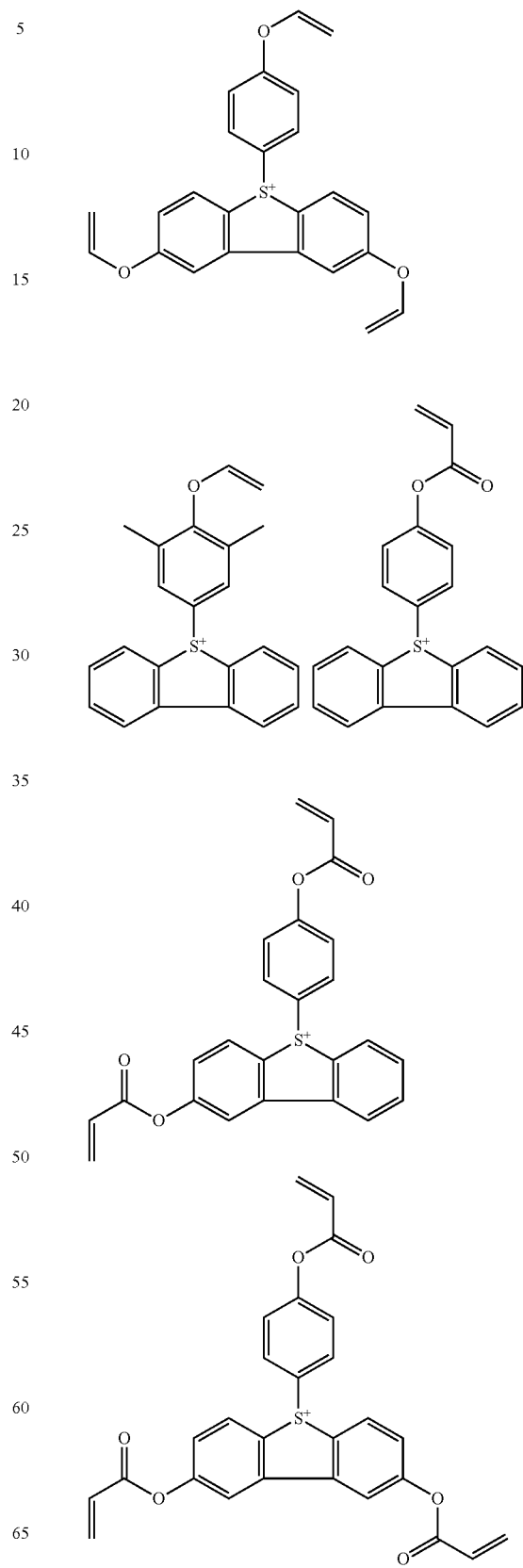

77
-continued
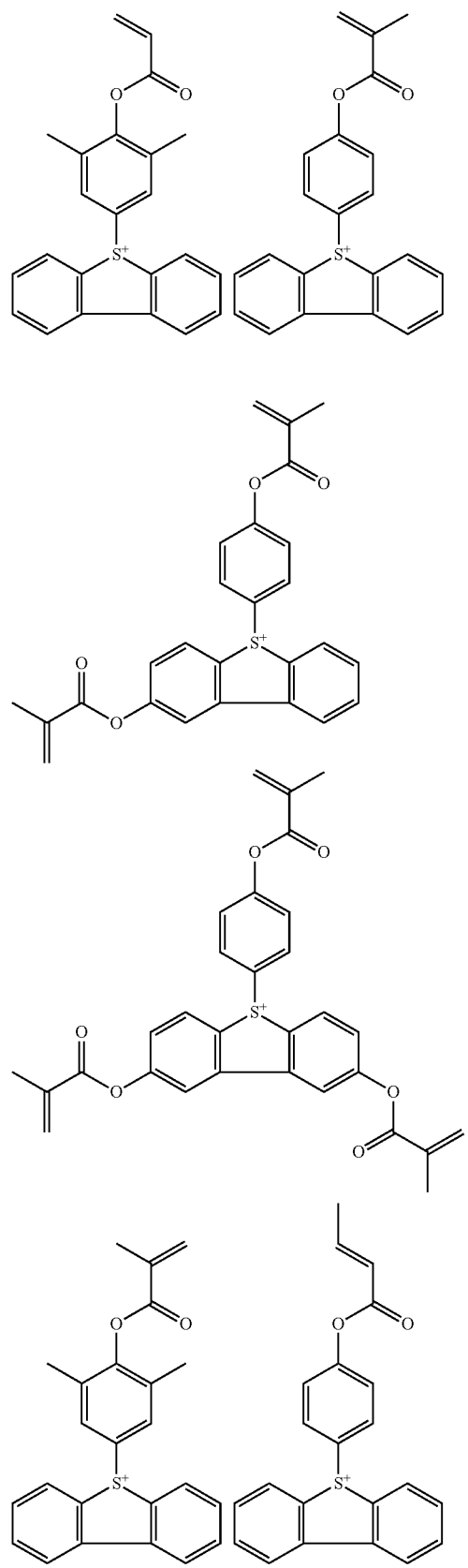
78
-continued
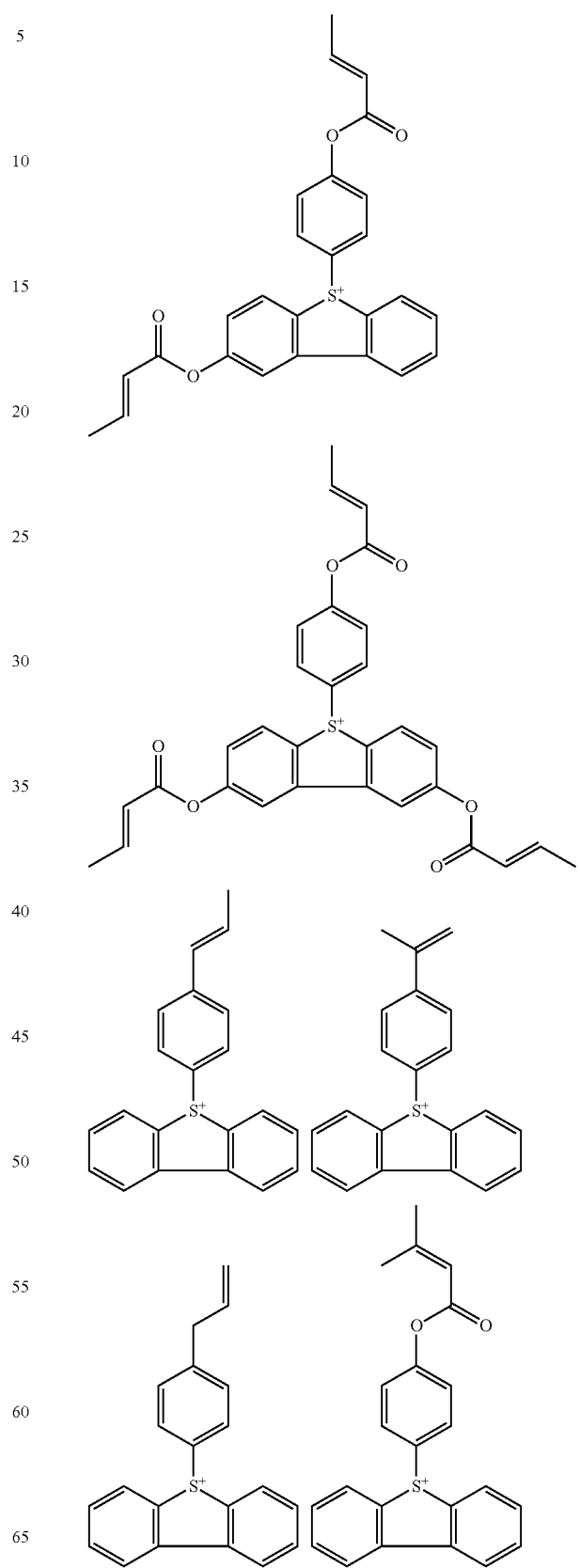

-continued
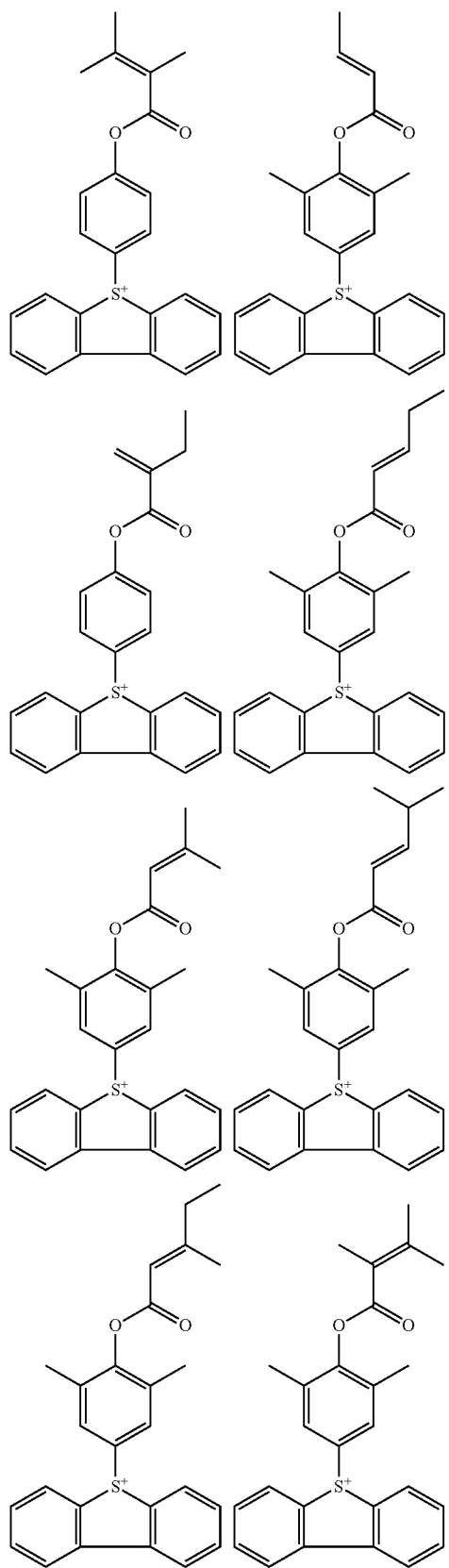
-continued
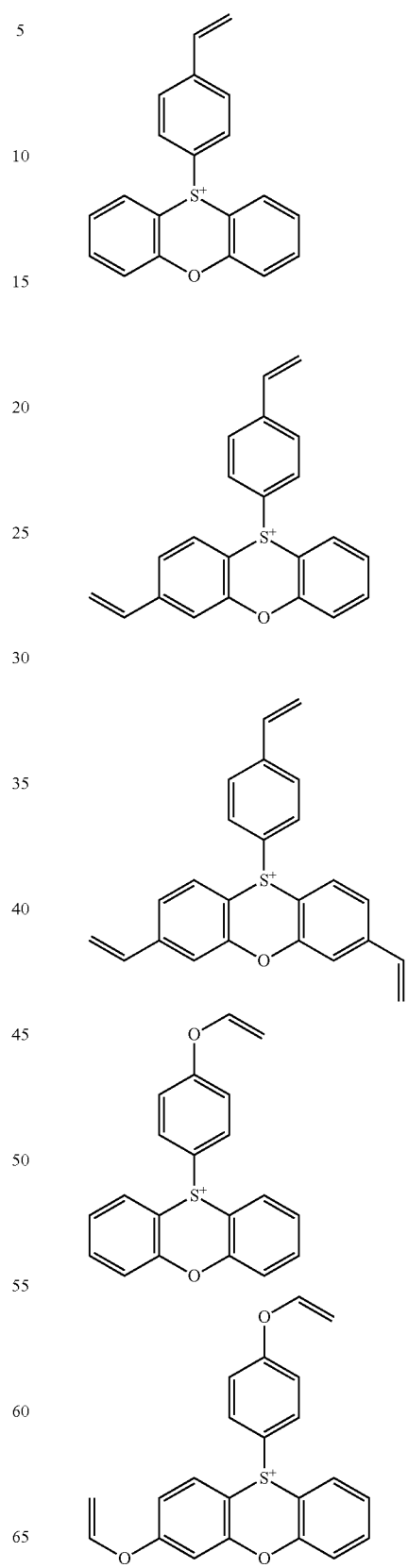

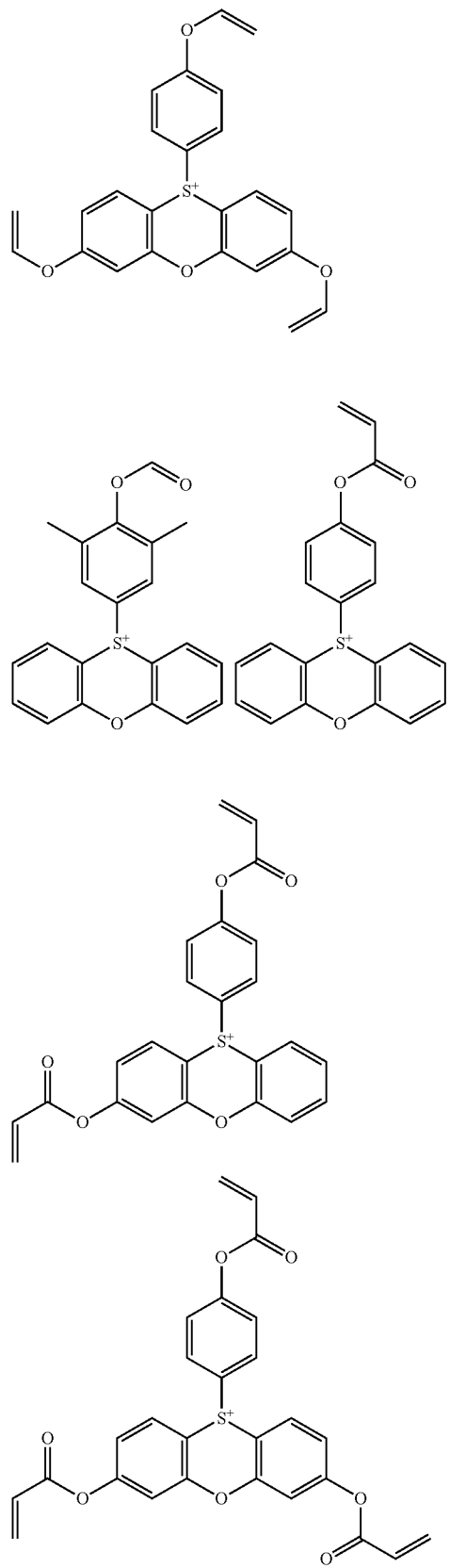
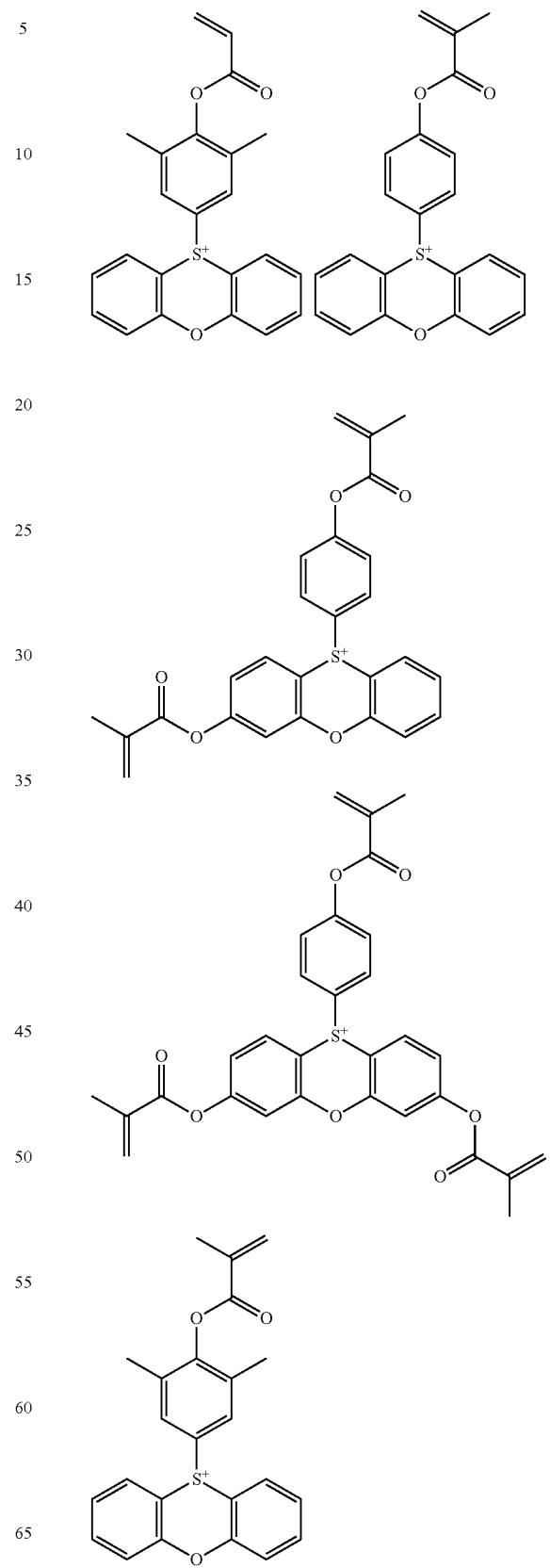

-continued

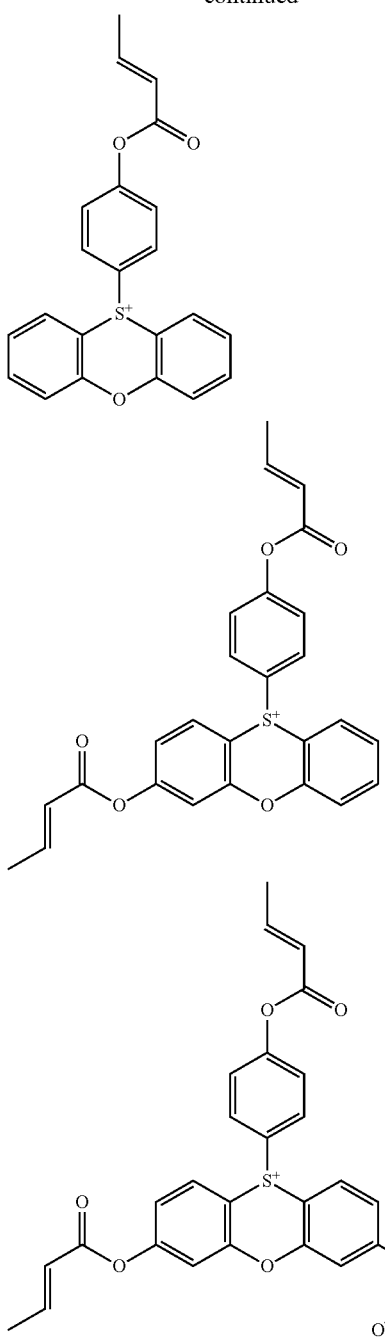

The sulfonium salt having formula (A) may be synthesized, for example, by ion exchange of a fluorosulphonic acid providing the aforementioned anion with a sulfonium salt of a weaker acid than the fluorosulphonic acid, containing the aforementioned sulfonium cation. Suitable weak acids include carbonic acid and halogens. Alternatively, the sulfonium salt may be synthesized by ion exchange of a sodium or ammonium salt of a fluorosulphonic acid providing the aforementioned anion with a sulfonium chloride containing the aforementioned sulfonium cation.

In the negative resist composition, the sulfonium salt having formula (A) as the acid generator is preferably used in an amount of 0.01 to 1,000 parts, more preferably 0.05 to 500 parts by weight per 100 parts by weight of the base polymer, as viewed from sensitivity and acid diffusion-suppressing effect.

Base Polymer

The base polymer in the negative resist composition is preferably defined as comprising repeat units having the formula (a1), which are also referred to as repeat units (a1).

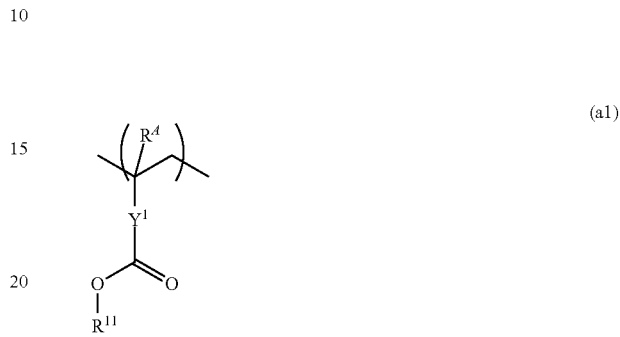

In formula (a1), $R^A$ is hydrogen or methyl. $Y^1$ is a single bond, phenylene or naphthylene group, or a $C_1$-$C_{12}$ linking group containing at least one moiety selected from an ester bond, ether bond and lactone ring. $R^{11}$ is an acid labile group.

Examples of the monomer from which repeat units (a1) are derived are shown below, but not limited thereto. $R^A$ and $R^{11}$ are as defined above.

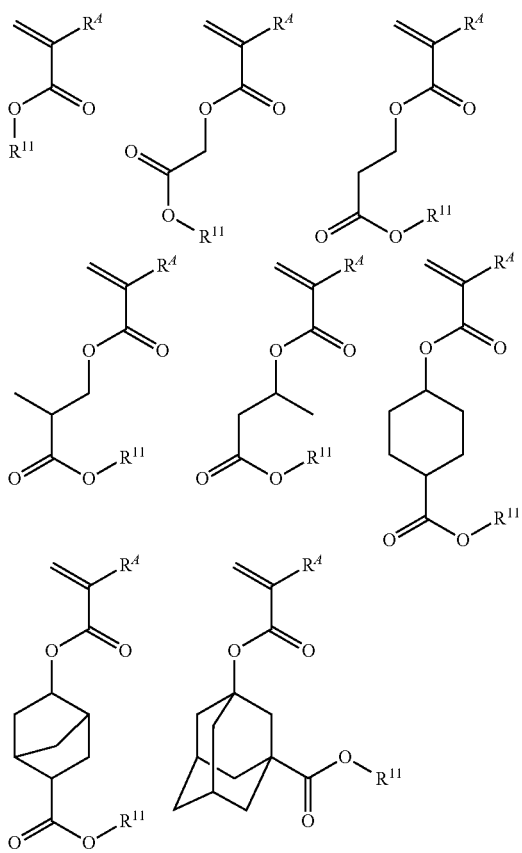

-continued

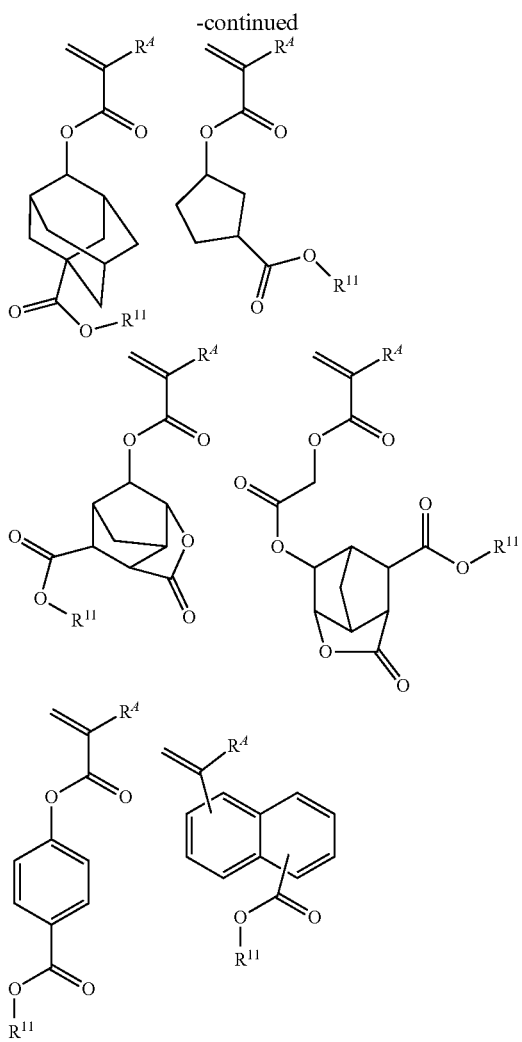

The base polymer may further comprise repeat units having the formula (a2), which are also referred to as repeat units (a2).

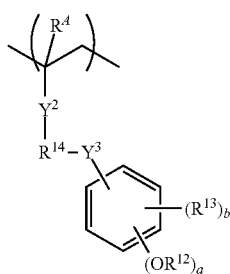

(a2)

In formula (a2), $R^A$ is hydrogen or methyl. $Y^2$ is a single bond or ester bond. $Y^3$ is a single bond, ether bond or ester bond. $R^{12}$ is an acid labile group. $R^{13}$ is fluorine, trifluoromethyl, cyano, a $C_1$-$C_6$ saturated hydrocarbyl group, $C_1$-$C_6$ saturated hydrocarbyloxy group, $C_2$-$C_7$ saturated hydrocarbylcarbonyl group, $C_2$-$C_7$ saturated hydrocarbylcarbonyloxy group or $C_2$-$C_7$ saturated hydrocarbyloxycarbonyl group. $R^{14}$ is a single bond or a $C_1$-$C_6$ alkanediyl group in which some carbon may be replaced by an ether bond or ester bond. The subscript "a" is 1 or 2, and "b" is an integer of 0 to 4.

Examples of the monomer from which repeat units (a2) are derived are shown below, but not limited thereto. $R^A$ and $R^{12}$ are as defined above.

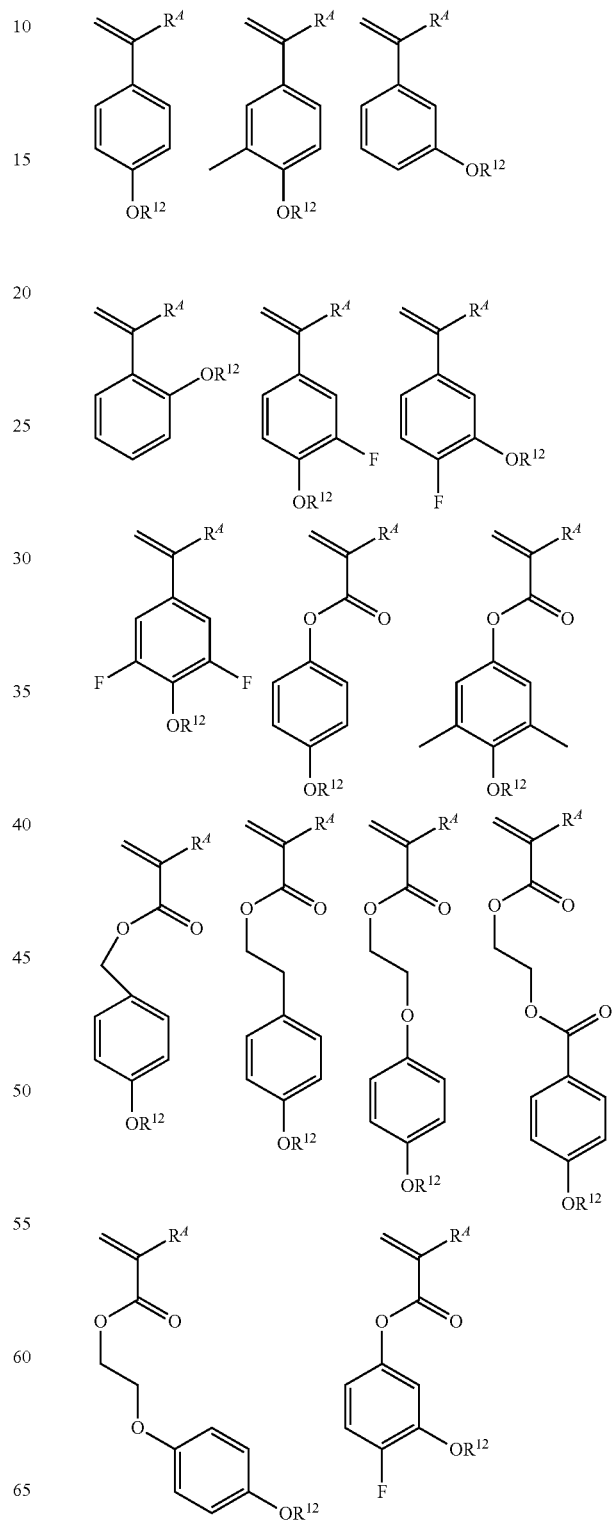

-continued

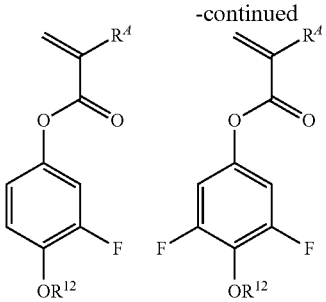

The acid labile groups represented by $R^{11}$ and $R^{12}$ in formulae (a1) and (a2) may be selected from a variety of such groups, for example, those groups described in JP-A 2013-080033 (U.S. Pat. No. 8,574,817) and JP-A 2013-083821 (U.S. Pat. No. 8,846,303).

Typical of the acid labile group are groups of the following formulae (AL-1) to (AL-3).

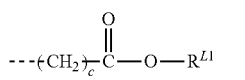 (AL-1)

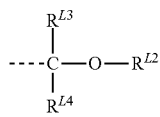 (AL-2)

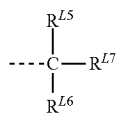 (AL-3)

In formulae (AL-1) and (AL-2), $R^{L1}$ and $R^{L2}$ are each independently a $C_1$-$C_{40}$ hydrocarbyl group which may contain a heteroatom such as oxygen, sulfur, nitrogen or fluorine. The hydrocarbyl group may be saturated or unsaturated and straight, branched or cyclic. Inter alia, $C_1$-$C_{40}$ saturated hydrocarbyl groups are preferred, and $C_1$-$C_{20}$ saturated hydrocarbyl groups are more preferred.

In formula (AL-1), c is an integer of 0 to 10, preferably 1 to 5.

In formula (AL-2), $R^{L3}$ and $R^{L4}$ are each independently hydrogen or a $C_1$-$C_{20}$ hydrocarbyl group which may contain a heteroatom such as oxygen, sulfur, nitrogen or fluorine. The hydrocarbyl group may be saturated or unsaturated and straight, branched or cyclic. Inter alia, $C_1$-$C_{20}$ saturated hydrocarbyl groups are preferred. Any two of $R^{L2}$, $R^{L3}$ and $R^{L4}$ may bond together to form a $C_3$-$C_{20}$ ring with the carbon atom or carbon and oxygen atoms to which they are attached. The ring preferably contains 4 to 16 carbon atoms and is typically alicyclic.

In formula (AL-3), $R^L$, $R^{L6}$ and $R^{L7}$ are each independently a $C_1$-$C_{20}$ hydrocarbyl group which may contain a heteroatom such as oxygen, sulfur, nitrogen or fluorine. The hydrocarbyl group may be saturated or unsaturated and straight, branched or cyclic. Inter alia, $C_1$-$C_{20}$ saturated hydrocarbyl groups are preferred. Any two of $R^L$, $R^{L6}$ and $R^{L7}$ may bond together to form a $C_3$-$C_{20}$ ring with the carbon atom to which they are attached. The ring preferably contains 4 to 16 carbon atoms and is typically alicyclic.

The base polymer may further comprise repeat units (b) having a phenolic hydroxy group as an adhesive group. Examples of suitable monomers from which repeat units (b) are derived are given below, but not limited thereto. Herein $R^A$ is as defined above.

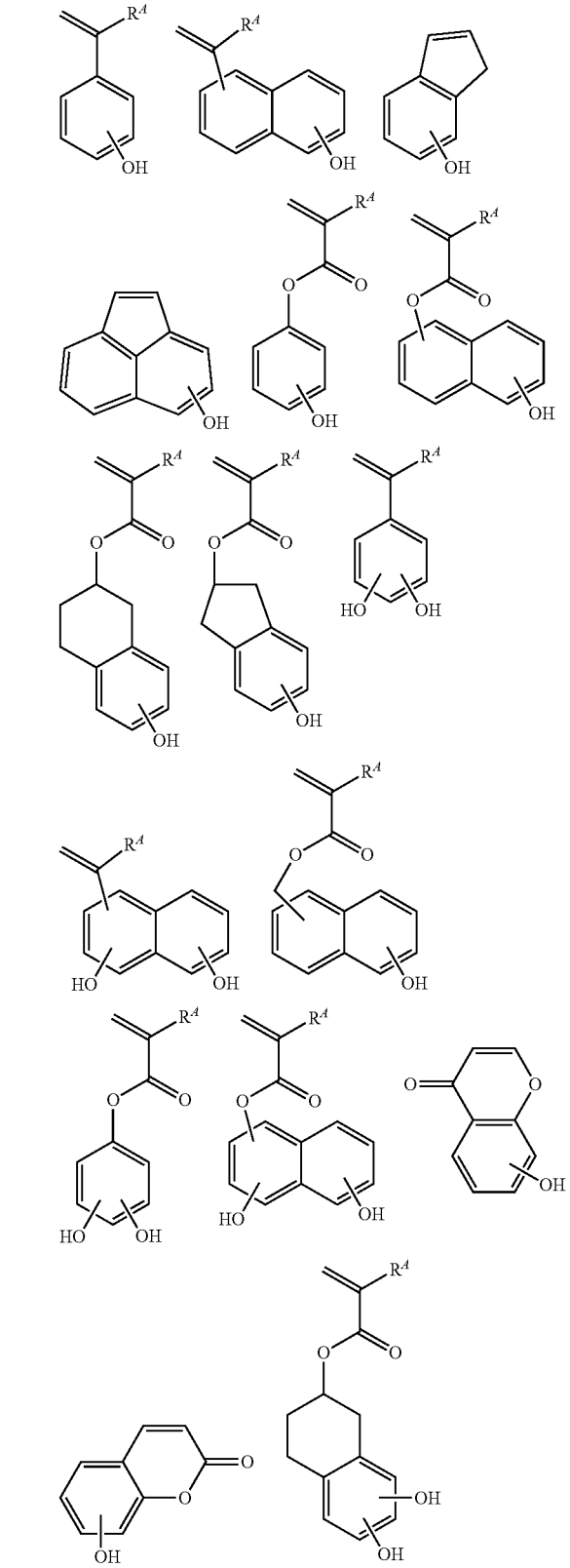

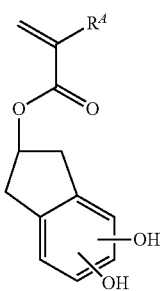

The base polymer may further comprise repeat units (c) having another adhesive group selected from hydroxy group (other than the foregoing phenolic hydroxy), lactone ring, sultone ring, ether bond, ester bond, sulfonic ester bond, carbonyl group, sulfonyl group, cyano group, and carboxy group. Examples of suitable monomers from which repeat units (c) are derived are given below, but not limited thereto. Herein $R^A$ is as defined above.

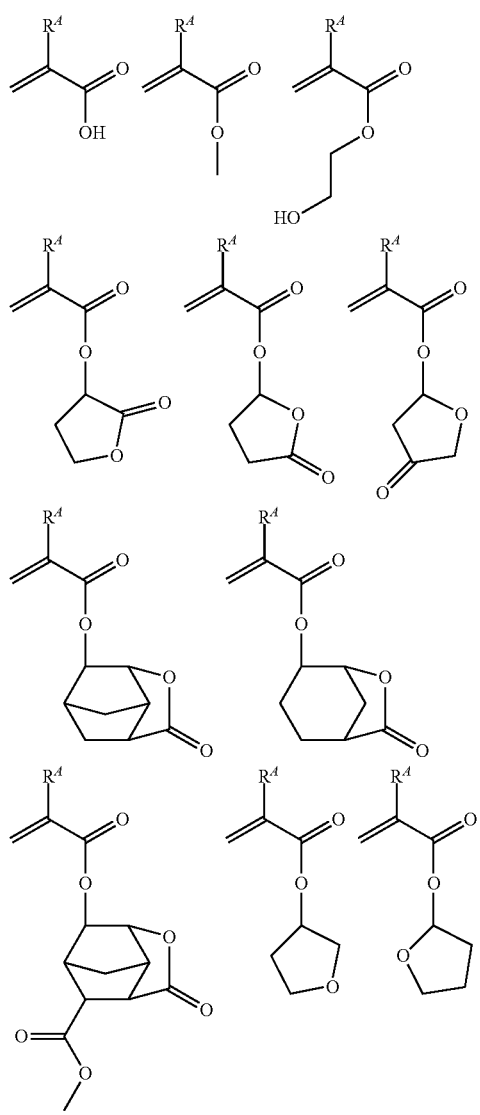

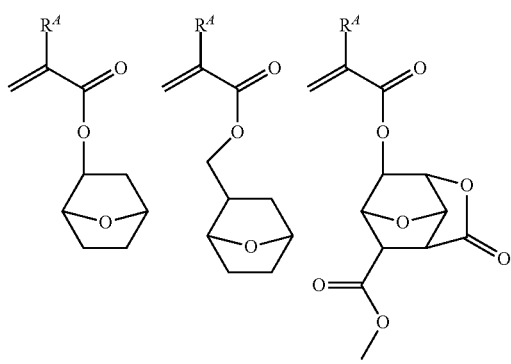

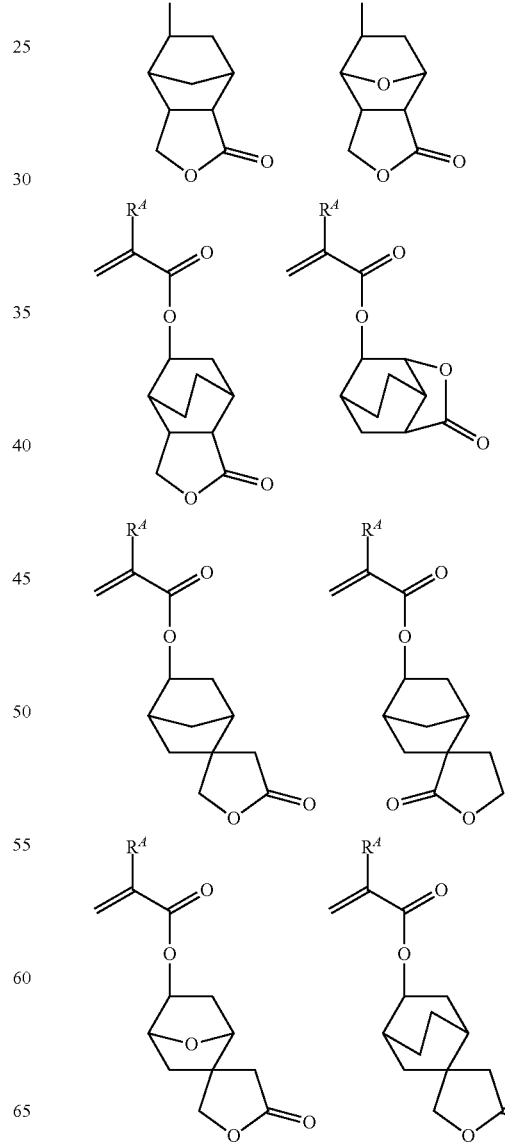

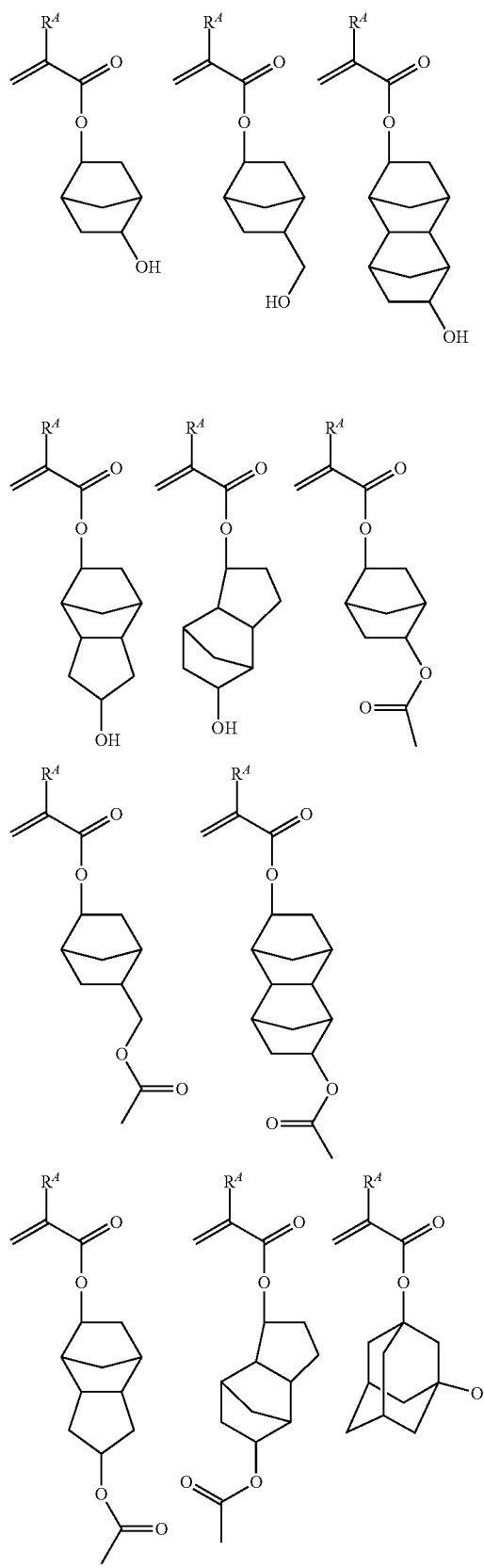
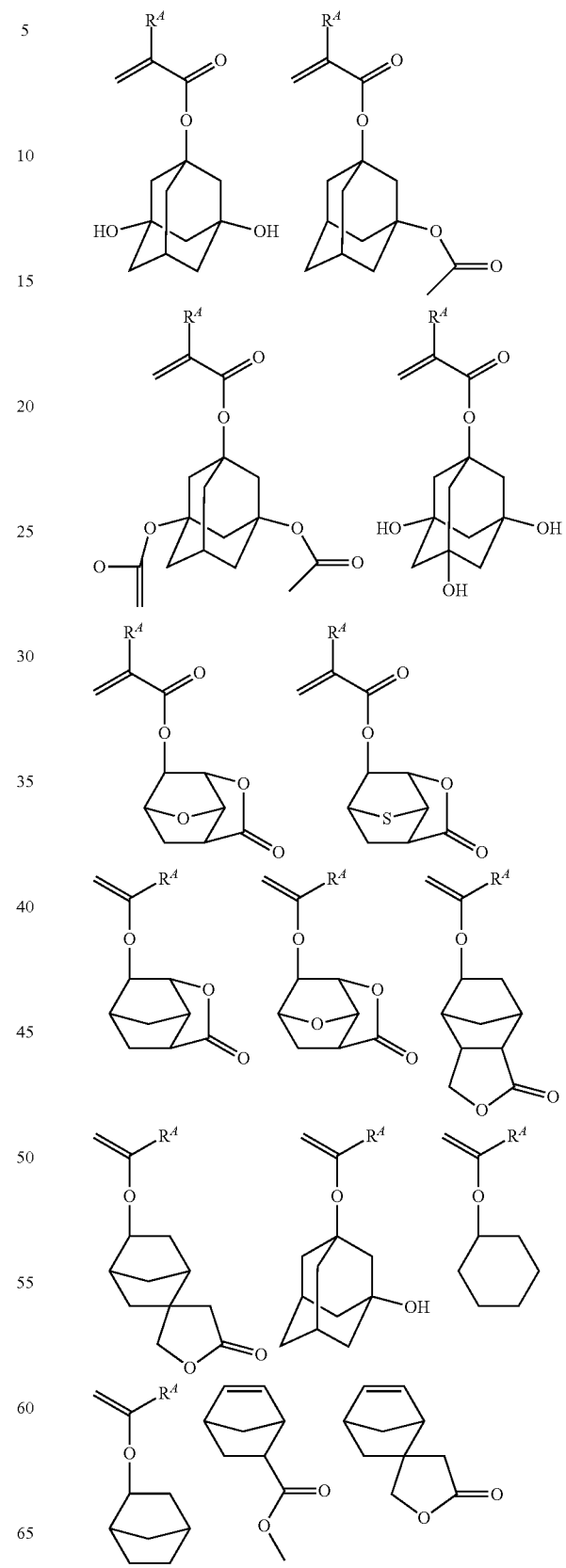

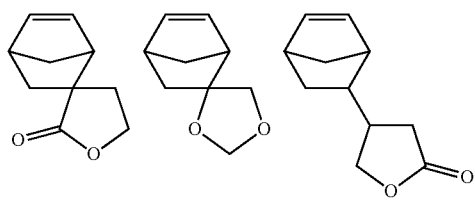
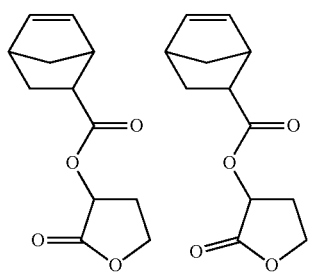
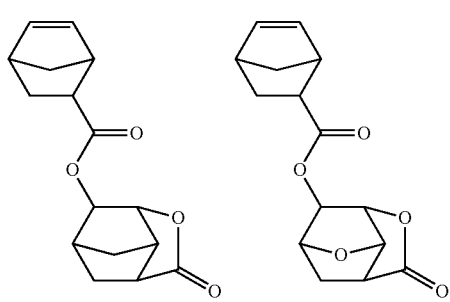
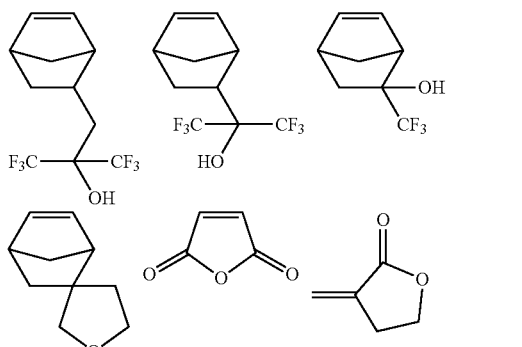
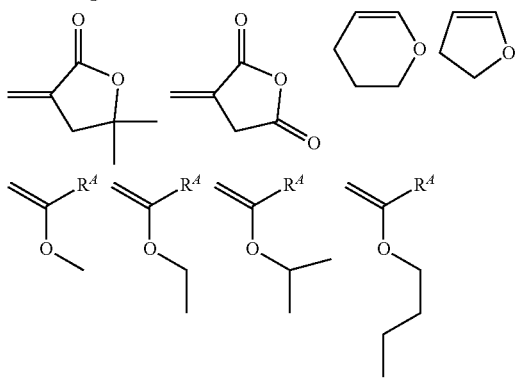
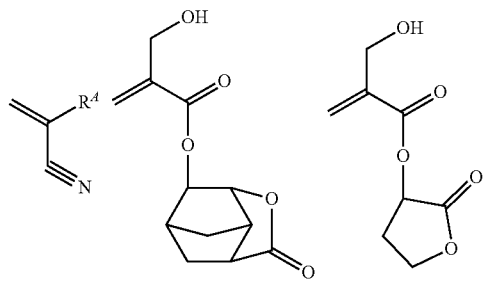
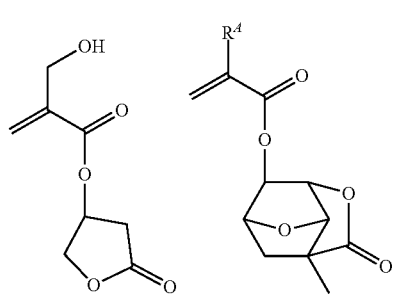
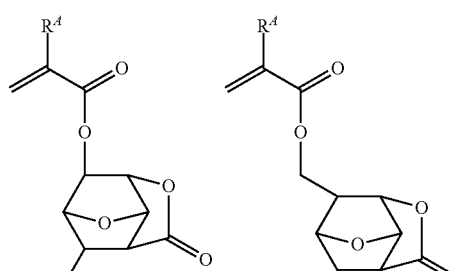
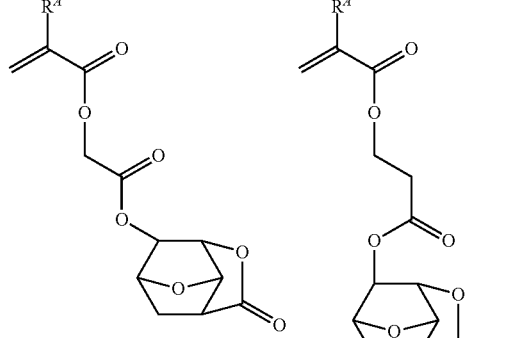
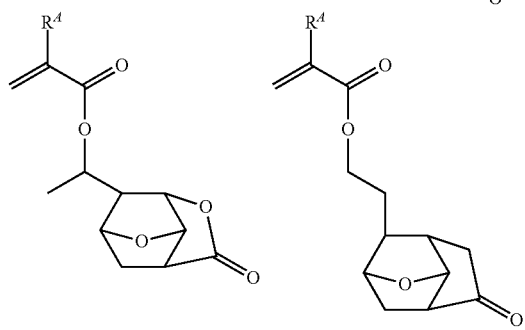

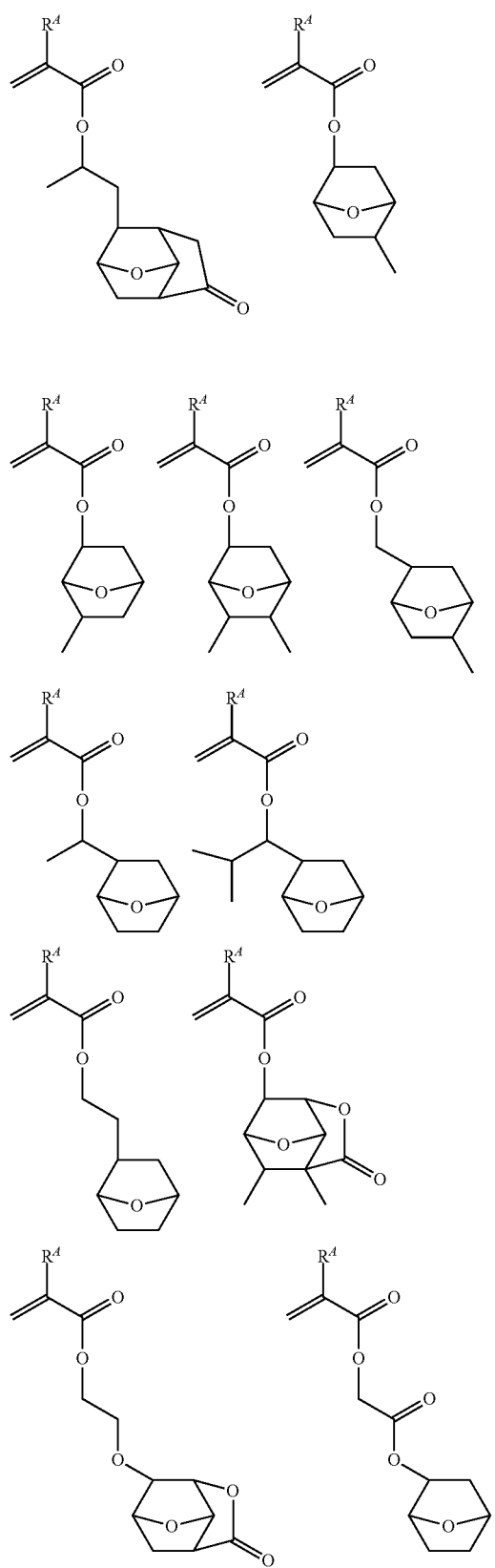
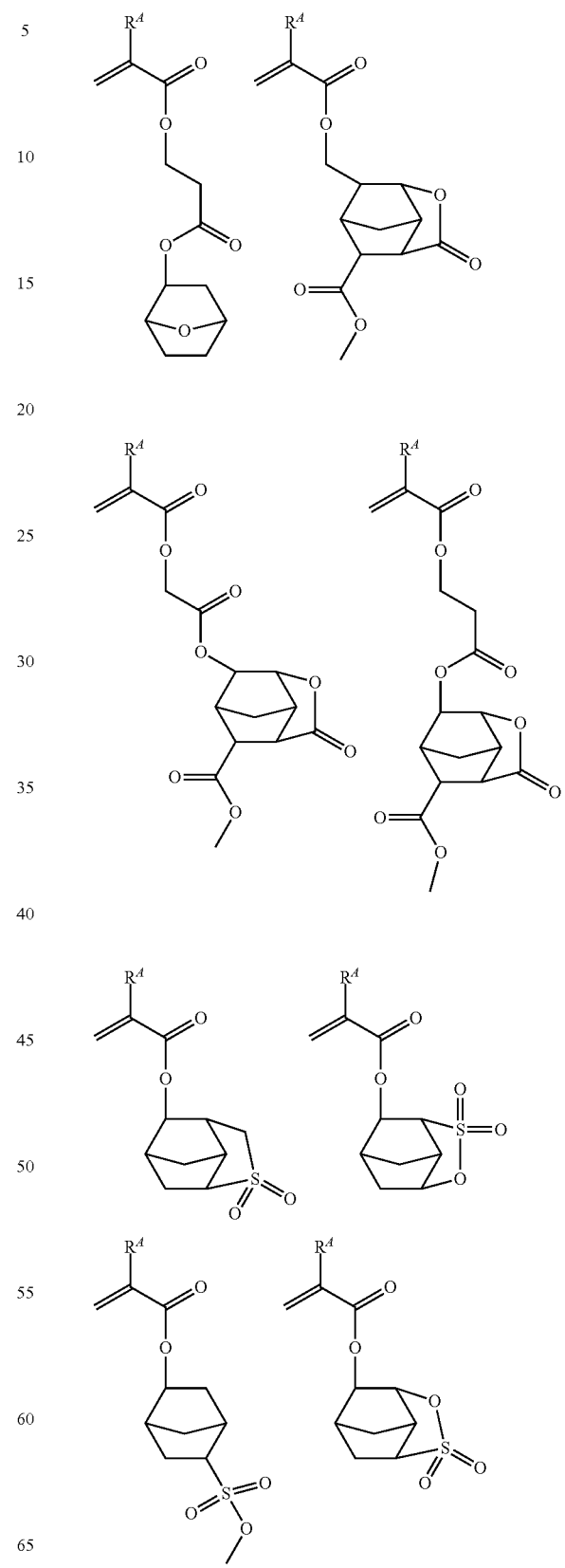

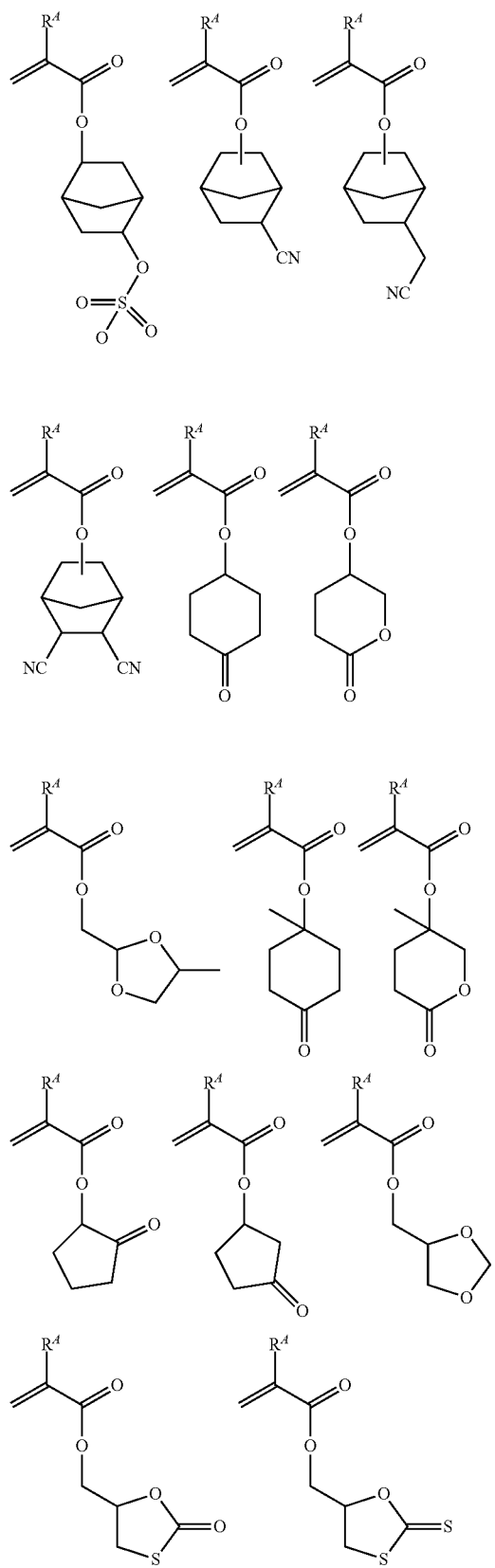
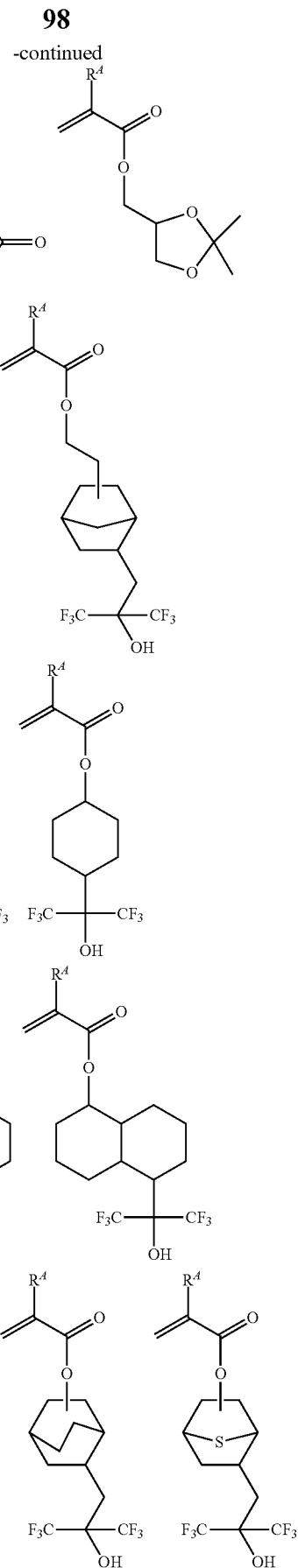

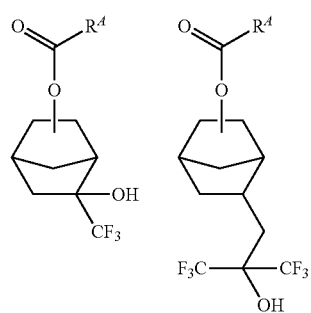
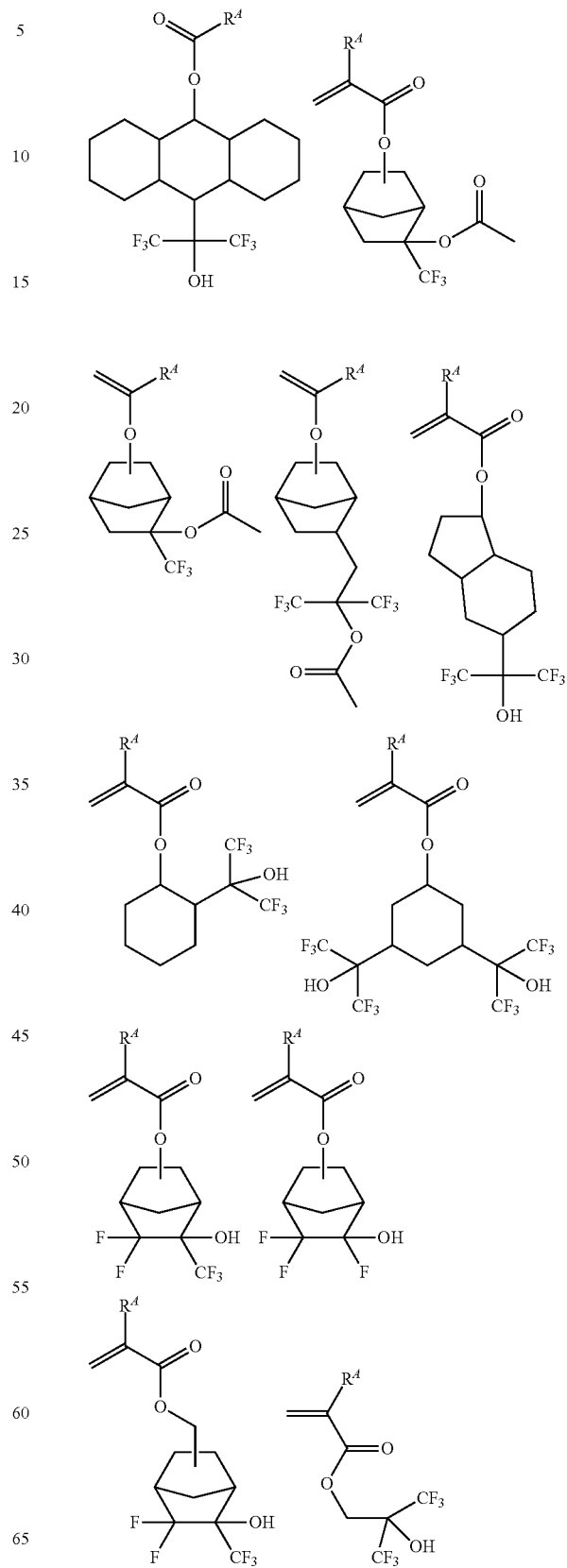

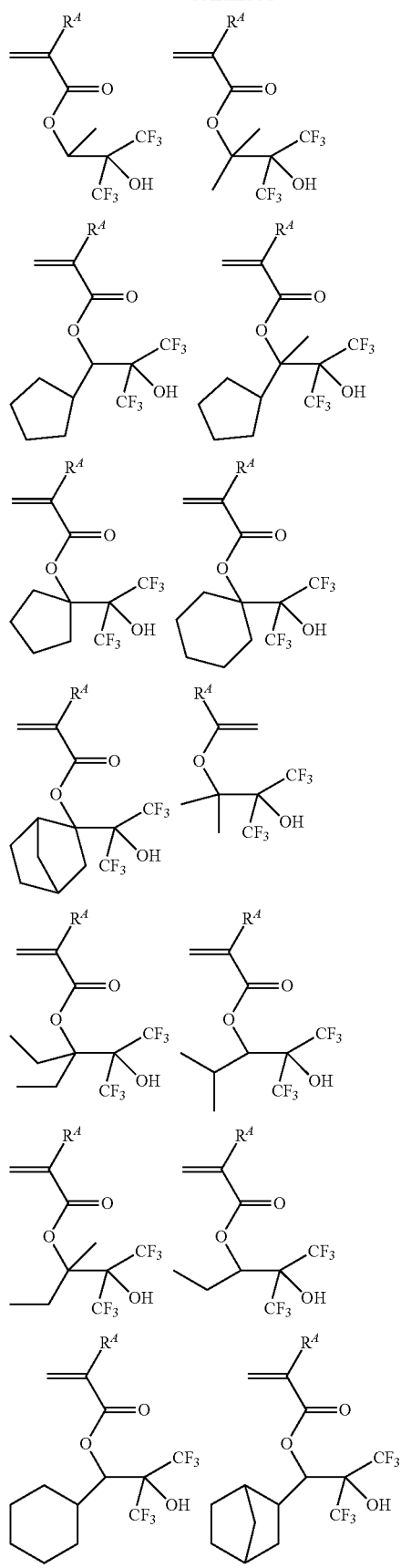
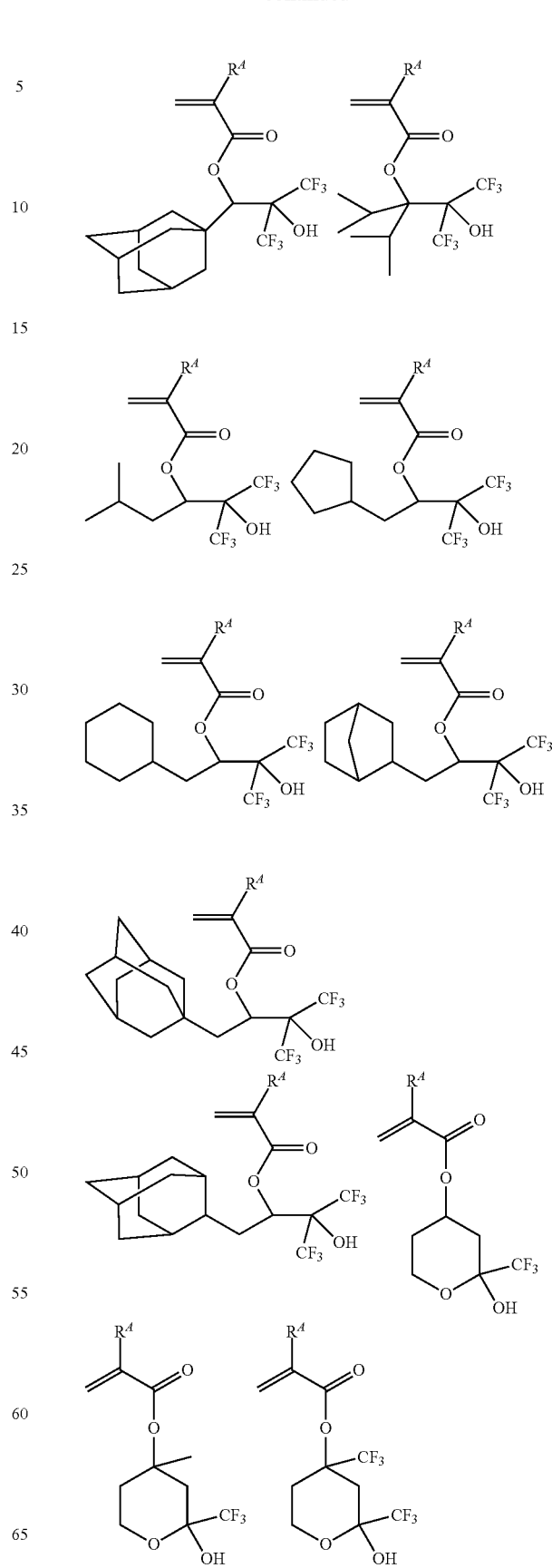

103
-continued
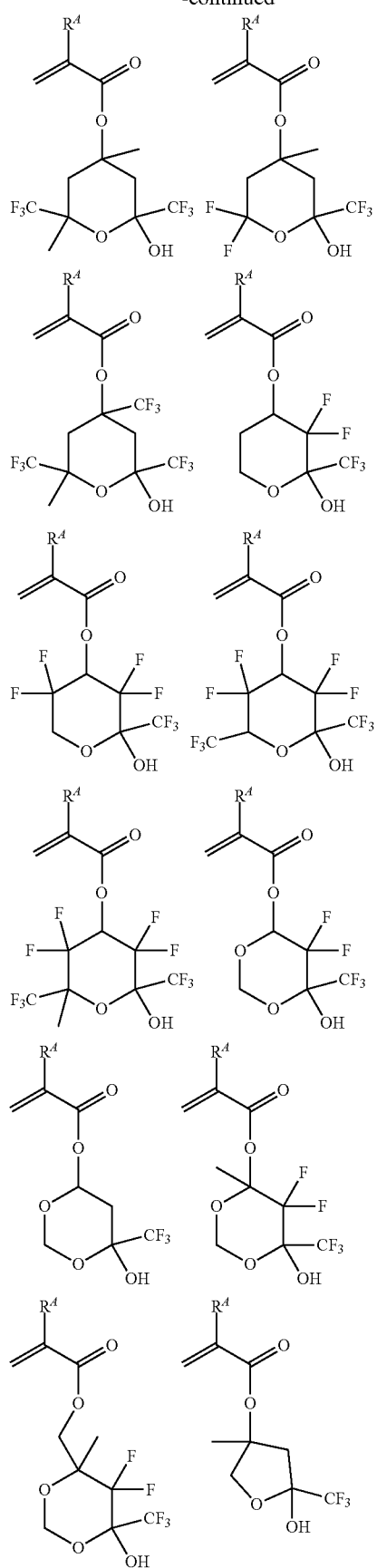
104
-continued
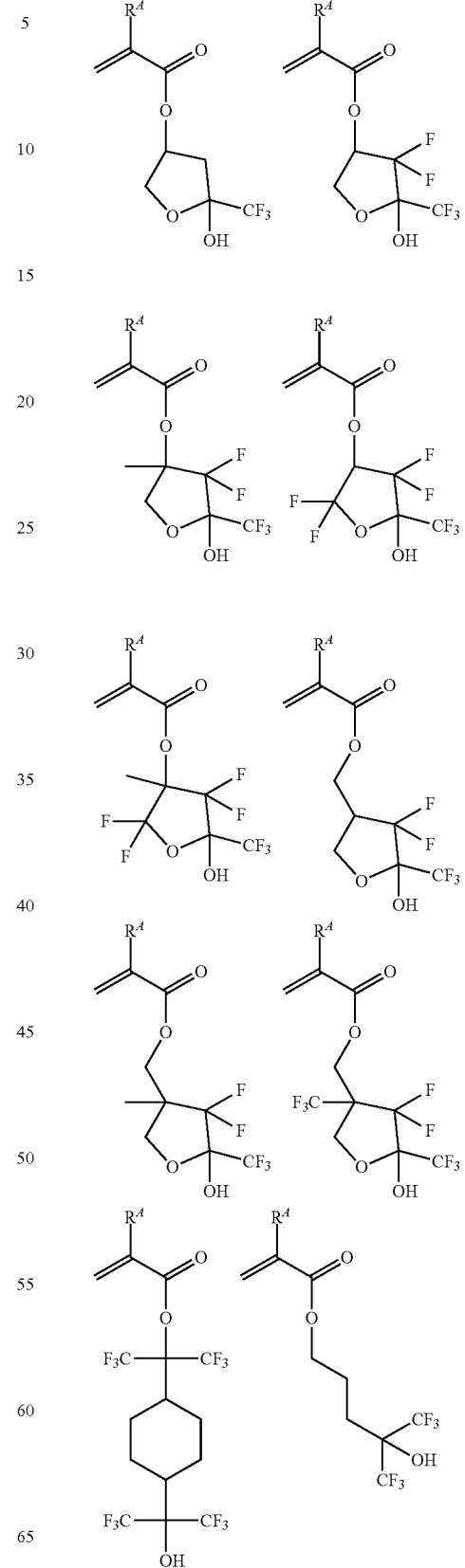

-continued
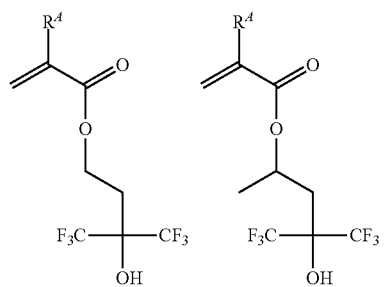
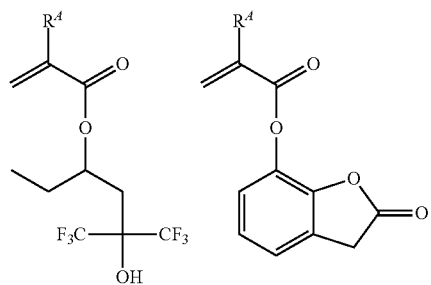
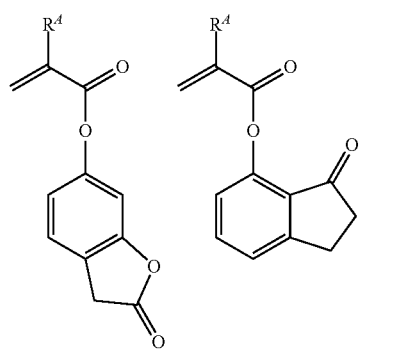
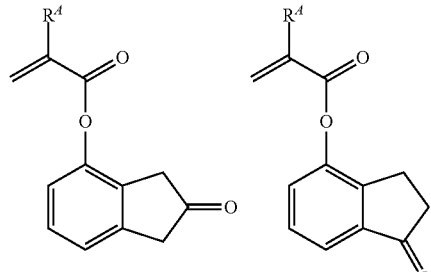
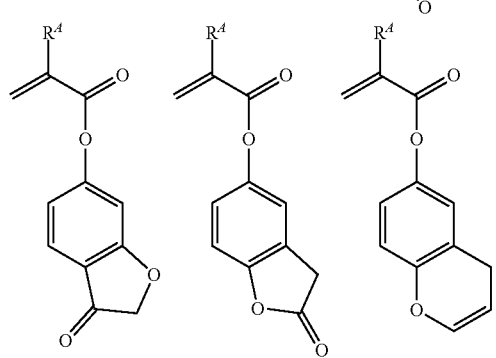
-continued
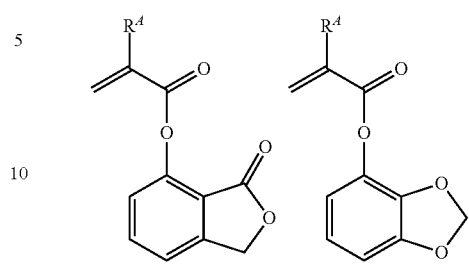
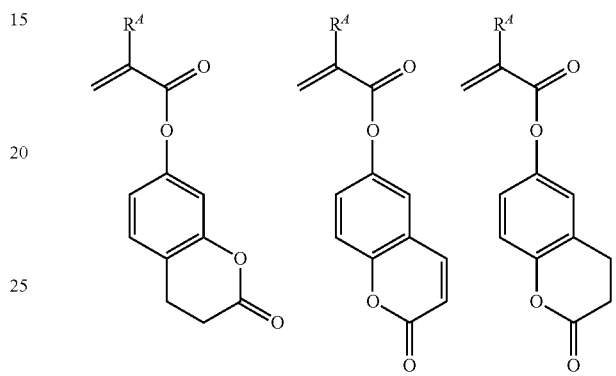
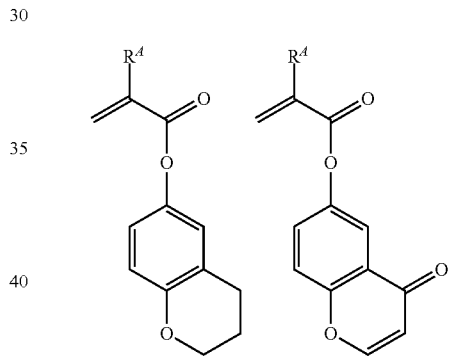
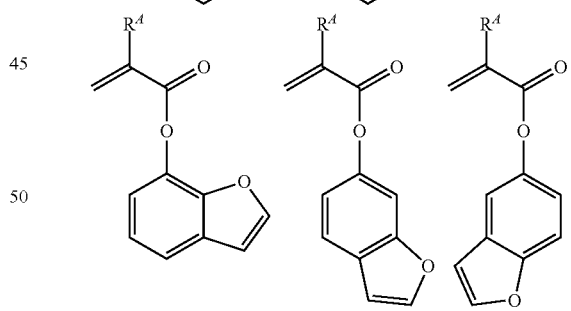
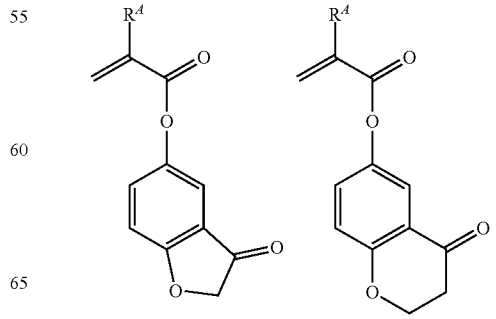

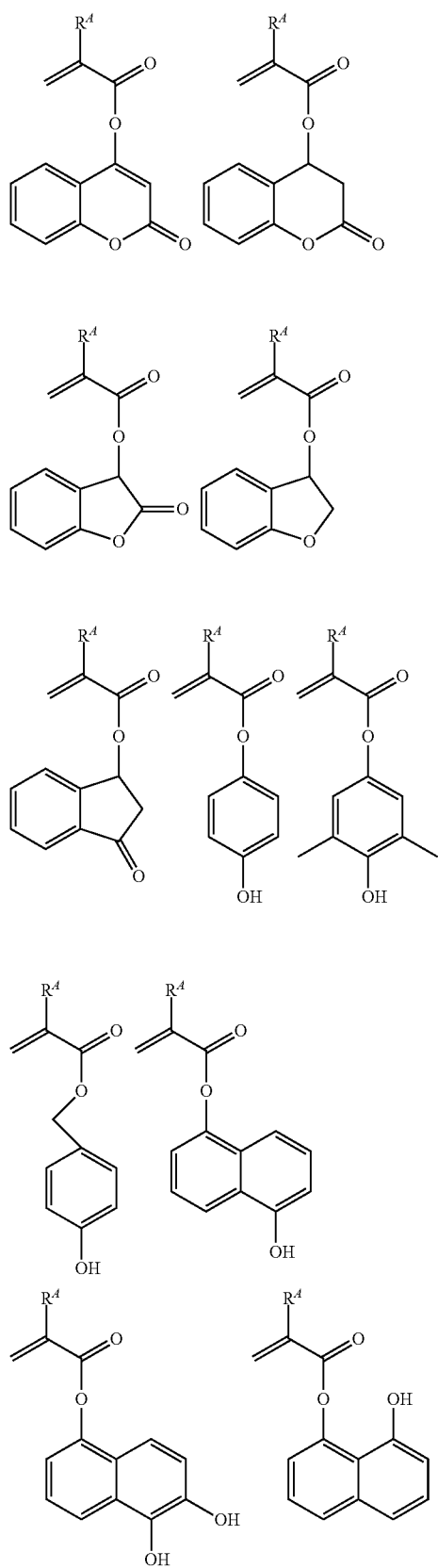
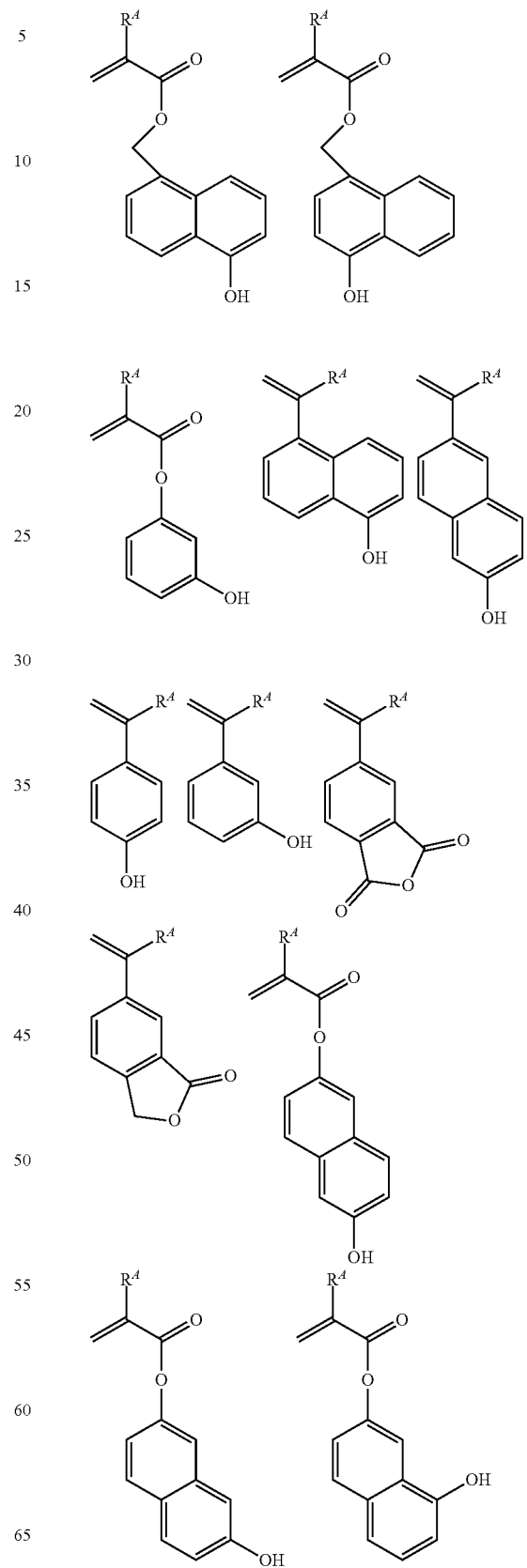

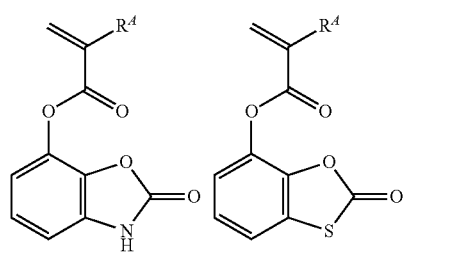
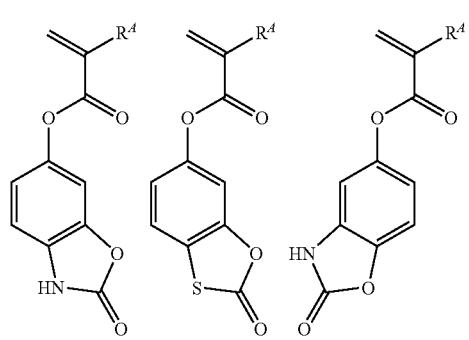
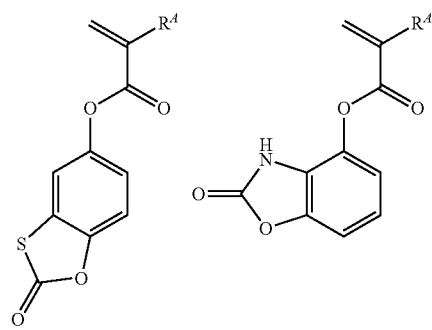
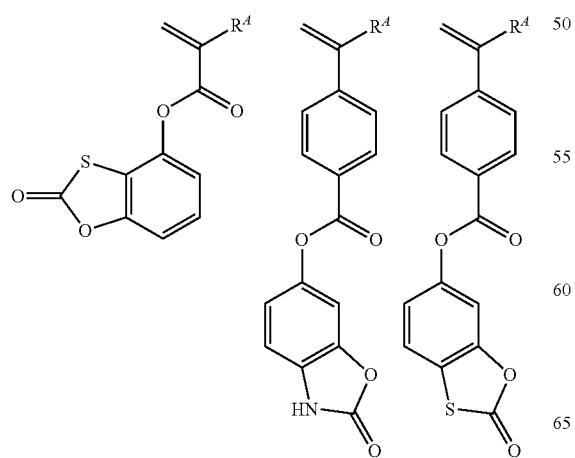
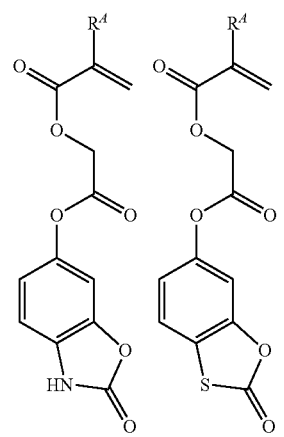
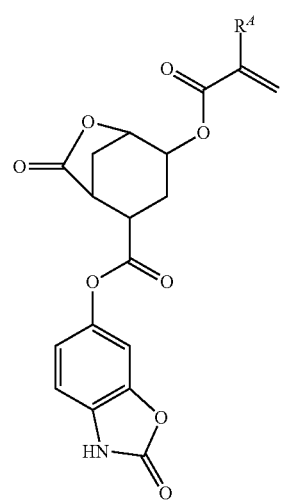
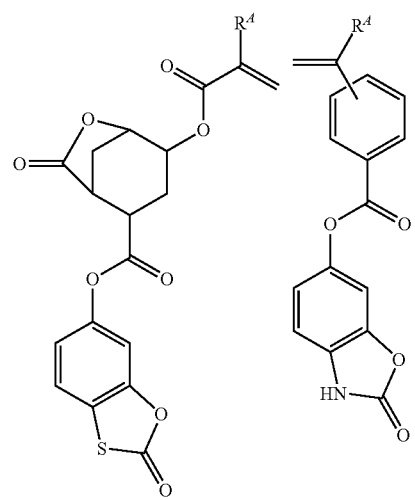

111
-continued

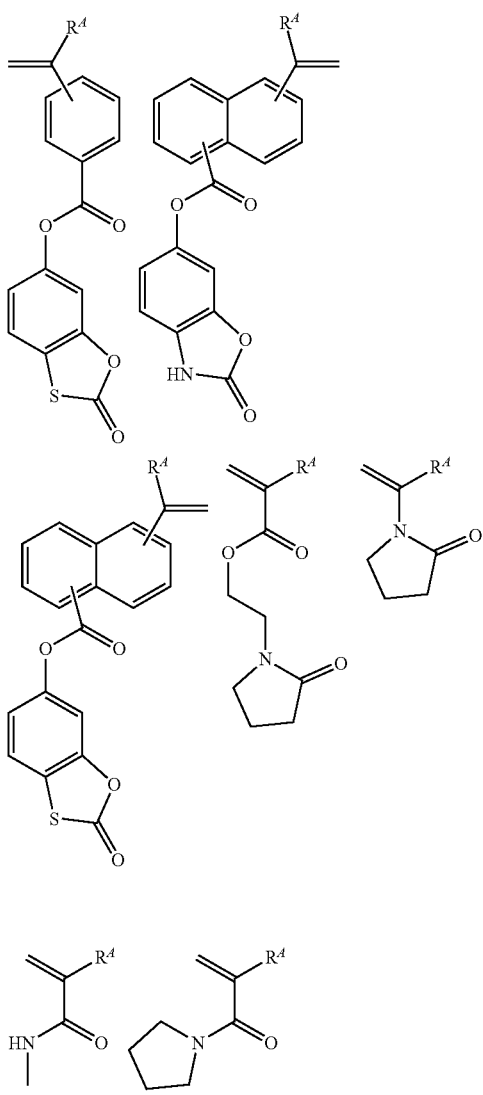

In another preferred embodiment, the base polymer may further comprise repeat units (d) derived from indene, benzofuran, benzothiophene, acenaphthylene, chromone, coumarin, norbornadiene, or derivatives thereof. Suitable monomers are exemplified below, but not limited thereto.

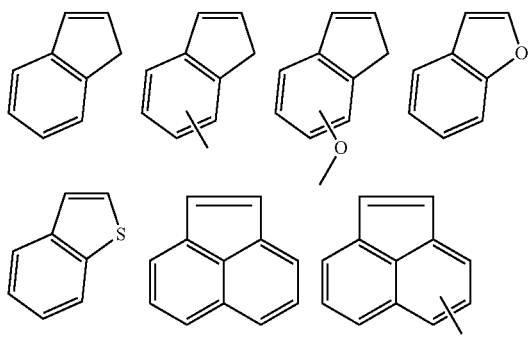

112
-continued

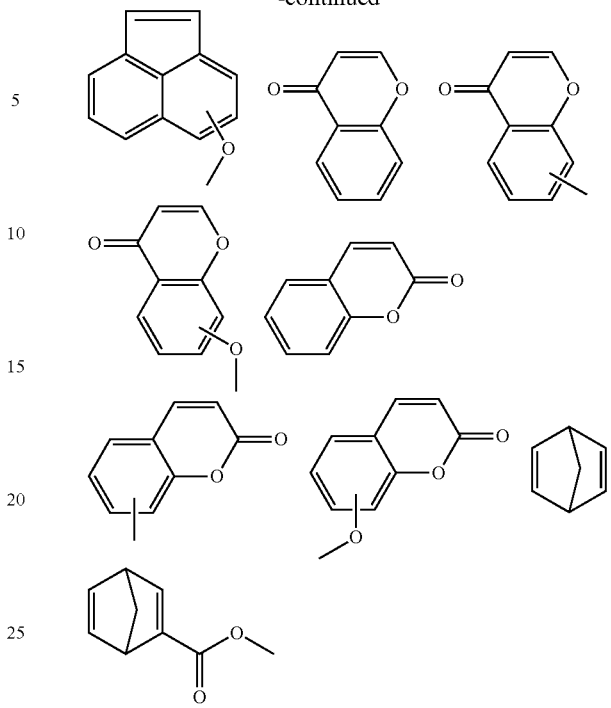

The base polymer may further comprise repeat units (e) which are derived from styrene, vinylnaphthalene, vinylanthracene, vinylpyrene, methyleneindene, vinylpyridine, vinylcarbazole, or derivatives thereof.

The base polymer for formulating the negative resist composition comprises repeat units (a1) having an acid labile group as essential component and additional repeat units (a2), (b), (c), (d), and (e) as optional components. A fraction of units (a1), (a2), (b), (c), (d), and (e) is: preferably $0<a1<1.0$, $0 \le a2<1.0$, $0<a1+a2<1.0$, $0 \le b \le 0.9$, $0 \le c \le 0.9$, $0 \le d \le 0.8$, and $0 \le e \le 0.8$; more preferably $0.1 \le a1 \le 0.9$, $0 \le a2 \le 0.9$, $0.1 \le a1+a2 \le 0.9$, $0 \le b \le 0.8$, $0 \le c \le 0.8 \le d \le 0.7$, and $0 \le e \le 0.7$; and even more preferably $0.2 \le a1 \le 0.8$, $0 \le a2 \le 0.8$, $0.2 \le a1+a2 \le 0.8$, $0 \le b \le 0.75$, $0 \le c \le 0.75$, $0 \le d \le 0.6$, and $0 \le e \le 0.6$. Notably, $a1+a2+b+c+d+e=1.0$.

The base polymer may be synthesized by any desired methods, for example, by dissolving one or more monomers selected from the monomers corresponding to the foregoing repeat units in an organic solvent, adding a radical polymerization initiator thereto, and heating for polymerization. Examples of the organic solvent which can be used for polymerization include toluene, benzene, tetrahydrofuran (THF), diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably, the reaction temperature is 50 to 80° C. and the reaction time is 2 to 100 hours, more preferably 5 to 20 hours.

Where a monomer having a hydroxy group is copolymerized, the hydroxy group may be replaced by an acetal group susceptible to deprotection with acid, typically ethoxyethoxy, prior to polymerization, and the polymerization be followed by deprotection with weak acid and water. Alternatively, the hydroxy group may be replaced by an acetyl, formyl, pivaloyl or similar group prior to polymerization, and the polymerization be followed by alkaline hydrolysis.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinylnaphthalene, and after polymerization, the acetoxy group is deprotected by alkaline hydrolysis, for thereby converting the polymer product to hydroxystyrene or hydroxyvinylnaphthalene. For alkaline hydrolysis, a base such as aqueous ammonia or triethylamine may be used. Preferably the reaction temperature is –20° C. to 100° C., more preferably 0° C. to 60° C., and the reaction time is 0.2 to 100 hours, more preferably 0.5 to 20 hours.

The base polymer should preferably have a weight average molecular weight (Mw) in the range of 1,000 to 500,000, and more preferably 2,000 to 30,000, as measured by GPC versus polystyrene standards using tetrahydrofuran (THF) solvent. A Mw in the range ensures that a resist film is heat resistant and readily soluble in the organic solvent developer.

If a base polymer has a wide molecular weight distribution or dispersity (Mw/Mn), which indicates the presence of lower and higher molecular weight polymer fractions, there is a possibility that foreign matter is left on the pattern or the pattern profile is degraded. The influences of Mw and Mw/Mn become stronger as the pattern rule becomes finer. Therefore, the base polymer should preferably have a narrow dispersity (Mw/Mn) of 1.0 to 2.0, especially 1.0 to 1.5, in order to provide a resist composition suitable for micropatterning to a small feature size.

It is understood that a blend of two or more polymers which differ in compositional ratio, Mw or Mw/Mn is acceptable.

Organic Solvent

An organic solvent may be added to the resist composition. The organic solvent used herein is not particularly limited as long as the foregoing and other components are soluble therein. Examples of the organic solvent are described in JP-A 2008-111103, paragraphs [0144]-[0145] (U.S. Pat. No. 7,537,880). Exemplary solvents include ketones such as cyclohexanone, cyclopentanone, methyl-2-n-pentyl ketone and 2-heptanone; alcohols such as 3-methoxybutanol, 3-methyl-3-methoxybutanol, 1-methoxy-2-propanol, 1-ethoxy-2-propanol, and diacetone alcohol (DAA); ethers such as propylene glycol monomethyl ether (PGME), ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone, which may be used alone or in admixture.

The organic solvent is preferably added in an amount of 100 to 10,000 parts, and more preferably 200 to 8,000 parts by weight per 100 parts by weight of the base polymer.

Quencher

The negative resist composition may contain a quencher. As used herein, the "quencher" refers to a compound which traps the acid generated by the acid generator in the resist composition to prevent the acid from diffusing into the unexposed region.

The quencher is typically selected from conventional basic compounds. Conventional basic compounds include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxy group, nitrogen-containing compounds with hydroxyphenyl group, alcoholic nitrogen-containing compounds, amide derivatives, imide derivatives, and carbamate derivatives. Also included are primary, secondary, and tertiary amine compounds, specifically amine compounds having a hydroxy group, ether bond, ester bond, lactone ring, cyano group, or sulfonic ester bond as described in JP-A 2008-111103, paragraphs [0146]-[0164], and compounds having a carbamate group as described in JP 3790649. Addition of a basic compound may be effective for further suppressing the diffusion rate of acid in the resist film or correcting the pattern profile.

Onium salts such as sulfonium, iodonium and ammonium salts of sulfonic acids which are not fluorinated at α-position, carboxylic acids or fluorinated alkoxides may also be used as the quencher. While an α-fluorinated sulfonic acid, imide acid, and methide acid are necessary to deprotect the acid labile group of carboxylic acid ester, an α-non-fluorinated sulfonic acid, carboxylic acid or fluorinated alcohol is released by salt exchange with the onium salt. The α-non-fluorinated sulfonic acid, carboxylic acid and fluorinated alcohol function as a quencher because they do not induce deprotection reaction.

Examples of the quencher include a compound (onium salt of α-non-fluorinated sulfonic acid) having the formula (B), a compound (onium salt of carboxylic acid) having the formula (C), and a compound (onium salt of alkoxide) having the formula (D).

$$R^{101}\text{—}SO_3^-Mq^+ \tag{B}$$

$$R^{102}\text{—}CO_2^-Mq^+ \tag{C}$$

$$R^{103}\text{—}O^-Mq^+ \tag{D}$$

In formula (B), $R^{101}$ is hydrogen or a $C_1$-$C_{40}$ hydrocarbyl group which may contain a heteroatom, exclusive of the hydrocarbyl group in which the hydrogen bonded to the carbon atom at α-position of the sulfo group is substituted by fluorine or fluoroalkyl moiety.

The $C_1$-$C_{40}$ hydrocarbyl group may be saturated or unsaturated and straight, branched or cyclic. Examples thereof include $C_1$-$C_{40}$ alkyl groups such as methyl, ethyl, propyl, isopropyl, n-butyl, sec-butyl, tert-butyl, tert-pentyl, n-pentyl, n-hexyl, n-octyl, 2-ethylhexyl, n-nonyl, n-decyl; $C_3$-$C_{40}$ cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl; $C_2$-$C_{40}$ alkenyl groups such as vinyl, allyl, propenyl, butenyl and hexenyl; $C_3$-$C_{40}$ cyclic unsaturated aliphatic hydrocarbyl groups such as cyclohexenyl; $C_6$-$C_{40}$ aryl groups such as phenyl, naphthyl, alkylphenyl groups (e.g., 2-methylphenyl, 3-methylphenyl, 4-methylphenyl, 4-ethylphenyl, 4-tert-butylphenyl, 4-n-butylphenyl), dialkylphenyl groups (e.g., 2,4-dimethylphenyl and 2,4,6-triisopropylphenyl), alkylnaphthyl groups (e.g., methylnaphthyl and ethylnaphthyl), dialkylnaphthyl groups (e.g., dimethylnaphthyl and diethylnaphthyl); and $C_7$-$C_{40}$ aralkyl groups such as benzyl, 1-phenylethyl and 2-phenylethyl.

In the hydrocarbyl group, some or all of the hydrogen atoms may be substituted by a moiety containing a heteroatom such as oxygen, sulfur, nitrogen or halogen, and some constituent —$CH_2$— may be replaced by a moiety containing a heteroatom such as oxygen, sulfur or nitrogen, so that the group may contain a hydroxy moiety, cyano moiety, carbonyl moiety, ether bond, thioether bond, ester bond, sulfonic ester bond, carbonate bond, lactone ring, sultone ring, carboxylic anhydride (—C(=O)—O—C(=O)—), or haloalkyl moiety. Suitable heteroatom-containing hydrocarbyl groups include heteroaryl groups such as thienyl, 4-hydroxyphenyl, alkoxyphenyl groups such as 4-methoxyphenyl, 3-methoxyphenyl, 2-methoxyphenyl, 4-ethoxyphenyl, 4-tert-butoxyphenyl, 3-tert-butoxyphenyl; alkoxynaphthyl groups such as methoxynaphthyl, ethoxynaphthyl, n-propoxynaphthyl and n-butoxynaphthyl; dialkoxynaphthyl groups such as dimethoxynaphthyl and diethoxynaphthyl; and aryloxoalkyl groups, typically 2-aryl-2-oxoethyl groups such as 2-phenyl-2-oxoethyl, 2-(1-naphthyl)-2-oxoethyl and 2-(2-naphthyl)-2-oxoethyl.

In formula (C), $R^{102}$ is a $C_1$-$C_{40}$ hydrocarbyl group which may contain a heteroatom. Examples of the hydrocarbyl group $R^{102}$ are as exemplified above for the hydrocarbyl group $R^{101}$. Also included are fluorinated alkyl groups such as trifluoromethyl, trifluoroethyl, 2,2,2-trifluoro-1-methyl-1-hydroxyethyl, 2,2,2-trifluoro-1-(trifluoromethyl)-1-hydroxyethyl, and fluorinated aryl groups such as pentafluorophenyl and 4-trifluoromethylphenyl.

In formula (D), $R^{103}$ is a $C_1$-$C_8$ saturated hydrocarbyl group containing at least 3 fluorine atoms or a $C_6$-$C_{10}$ aryl group containing at least 3 fluorine atoms, the hydrocarbyl and aryl groups optionally containing a nitro moiety.

In formulae (B), (C) and (D), $Mq^+$ is an onium cation. The onium cation is preferably a sulfonium cation having the formula (B-1), iodonium cation having the formula (C-1) or ammonium cation having the formula (D-1).

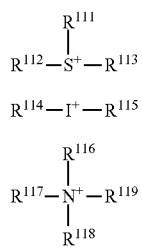

(B-1)
(C-1)
(D-1)

In formulae (B-1), (C-1) and (D-1), $R^{111}$ to $R^{119}$ are each independently a $C_1$-$C_{20}$ hydrocarbyl group which may contain a heteroatom. $R^{111}$ and $R^{112}$ may bond together to form a ring with the sulfur atom to which they are attached. $R^{116}$ and $R^{117}$ may bond together to form a ring with the sulfur atom to which they are attached.

The hydrocarbyl group represented by $R^{111}$ to $R^{119}$ may be saturated or unsaturated and straight, branched or cyclic. Examples thereof include $C_1$-$C_{20}$ alkyl groups such as methyl, ethyl, n-propyl, isopropyl, n-butyl, isobutyl, sec-butyl, tert-butyl, n-pentyl, n-hexyl, n-octyl, n-nonyl, n-decyl, undecyl, dodecyl, tridecyl, tetradecyl, pentadecyl, heptadecyl, octadecyl, nonadecyl and icosyl; $C_3$-$C_{20}$ cyclic saturated hydrocarbyl groups such as cyclopropyl, cyclopentyl, cyclohexyl, cyclopropylmethyl, 4-methylcyclohexyl, cyclohexylmethyl, norbornyl, and adamantyl; $C_2$-$C_{20}$ alkenyl groups such as vinyl, propenyl, butenyl and hexenyl; $C_3$-$C_{20}$ cyclic unsaturated aliphatic hydrocarbyl groups such as cyclohexenyl and norbornenyl; $C_2$-$C_{20}$ alkynyl groups such as ethynyl, propynyl and butynyl; $C_6$-$C_{20}$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutylnaphthyl, sec-butylnaphthyl and tert-butylnaphthyl; $C_7$-$C_{20}$ aralkyl groups such as benzyl and phenethyl; and combinations thereof. In the hydrocarbyl group, some or all of the hydrogen atoms may be substituted by a moiety containing a heteroatom such as oxygen, sulfur, nitrogen or halogen, and some constituent —$CH_2$— may be replaced by a moiety containing a heteroatom such as oxygen, sulfur or nitrogen, so that the group may contain a hydroxy moiety, fluorine, chlorine, bromine, iodine, cyano moiety, nitro moiety, carbonyl moiety, ether bond, ester bond, sulfonic ester bond, carbonate bond, lactone ring, sultone ring, carboxylic anhydride (—C(=O)—O—C(=O)—) or haloalkyl moiety.

The sulfonium cation in the sulfonium salt having formula (A) is also advantageously used as the onium cation $Mq^+$.

Also useful are quenchers of polymer type as described in U.S. Pat. No. 7,598,016 (JP-A 2008-239918). The polymeric quencher segregates at the resist surface and thus enhances the rectangularity of resist pattern. When a protective film is applied as is often the case in the immersion lithography, the polymeric quencher is also effective for preventing a film thickness loss of resist pattern or rounding of pattern top.

When used, the quencher is preferably added in an amount of 0 to 5 parts, more preferably 0 to 4 parts by weight per 100 parts by weight of the base polymer. The quencher may be used alone or in admixture.

Other Components

In addition to the foregoing components, the negative resist composition may contain other components such as an acid generator other than the sulfonium salt having formula (A), surfactant, crosslinker, radical generator, radical scavenger, water repellency improver, and acetylene alcohol. Each of the other components may be used alone or in admixture of two or more.

The other acid generator is typically a compound (PAG) capable of generating an acid in response to actinic ray or radiation. Although the PAG used herein may be any compound capable of generating an acid upon exposure to high-energy radiation, those compounds capable of generating sulfonic acid, imide acid (imidic acid) or methide acid are preferred. Suitable PAGs include sulfonium salts, iodonium salts, sulfonyldiazomethane, N-sulfonyloxyimide, and oxime-O-sulfonate acid generators. Exemplary PAGs are described in JP-A 2008-111103, paragraphs [0122]-[0142] (U.S. Pat. No. 7,537,880), JP-A 2018-005224, and JP-A 2018-025789. The other acid generator is preferably used in an amount of 0 to 200 parts, more preferably 0.1 to 100 parts by weight per 100 parts by weight of the base polymer.

Exemplary surfactants are described in JP-A 2008-111103, paragraphs [0165]-[0166]. Inclusion of a surfactant may improve or control the coating characteristics of the resist composition. The surfactant is preferably added in an amount of 0.0001 to 10 parts by weight per 100 parts by weight of the base polymer.

When the crosslinker is added to the negative resist composition, the dissolution rate of a resist film in the exposed region is reduced whereby the negative pattern is improved in rectangularity. Suitable crosslinkers which can be used herein include epoxy compounds, melamine compounds, guanamine compounds, glycoluril compounds and urea compounds having substituted thereon at least one group selected from among methylol, alkoxymethyl and acyloxymethyl groups, isocyanate compounds, azide compounds, and compounds having a double bond such as an alkenyloxy, acryloyl, methacryloyl or styryl group.

These compounds may be used as an additive or introduced into a polymer side chain as a pendant. Hydroxy-containing compounds may also be used as the crosslinker.

Suitable epoxy compounds include tris(2,3-epoxypropyl) isocyanurate, trimethylolmethane triglycidyl ether, trimethylolpropane triglycidyl ether, and triethylolethane triglycidyl ether. Examples of the melamine compound include hexamethylol melamine, hexamethoxymethyl melamine, hexamethylol melamine compounds having 1 to 6 methylol groups methoxymethylated and mixtures thereof, hexamethoxyethyl melamine, hexaacyloxymethyl melamine, hexamethylol melamine compounds having 1 to 6 methylol groups acyloxymethylated and mixtures thereof. Examples of the guanamine compound include tetramethylol guanamine, tetramethoxymethyl guanamine, tetramethylol guanamine compounds having 1 to 4 methylol groups methoxymethylated and mixtures thereof, tetramethoxyethyl guanamine, tetraacyloxyguanamine, tetramethylol guanamine compounds having 1 to 4 methylol groups acyloxymethylated and mixtures thereof. Examples of the glycoluril compound include tetramethylol glycoluril, tetramethoxyglycoluril, tetramethoxymethyl glycoluril, tetramethylol glycoluril compounds having 1 to 4 methylol groups methoxymethylated and mixtures thereof, tetramethylol glycoluril compounds having 1 to 4 methylol groups acyloxymethylated and mixtures thereof. Examples of the urea compound include tetramethylol urea, tetramethoxymethyl urea, tetramethylol urea compounds having 1 to 4 methylol groups methoxymethylated and mixtures thereof, and tetramethoxyethyl urea.

Suitable isocyanate compounds include tolylene diisocyanate, diphenylmethane diisocyanate, hexamethylene diisocyanate and cyclohexane diisocyanate. Suitable azide compounds include 1,1'-biphenyl-4,4'-bisazide, 4,4'-methylidenebisazide, and 4,4'-oxybisazide. Examples of the alkenyloxy group-containing compound include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylol propane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylol propane trivinyl ether.

In the negative resist composition, the crosslinker is preferably added in an amount of 0.1 to 50 parts, more preferably 1 to 40 parts by weight per 100 parts by weight of the base polymer.

A radical generator may be added to the negative resist composition for the purpose of increasing the reactivity of a double bond in the acid generator. As the radical generator, photo-radical generators are preferred. Examples include acetophenone, 4,4'-dimethoxybenzyl, benzyl, benzoin, benzophenone, 2-benzoylbenzoic acid, 4,4'-bis(dimethylamino) benzophenone, 4,4'-bis(diethylamino)benzophenone, benzoin methyl ether, benzoin ethyl ether, benzoin isopropyl ether, benzoin butyl ether, benzoin isobutyl ether, 4-benzoylbenzoic acid, 2,2'-bis(2-chlorophenyl)-4,4',5,5'-tetraphenyl-1,2'-biimidazole, methyl 2-benzoylbenzoate, 2-(1,3-benzodioxol-5-yl)-4,6-bis(trichloromethyl)-1,3,5-triazine, 2-benzyl-2-(dimethylamino)-4'-morpholinobutyrophenone, 4,4'-dichlorobenzophenone, 2,2-diethoxyacetophenone, 2,2-dimethoxy-2-phenylacetophenone, 2,4-diethylthioxanthen-9-one, diphenyl(2,4,6-trimethylbenzoyl)phosphine oxide, 1,4-dibenzoylbenzene, 2-ethylanthraquinone, 1-hydroxycyclohexyl phenyl ketone, 2-hydroxy-2-methylpropiophenone, 2-hydroxy-4'-(2-hydroxyethoxy)-2-methylpropiophenone, 2-isonitropropiophenone, 2-phenyl-2-(p-toluenesulfonyloxy)acetophenone (BAPO), and camphorquinone.

When added, the radical generator is preferably used in an amount of 0.1 to 50 parts by weight per 100 parts by weight of the base polymer.

A radical scavenger may be added to the negative resist composition for the purpose of suppressing the diffusion of radicals. Suitable radical scavengers include hindered phenol compounds, quinone compounds, hindered amine compounds, thiol compounds, and TEMPO compounds. Exemplary hindered phenol compounds include dibutylhydroxytoluene (BHT) and 2,2'-methylenebis(4-methyl-6-tert-butylphenol) (Antage W-400 by Kawaguchi Chemical Industry Co., Ltd.). Exemplary quinone compounds include 4-methoxyphenol (or hydroquinone monomethyl ether) and hydroquinone.

Typical of the hindered amine compound is 2,2,6,6-tetramethylpiperidine. Exemplary thiol compounds include dodecanethiol and hexadecanethiol. Typical of the TEMPO compound is 2,2,6,6-tetramethylpiperidine N-oxy radical.

When added, the radical scavenger is preferably used in an amount of 0 to 5 parts, more preferably 0 to 4 parts by weight per 100 parts by weight of the base polymer.

To the resist composition, the water repellency improver may be added for improving the water repellency on surface of a resist film. The water repellency improver may be used in the topcoatless immersion lithography. Suitable water repellency improvers include polymers having a fluoroalkyl group and polymers of specific structure having a 1,1,1,3,3,3-hexafluoro-2-propanol residue and are described in JP-A 2007-297590 and JP-A 2008-111103, for example. The water repellency improver to be added to the resist composition should be soluble in organic solvent developers. The water repellency improver of specific structure having a 1,1,1,3,3,3-hexafluoro-2-propanol residue is well soluble in the developer. A polymer having an amino group or amine salt copolymerized as repeat units may serve as the water repellent additive and is effective for preventing evaporation of acid during PEB, thus preventing any hole pattern opening failure after development. An appropriate amount of the water repellency improver is 0 to 20 parts, preferably 0.5 to 10 parts by weight per 100 parts by weight of the base polymer.

Suitable acetylene alcohols are described in JP-A 2008-122932, paragraphs [0179]-[0182]. An appropriate amount of the acetylene alcohol blended is 0 to 5 parts by weight per 100 parts by weight of the base polymer.

Process

The negative resist composition is used in the fabrication of various integrated circuits. Pattern formation using the resist composition may be performed by well-known lithography processes. The process generally involves the steps of applying the negative resist composition onto a substrate to form a resist film thereon, exposing the resist film to high-energy radiation, and developing the exposed resist film in a developer.

For example, the negative resist composition is first applied onto a substrate on which an integrated circuit is to be formed (e.g., Si, $SiO_2$, SiN, SiON, TiN, WSi, BPSG, SOG, or organic antireflective coating) or a substrate on which a mask circuit is to be formed (e.g., Cr, CrO, CrON, $MoSi_2$, or $SiO_2$) by a suitable coating technique such as spin coating, roll coating, flow coating, dipping, spraying or doctor coating. The coating is prebaked on a hotplate at a temperature of 60 to 150° C. for 10 seconds to 30 minutes, preferably at 80 to 120° C. for 30 seconds to 20 minutes. The resulting resist film is generally 0.01 to 2 μm thick.

Then the resist film is exposed patternwise to high-energy radiation. Examples of the high-energy radiation include UV, deep-UV, EB, EUV of wavelength 3 to 15 nm, x-ray, soft x-ray, excimer laser light, γ-ray or synchrotron radiation. On use of UV, deep UV, EUV, x-ray, soft x-ray, excimer laser, γ-ray or synchrotron radiation, the resist film is exposed directly or through a mask having a desired pattern, preferably in a dose of about 1 to 200 mJ/cm², more preferably about 10 to 100 mJ/cm². On use of EB, a pattern may be written directly or through a mask having a desired pattern, preferably in a dose of about 0.1 to 500 μC/cm², more preferably about 0.5 to 400 μC/cm². The resist composition is suited for micropatterning using high-energy radiation such as KrF excimer laser, ArF excimer laser, EB, EUV, x-ray, soft x-ray, γ-ray or synchrotron radiation, especially EB or EUV.

During the exposure to high-energy radiation, the anion having a maleimide group generates radicals, which act for the double bond in the cation of the acid generator having formula (A) in the exposed region of the resist film to polymerize, that is, crosslinking reaction takes place. With the progress of crosslinking reaction, the resist film remaining in the exposed region becomes thicker for thereby enhancing the dissolution contrast, and the resist film in the exposed region increases its mechanical strength for thereby minimizing the likelihood of pattern collapse.

After the exposure, the resist film may be baked (PEB) on a hotplate or in an oven at 30 to 150° C. for 10 seconds to 30 minutes, preferably at 50 to 120° C. for 30 seconds to 20 minutes.

Next, organic solvent development is carried out to form a negative tone pattern. The developer used herein is preferably selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, isopentyl acetate, 2-methylbutyl acetate, hexyl acetate, butenyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol, 1-butyl alcohol, 2-butyl alcohol, isobutyl alcohol, t-butyl alcohol, 1-pentanol, 2-pentanol, 3-pentanol, t-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-s-butyl ether, di-n-pentyl ether, diisopentyl ether, di-s-pentyl ether, di-t-pentyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable aromatic solvents include toluene, xylene, ethylbenzene, isopropylbenzene, t-butylbenzene and mesitylene. The solvents may be used alone or in admixture.

Rinsing is effective for minimizing the risks of resist pattern collapse and defect formation. However, rinsing is not essential. If rinsing is omitted, the amount of solvent used may be reduced.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

EXAMPLES

Examples of the invention are given below by way of illustration and not by way of limitation. The abbreviation "pbw" is parts by weight.

Acid generators PAG-1 to PAG-14 of the structure shown below were used in resist compositions. These acid generators were synthesized by ion exchange of an ammonium salt of fluorosulfonic acid providing the relevant anion with a sulfonium chloride providing the relevant cation.

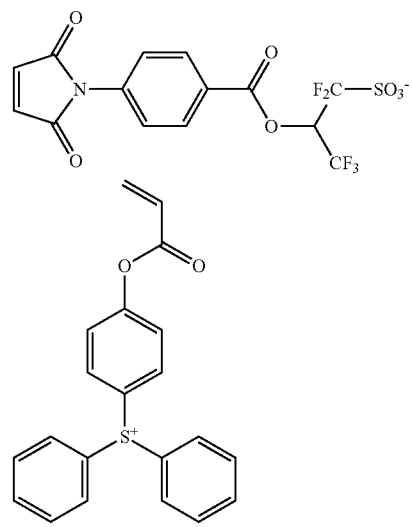

PAG-1

PAG-2
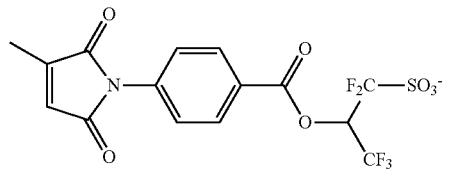
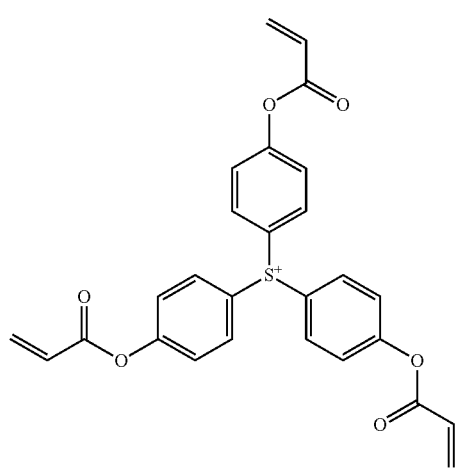
PAG-3
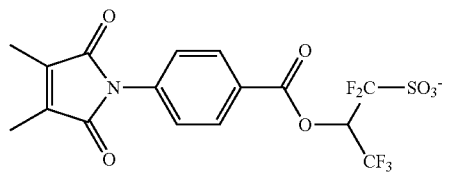
PAG-4
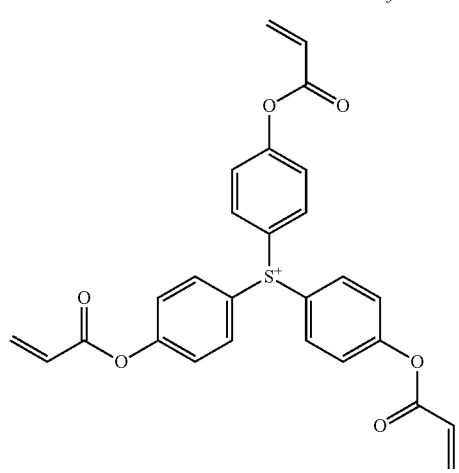
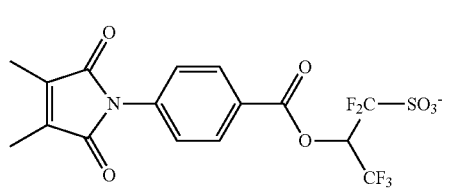
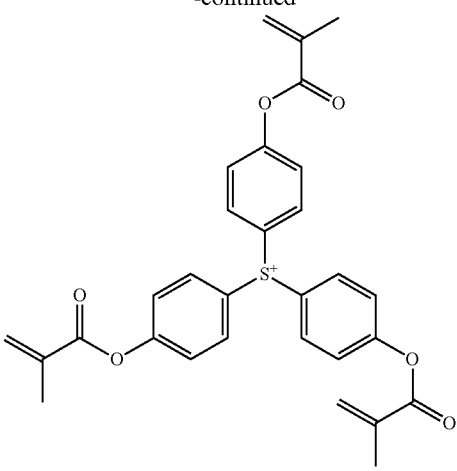
PAG-5
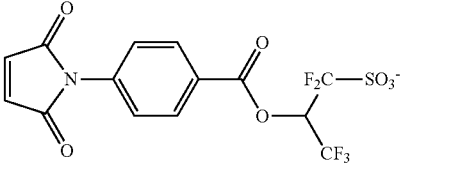
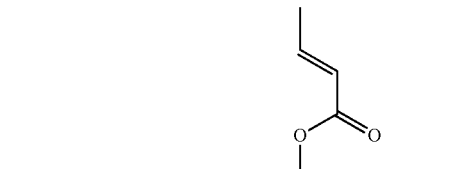
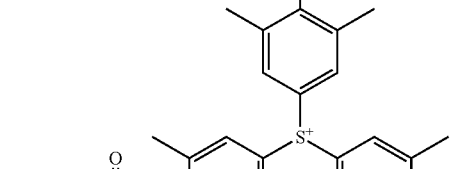
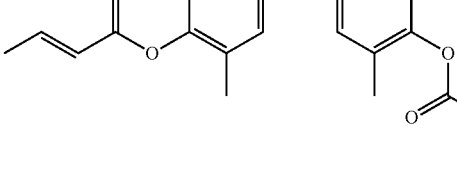
PAG-6
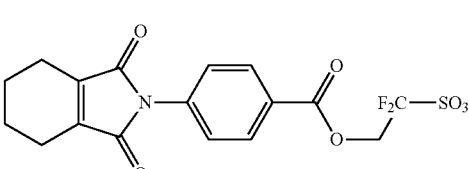
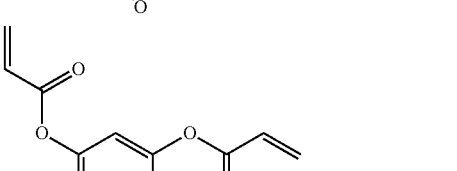
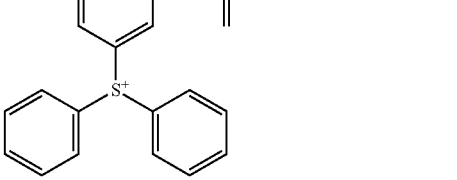

PAG-7
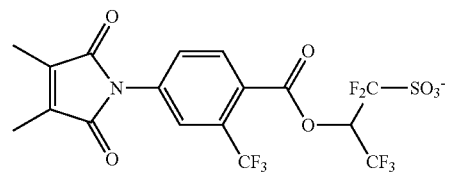
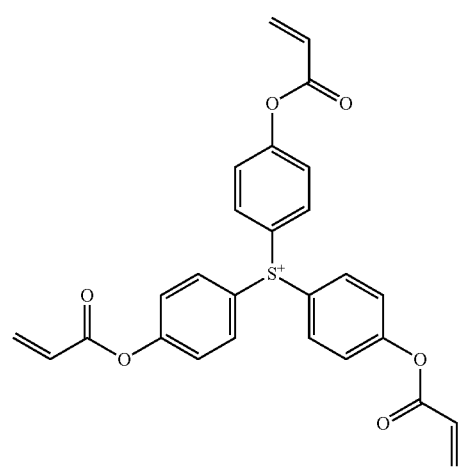
PAG-8
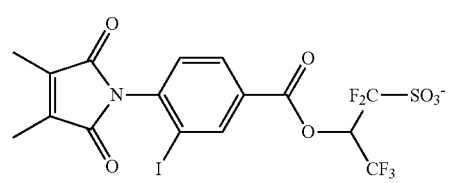
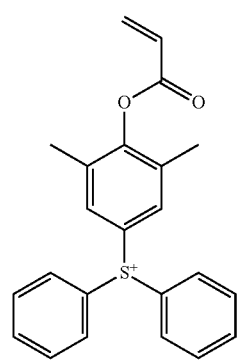
PAG-9
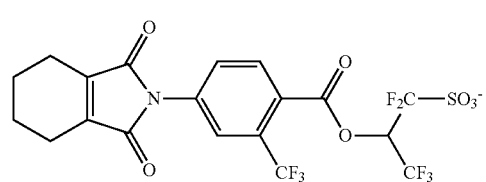
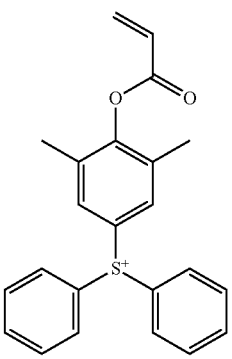
PAG-10
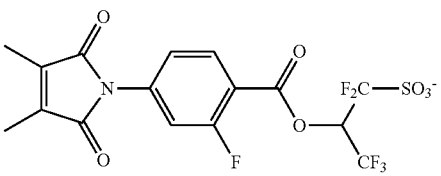
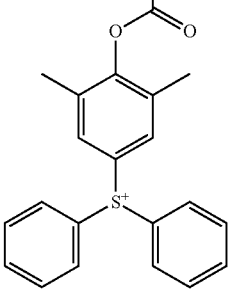
PAG-11
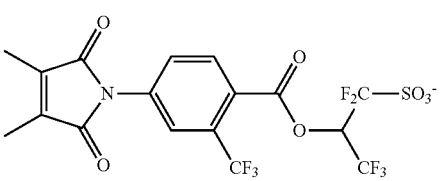
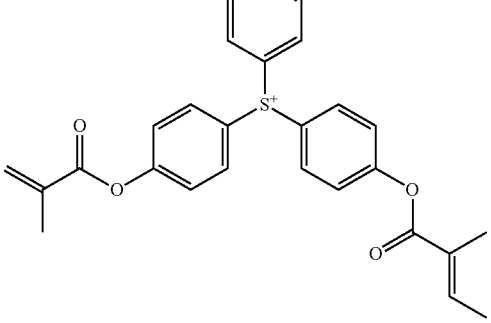

PAG-12

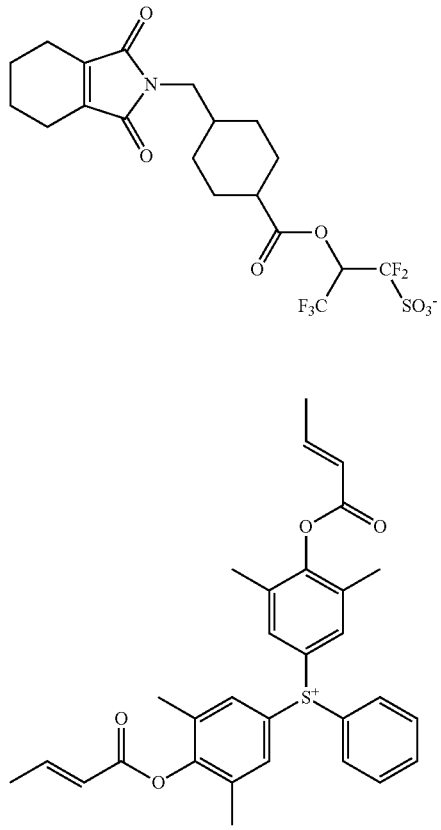

PAG-13

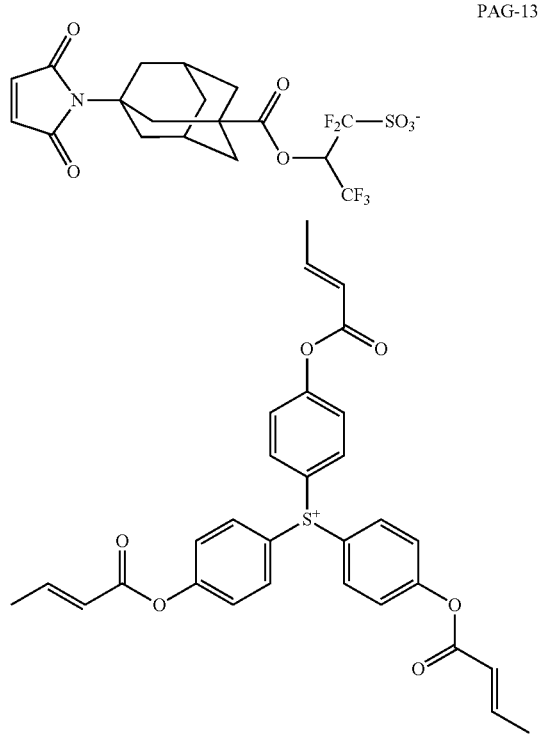

PAG-14

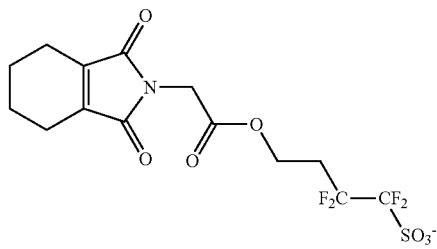

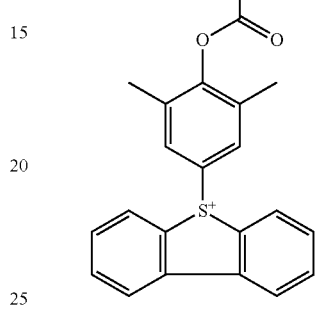

Synthesis Example

Synthesis of Base Polymers (Polymers P-1 to P-5)

Each of base polymers (Polymers P-1 to P-5) of the composition shown below was prepared by combining selected monomers, effecting copolymerization reaction in THF solvent, pouring into methanol for precipitation, washing the solid precipitate with hexane, isolation, and drying. The polymer was analyzed for composition by $^1$H-NMR and for Mw and Mw/Mn by GPC versus polystyrene standards using THF solvent.

P-1

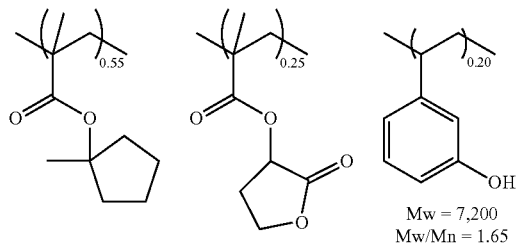

Mw = 7,200
Mw/Mn = 1.65

P-2

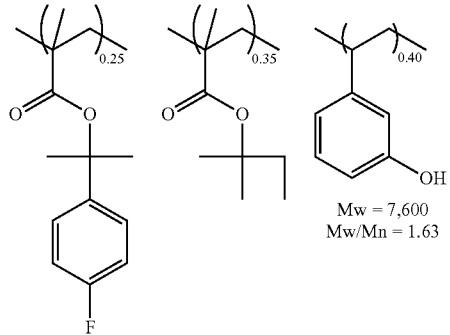

Mw = 7,600
Mw/Mn = 1.63

-continued

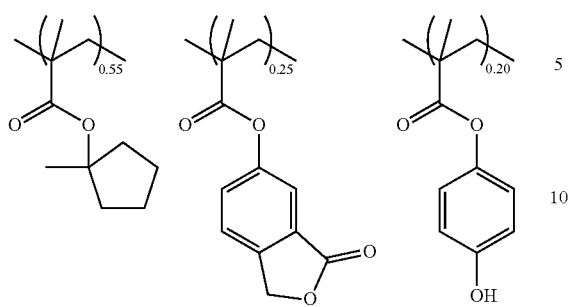
P-3
Mw = 6,200
Mw/Mn = 1.65

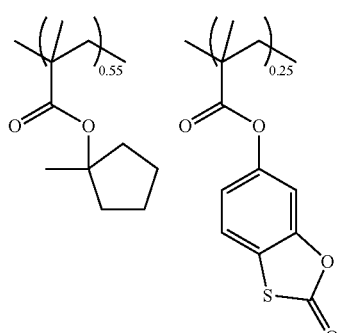
P-4
Mw = 7,100
Mw/Mn = 1.69

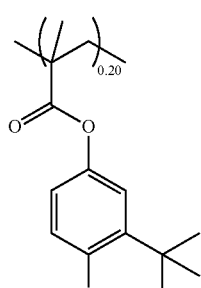

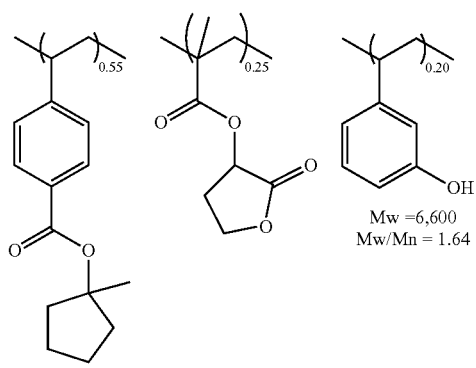
P-5
Mw = 6,600
Mw/Mn = 1.64

Examples 1 to 23 and Comparative Examples 1 to 3

Preparation and Evaluation of Negative Resist Compositions (1) Preparation of Negative Resist Compositions A negative resist composition was prepared by dissolving the selected components in a solvent in accordance with the recipe shown in Tables 1 and 2, and filtering through a filter with a pore size of 0.2 μm. The solvent contained 100 ppm of surfactant PolyFox PF-636 (Omnova Solutions Inc.).

The components in Tables 1 and 2 are identified below.

Organic Solvent:
  PGMEA (propylene glycol monomethyl ether acetate)
  PGME (propylene glycol monomethyl ether)
  EL (ethyl lactate)
  DAA (diacetone alcohol)

Comparative Acid Generators: cPAG-1 to cPAG-3

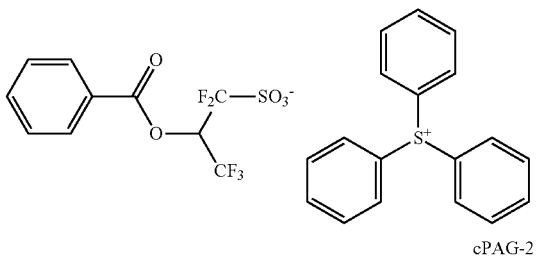
cPAG-1

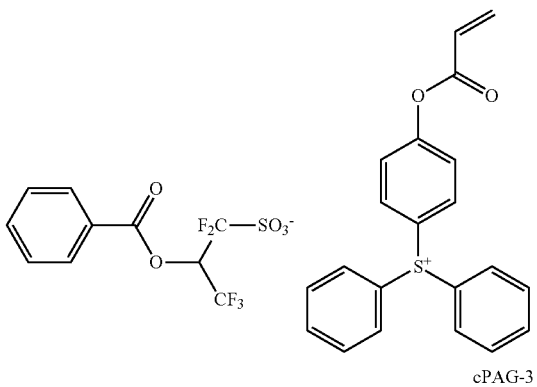
cPAG-2 cPAG-3

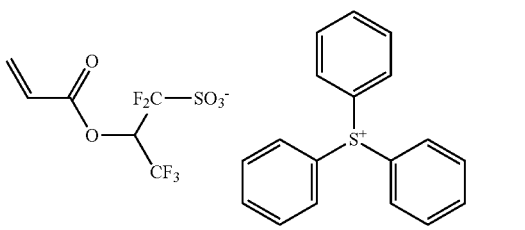

Quenchers: Q-1 to Q-4

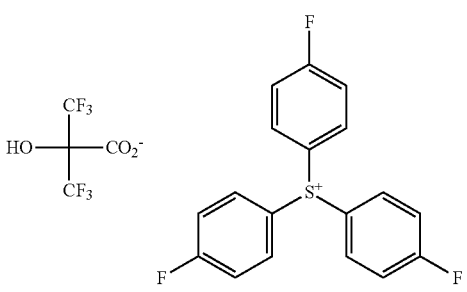
Q-1

-continued

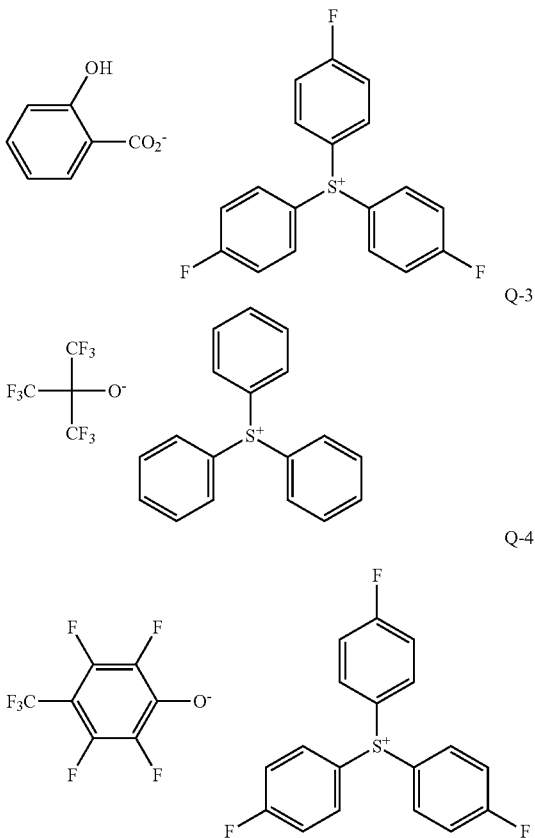

Radical Scavengers: RC-1 and RC-2

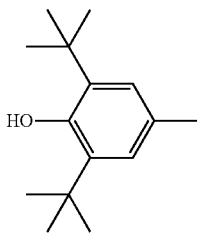

-continued

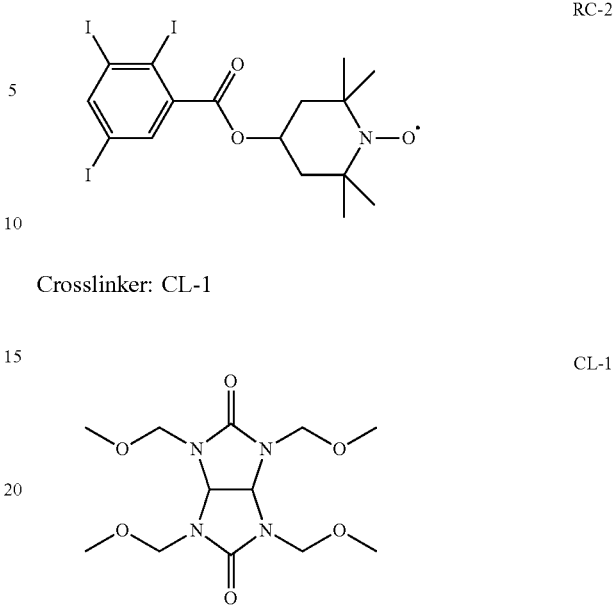

Crosslinker: CL-1

(2) EB Lithography Test

An antireflective coating material DUV-42 (Nissan Chemical Corp.) was coated onto a silicon substrate and baked at 200° C. for 60 seconds to form an ARC of 60 nm thick. Each of the negative resist compositions in Tables 1 and 2 was spin coated onto the ARC and prebaked on a hotplate at 105° C. for 60 seconds to form a resist film of 35 nm thick. Using an EB lithography system ELS-F125 (Elionix Co., Ltd., accelerating voltage 125 kV, current 50 pA), the resist film was exposed imagewise to EB. The resist film was baked (PEB) on a hotplate at the temperature shown in Tables 1 and 2 for 60 seconds and then developed in 2-methylbutyl acetate for 30 seconds to form a 1:1 line-and-space pattern of 30 nm.

The resulting resist pattern was observed under CD-SEM CG5000 (Hitachi High Technologies Corp.). The optimum exposure dose that provides a 1:1 LS pattern of 30 nm is determined and reported as sensitivity. The minimum line width (nm) of the LS pattern which is kept separate at the optimum dose is determined and reported as maximum resolution. The results are shown in Tables 1 and 2 together with the formulation of resist composition.

TABLE 1

| | | Polymer (pbw) | Acid generator (pbw) | Quencher and additive (pbw) | Organic solvent (pbw) | PEB temp. (° C.) | Sensitivity (μC/cm$^2$) | Maximum resolution (nm) |
|---|---|---|---|---|---|---|---|---|
| Example | 1 | P-1 (100) | PAG-1 (15.2) | Q-1 (7.92) | PGMEA (1,500) EL (3,000) | 80 | 250 | 20 |
| | 2 | P-1 (100) | PAG-2 (18.3) | Q-1 (7.92) | PGMEA (500) EL (4,000) | 80 | 230 | 19 |
| | 3 | P-1 (100) | PAG-3 (18.6) | Q-1 (7.92) | PGMEA (500) EL (4,000) | 80 | 220 | 19 |
| | 4 | P-1 (100) | PAG-4 (19.4) | Q-1 (7.92) | PGMEA (4,000) PGME (700) | 80 | 240 | 19 |
| | 5 | P-1 (100) | PAG-5 (20.8) | Q-1 (7.92) | PGMEA (4,000) PGME (700) | 80 | 230 | 18 |
| | 6 | P-1 (100) | PAG-6 (16.3) | Q-1 (7.92) | PGMEA (4,000) PGME (700) | 80 | 220 | 19 |
| | 7 | P-1 (100) | PAG-7 (19.9) | Q-1 (7.92) | PGMEA (4,000) PGME (700) | 80 | 230 | 19 |

TABLE 1-continued

| | Polymer (pbw) | Acid generator (pbw) | Quencher and additive (pbw) | Organic solvent (pbw) | PEB temp. (°C.) | Sensitivity (μC/cm$^2$) | Maximum resolution (nm) |
|---|---|---|---|---|---|---|---|
| 8 | P-1 (100) | PAG-8 (18.9) | Q-1 (7.92) | PGMEA (4,000) PGME (700) | 80 | 230 | 19 |
| 9 | P-1 (100) | PAG-9 (18.2) | Q-1 (7.92) | PGMEA (4,000) DAA (500) | 80 | 230 | 20 |
| 10 | P-1 (100) | PAG-10 (16.7) | Q-1 (7.92) | PGMEA (4,000) DAA (500) | 80 | 240 | 20 |
| 11 | P-1 (100) | PAG-11 (27.5) | Q-1 (7.92) | PGMEA (4,000) DAA (500) | 80 | 210 | 19 |
| 12 | P-1 (100) | PAG-12 (24.7) | Q-1 (7.92) | PGMEA (4,000) DAA (500) | 80 | 220 | 19 |
| 13 | P-1 (100) | PAG-13 (25.7) | Q-1 (7.92) | PGMEA (4,000) DAA (500) | 80 | 250 | 21 |
| 14 | P-1 (100) | PAG-14 (19.8) | Q-1 (7.92) | PGMEA (4,000) DAA (500) | 80 | 260 | 20 |
| 15 | P-2 (100) | PAG-11 (27.5) | Q-1 (7.92) | PGMEA (4,000) DAA (500) | 80 | 240 | 19 |
| 16 | P-3 (100) | PAG-11 (27.5) | Q-1 (7.92) | PGMEA (4,000) DAA (500) | 80 | 250 | 21 |
| 17 | P-4 (100) | PAG-11 (27.5) | Q-1 (7.92) | PGMEA (4,000) DAA (500) | 80 | 260 | 20 |
| 18 | P-5 (100) | PAG-11 (27.5) | Q-1 (7.92) | PGMEA (4,000) DAA (500) | 80 | 220 | 21 |
| 19 | P-1 (100) | PAG-11 (27.5) | Q-2 (6.81) | PGMEA (4,000) DAA (500) | 80 | 230 | 19 |
| 20 | P-1 (100) | PAG-11 (27.5) | Q-3 (7.47) | PGMEA (4,000) DAA (500) | 80 | 240 | 19 |
| 21 | P-1 (100) | PAG-11 (27.5) | Q-4 (8.25) CL-1 (3.0) | PGMEA (4,000) DAA (500) | 80 | 230 | 19 |
| 22 | P-1 (100) | PAG-11 (27.5) | Q-4 (8.25) RC-1 (1.0) | PGMEA (4,000) DAA (500) | 80 | 250 | 18 |
| 23 | P-1 (100) | PAG-11 (27.5) | Q-4 (8.25) RC-2 (2.0) CL-1 (3.0) | PGMEA (4,000) DAA (500) | 80 | 240 | 18 |

TABLE 2

| | | Polymer (pbw) | Acid generator (pbw) | Quencher and additive (pbw) | Organic solvent (pbw) | PEB temp. (°C.) | Sensitivity (μC/cm$^2$) | Maximum resolution (nm) |
|---|---|---|---|---|---|---|---|---|
| Comparative Example | 1 | P-1 (100) | cPAG-1 (14.9) | Q-1 (7.92) | PGMEA (4,000) DAA (500) | 80 | 340 | 25 |
| | 2 | P-1 (100) | cPAG-2 (16.7) | Q-1 (7.92) | PGMEA (4,000) DAA (500) | 80 | 310 | 24 |
| | 3 | P-1 (100) | cPAG-3 (13.7) | Q-1 (7.92) | PGMEA (4,000) DAA (500) | 80 | 300 | 24 |

As seen from Table 1, the negative resist compositions containing a sulfonium salt consisting of a sulfonate anion having a maleimide group and a cation having a polymerizable double bond as the acid generator exhibit excellent maximum resolution.

Japanese Patent Application No. 2021-123215 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A negative resist composition comprising a base polymer and an acid generator in the form of a sulfonium salt consisting of a sulfonate anion having a maleimide group and a cation having a polymerizable double bond, wherein the sulfonium salt has the formula (A):

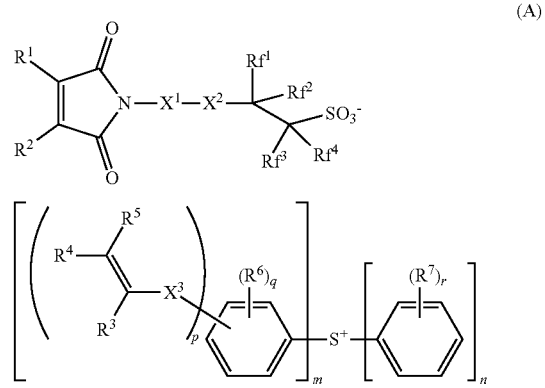

wherein m is an integer of 1 to 3, n is an integer of 0 to 2, meeting m+n=3, p is 1 or 2, q is an integer of 0 to 4, meeting 1≤p+q≤5, r is an integer of 0 to 5, $X^1$ is a single bond or a $C_1$-$C_{20}$ hydrocarbylene group which may contain oxygen, sulfur, nitrogen or halogen, $X^2$ is an ester bond or $C_1$-$C_8$ alkanediyl group, $X^3$ is a single bond, ester bond, ether bond, amide bond, urethane bond, or a $C_1$-$C_{10}$ alkanediyl group in which some constituent —$CH_2$— may be replaced by an ester bond, ether bond, amide bond or urethane bond, $R^1$ and $R^2$ are each independently hydrogen or a $C_1$-$C_{10}$ saturated hydrocarbyl group, $R^1$ and $R^2$ may bond together to form a ring with the carbon atoms to which they are attached, $R^3$ to $R^5$ are each independently hydrogen, halogen, or a $C_1$-$C_{40}$ saturated hydrocarbyl group in which some or all of the hydrogen atoms may be substituted by fluorine or hydroxy, some constituent —$CH_2$— may be replaced by an ether bond or ester bond, and some carbon-carbon bond may be a double bond, $R^6$ and $R^7$ are each independently halogen, cyano, nitro, mercapto, sulfo, a $C_1$-$C_{10}$ saturated hydrocarbyl group, or a $C_7$-$C_{20}$ aralkyl group, the saturated hydrocarbyl group and aralkyl group may contain oxygen, sulfur, nitrogen or halogen, two $R^6$ or two $R^7$ may bond together to form a ring with the benzene ring to which they are attached, and $R^6$ and $R^7$ may bond together to form a ring with the benzene rings to which they are attached and the intervening sulfur, $Rf^1$ to $Rf^4$ are each independently hydrogen, fluorine or trifluoromethyl, at least one of $Rf^1$ to $Rf^1$ being fluorine or trifluoromethyl, $Rf^1$ and $Rf^2$, taken together, may form a carbonyl group.

2. The resist composition of claim 1 wherein the base polymer comprises repeat units having the formula (a1):

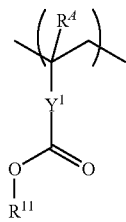

(a1)

wherein $R^A$ is hydrogen or methyl, $Y^1$ is a single bond, phenylene, naphthylene or a $C_1$-$C_{12}$ linking group which contains at least one moiety selected from an ester bond, ether bond and lactone ring, and $R^{11}$ is an acid labile group.

3. The resist composition of claim 1, further comprising an organic solvent.

4. The resist composition of claim 1, further comprising a quencher.

5. The resist composition of claim 1, further comprising a crosslinker.

6. The resist composition of claim 1, further comprising a surfactant.

7. A pattern forming process comprising the steps of applying the negative resist composition of claim 1 onto a substrate to form a resist film thereon, exposing the resist film to high-energy radiation, and developing the exposed resist film in an organic solvent developer.

8. The process of claim 7 wherein the developer comprises at least one organic solvent selected from the group consisting of 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, isopentyl acetate, 2-methylbutyl acetate, hexyl acetate, butenyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

9. The process of claim 7 wherein the high-energy radiation is KrF excimer laser, ArF excimer laser, EB, or EUV of wavelength 3 to 15 nm.

* * * * *